(12) United States Patent
Mahadevan et al.

(10) Patent No.: US 11,160,299 B2
(45) Date of Patent: Nov. 2, 2021

(54) PROTEIN COMPOSITIONS AND CONSUMABLE PRODUCTS THEREOF

(71) Applicant: Clara Foods Co., South San Francisco, CA (US)

(72) Inventors: Kritika Mahadevan, South San Francisco, CA (US); Joel Andrew Kreps, South San Francisco, CA (US); Isha Joshi, South San Francisco, CA (US); Farnoosh Ayoughi, South San Francisco, CA (US); Weixi Zhong, South San Francisco, CA (US); Harshal Kshirsagar, South San Francisco, CA (US); Alexandre Chapeaux, South San Francisco, CA (US); Wesley Rutherford-Jenkins, South San Francisco, CA (US); Ranjan Patnaik, South San Francisco, CA (US); Frank Douglas Ivey, South San Francisco, CA (US)

(73) Assignee: Clara Foods Co., South San Francisco, CA (US)

( * ) Notice: Subject to any disclaimer, the term of this patent is extended or adjusted under 35 U.S.C. 154(b) by 43 days.

(21) Appl. No.: 16/986,016

(22) Filed: Aug. 5, 2020

(65) Prior Publication Data

US 2021/0007384 A1    Jan. 14, 2021

Related U.S. Application Data

(63) Continuation of application No. PCT/US2020/041720, filed on Jul. 10, 2020.

(60) Provisional application No. 62/873,154, filed on Jul. 11, 2019, provisional application No. 62/873,159, filed on Jul. 11, 2019.

(51) Int. Cl.
    A23L 33/18    (2016.01)
    A23J 1/18    (2006.01)

(52) U.S. Cl.
    CPC .................. *A23L 33/18* (2016.08); *A23J 1/18* (2013.01)

(58) Field of Classification Search
    CPC ............. C07K 14/77; A23L 33/18; A23J 1/18
    USPC ...................................... 426/18, 47
    See application file for complete search history.

(56) References Cited

U.S. PATENT DOCUMENTS

| | | |
|---|---|---|
| 897,192 A | 8/1908 | Joseph |
| 3,251,697 A | 5/1966 | Hans et al. |
| 3,806,608 A | 4/1974 | Perret |
| 4,355,022 A | 10/1982 | Rabussay |
| 4,430,428 A | 2/1984 | Fraser et al. |

(Continued)

FOREIGN PATENT DOCUMENTS

| | | |
|---|---|---|
| AU | 2005264767 A1 | 1/2006 |
| CA | 2574558 A1 | 1/2006 |

(Continued)

OTHER PUBLICATIONS

Sequence of ovomucoid—Designated BCC05658 (Year: 2012).*

(Continued)

*Primary Examiner* — Hamid R Badr
(74) *Attorney, Agent, or Firm* — Wilson Sonsini Goodrich & Rosati

(57) ABSTRACT

Provided herein are compositions with enhanced protein content, proteins with high solubility, protein combinations and methods for the preparation thereof.

20 Claims, 17 Drawing Sheets

Specification includes a Sequence Listing.

(56) References Cited

U.S. PATENT DOCUMENTS

| | | |
|---|---|---|
| 4,675,201 A | 6/1987 | Lee et al. |
| 4,810,508 A | 3/1989 | Dell'Acqua et al. |
| 4,880,643 A | 11/1989 | Bamforth et al. |
| 5,019,411 A | 5/1991 | Johnson et al. |
| 5,149,521 A | 9/1992 | Hirose et al. |
| 5,283,236 A | 2/1994 | Chiou |
| 5,336,609 A | 8/1994 | Oberto et al. |
| 5,643,792 A | 7/1997 | Okabayashi et al. |
| 5,849,477 A | 12/1998 | O'Malley et al. |
| 6,204,012 B1 | 3/2001 | Hellmuth et al. |
| 6,316,034 B1 | 11/2001 | Daeschel et al. |
| 6,465,254 B1 | 10/2002 | Saito et al. |
| 6,495,344 B1 | 12/2002 | Carr et al. |
| 6,645,739 B2 | 11/2003 | Clark |
| 6,699,691 B2 | 3/2004 | Inan et al. |
| 6,730,499 B1 | 5/2004 | Cregg |
| 6,803,225 B2 | 10/2004 | Contreras et al. |
| 6,875,588 B2 | 4/2005 | Harvey et al. |
| 6,933,146 B2 | 8/2005 | Helliwell et al. |
| 6,994,876 B1 | 2/2006 | Sher et al. |
| 7,029,872 B2 | 4/2006 | Gerngross |
| 7,037,895 B2 | 5/2006 | Assaly et al. |
| 7,078,488 B2 | 7/2006 | Jiang et al. |
| 7,205,018 B2 | 4/2007 | Sherwood et al. |
| 7,252,933 B2 | 8/2007 | Contreras et al. |
| 7,294,507 B2 | 11/2007 | Harvey et al. |
| 7,326,681 B2 | 2/2008 | Gerngross |
| 7,335,761 B2 | 2/2008 | Harvey et al. |
| 7,345,150 B2 | 3/2008 | Assaly et al. |
| 7,348,312 B2 | 3/2008 | Assaly et al. |
| 7,507,573 B2 | 3/2009 | Contreras et al. |
| 7,595,186 B2 | 9/2009 | Gerdes et al. |
| 7,598,055 B2 | 10/2009 | Bobrowicz et al. |
| 7,629,163 B2 | 12/2009 | Gerngross |
| 7,745,200 B2 | 6/2010 | Cregg |
| 7,794,770 B2 | 9/2010 | Sherwood et al. |
| 7,799,363 B2 | 9/2010 | Sherwood et al. |
| 7,842,326 B2 | 11/2010 | Sherwood et al. |
| 7,884,068 B2 | 2/2011 | Assaly et al. |
| 7,897,192 B2 | 3/2011 | Sherwood et al. |
| 7,906,160 B2 | 3/2011 | Sherwood et al. |
| 7,923,430 B2 | 4/2011 | Gerngross |
| 7,923,431 B2 | 4/2011 | Wolff |
| 7,972,809 B2 | 7/2011 | Kobayashi et al. |
| 8,058,053 B2 | 11/2011 | Contreras et al. |
| 8,067,551 B2 | 11/2011 | Gerngross et al. |
| 8,075,919 B2 | 12/2011 | Brown et al. |
| 8,211,691 B2 | 7/2012 | Gerngross |
| 8,222,032 B2 | 7/2012 | Parker et al. |
| 8,227,207 B2 | 7/2012 | Miguel Castro et al. |
| 8,227,436 B2 | 7/2012 | Mcmillan et al. |
| 8,354,268 B2 | 1/2013 | Contreras et al. |
| 8,445,227 B2 | 5/2013 | Bobrowicz et al. |
| 8,546,136 B2 | 10/2013 | Serber et al. |
| 8,642,017 B2 | 2/2014 | Wagstaff |
| 8,663,971 B2 | 3/2014 | Contreras et al. |
| 8,697,394 B2 | 4/2014 | Bobrowicz et al. |
| 8,753,698 B2 | 6/2014 | Van Amerongen et al. |
| 8,778,659 B2 | 7/2014 | Govindappa et al. |
| 8,809,259 B2 | 8/2014 | Berry et al. |
| 8,815,580 B2 | 8/2014 | Callewaert et al. |
| 8,822,412 B2 * | 9/2014 | Berry .............. A61P 21/06 514/4.9 |
| 8,877,462 B2 | 11/2014 | Gerngross et al. |
| 8,883,445 B2 | 11/2014 | Contreras et al. |
| 8,883,483 B2 | 11/2014 | Gerngross et al. |
| 8,932,825 B2 | 1/2015 | Wildt et al. |
| 8,986,773 B2 | 3/2015 | Beckhoven Van et al. |
| 9,012,175 B2 | 4/2015 | Hartner et al. |
| 9,206,454 B2 | 12/2015 | Weis et al. |
| 9,220,292 B2 | 12/2015 | Jenkins |
| 9,279,129 B2 | 3/2016 | Hartner et al. |
| 9,359,628 B2 | 6/2016 | Contreras et al. |
| 9,598,474 B2 | 3/2017 | Berry et al. |
| 9,605,040 B2 | 3/2017 | Von Maltzahn et al. |
| 9,611,298 B2 | 4/2017 | Berry et al. |
| 9,617,550 B2 | 4/2017 | Gehlsen et al. |
| 9,689,016 B2 | 6/2017 | Marcel et al. |
| 9,700,071 B2 | 7/2017 | Silver et al. |
| 9,757,328 B2 | 9/2017 | Ferrari et al. |
| 2002/0098198 A1 | 7/2002 | Watts et al. |
| 2003/0069395 A1 | 4/2003 | Sato et al. |
| 2004/0142906 A1 | 7/2004 | Wang |
| 2004/0231010 A1 | 11/2004 | Murray et al. |
| 2005/0026264 A1 | 2/2005 | Jiang et al. |
| 2005/0090001 A1 | 4/2005 | Parker et al. |
| 2005/0266140 A1 | 12/2005 | Kastenmayer et al. |
| 2006/0228769 A1 | 10/2006 | Yano et al. |
| 2006/0280804 A1 | 12/2006 | Castro et al. |
| 2006/0280840 A1 | 12/2006 | Robertson |
| 2007/0065555 A1 | 3/2007 | Soane et al. |
| 2007/0141139 A1 | 6/2007 | Vandenberg |
| 2007/0231448 A1 | 10/2007 | Takahashi |
| 2008/0166447 A1 | 7/2008 | Strohbehn et al. |
| 2008/0214485 A1 | 9/2008 | Mcmillan et al. |
| 2008/0260913 A1 | 10/2008 | Orcutt et al. |
| 2009/0029005 A1 * | 1/2009 | Van Amerongen .... A61K 35/54 426/63 |
| 2009/0042249 A1 | 2/2009 | Lubys et al. |
| 2009/0178147 A1 | 7/2009 | Harvey |
| 2009/0191157 A1 | 7/2009 | Albrecht et al. |
| 2009/0263863 A1 | 10/2009 | Contreras et al. |
| 2009/0290005 A1 | 11/2009 | Wanibe et al. |
| 2011/0020811 A1 | 1/2011 | Crowell |
| 2012/0093994 A1 | 4/2012 | Hsieh et al. |
| 2012/0148585 A1 | 6/2012 | Saxon |
| 2013/0084361 A1 | 4/2013 | Shepheard |
| 2014/0170268 A1 | 6/2014 | Graeber et al. |
| 2014/0345004 A1 | 11/2014 | Callewaert et al. |
| 2014/0356507 A1 | 12/2014 | Tetrick et al. |
| 2014/0369996 A1 | 12/2014 | Ommundsen et al. |
| 2015/0152427 A1 | 6/2015 | Wildt et al. |
| 2015/0191607 A1 | 7/2015 | Mcdaniel |
| 2015/0284693 A1 | 10/2015 | Nagaoka |
| 2015/0305368 A1 | 10/2015 | Dake et al. |
| 2015/0307562 A1 | 10/2015 | Basu et al. |
| 2016/0024511 A1 | 1/2016 | Tolstorukov et al. |
| 2016/0038428 A1 | 2/2016 | Harel et al. |
| 2016/0039911 A1 | 2/2016 | Lesnicki et al. |
| 2016/0051593 A1 | 2/2016 | Raff |
| 2016/0068880 A1 | 3/2016 | Gerngross |
| 2016/0083722 A1 | 3/2016 | Young et al. |
| 2016/0106137 A1 | 4/2016 | Jenkins |
| 2016/0183567 A1 * | 6/2016 | Choi .............. A23L 25/00 426/614 |
| 2017/0029827 A1 | 2/2017 | Gasser et al. |
| 2017/0037418 A1 | 2/2017 | Mattanovich et al. |
| 2017/0159094 A1 | 6/2017 | Natunen et al. |
| 2018/0084814 A1 | 3/2018 | Challakere et al. |
| 2018/0355020 A1 | 12/2018 | Anchel |
| 2020/0138066 A1 | 5/2020 | Anchel |

FOREIGN PATENT DOCUMENTS

| | | |
|---|---|---|
| CN | 1214729 C | 8/2005 |
| CN | 101022737 A | 8/2007 |
| CN | 101623111 A | 1/2010 |
| CN | 101496575 B | 10/2010 |
| CN | 101496579 B | 10/2010 |
| CN | 102076221 A | 5/2011 |
| CN | 102429307 A | 5/2012 |
| CN | 102308940 B | 8/2012 |
| CN | 102978268 A | 3/2013 |
| CN | 102630865 B | 5/2013 |
| CN | 102008076 B | 7/2013 |
| CN | 103445263 A | 12/2013 |
| CN | 104172168 A | 12/2014 |
| CN | 104172186 A | 12/2014 |
| CN | 104187634 A | 12/2014 |
| CN | 104187666 A | 12/2014 |
| CN | 104256633 A | 1/2015 |
| CN | 104256648 A | 1/2015 |
| CN | 104431285 A | 3/2015 |
| CN | 104694560 A | 6/2015 |

(56) References Cited

FOREIGN PATENT DOCUMENTS

| | | | |
|---|---|---|---|
| CN | 104738624 A | 7/2015 | |
| CN | 104824674 A | 8/2015 | |
| CN | 104855977 A | 8/2015 | |
| CN | 104957356 A | 10/2015 | |
| CN | 104961823 A | 10/2015 | |
| CN | 105012941 A | 11/2015 | |
| CN | 105039189 A | 11/2015 | |
| CN | 103182074 B | 3/2016 | |
| CN | 104146248 B | 6/2016 | |
| CN | 105876440 A | 8/2016 | |
| CN | 106173829 A | 12/2016 | |
| CN | 106259946 A | 1/2017 | |
| EP | 0265884 B1 | 12/1992 | |
| EP | 1156719 B1 | 5/2003 | |
| EP | 1278511 B1 | 8/2004 | |
| EP | 1119264 B1 | 3/2005 | |
| EP | 1297172 B1 | 11/2005 | |
| EP | 1655308 A1 | 5/2006 | |
| EP | 1211310 B1 | 12/2006 | |
| EP | 1294910 B1 | 11/2008 | |
| EP | 1522590 B1 | 8/2009 | |
| EP | 2376349 B1 | 10/2012 | |
| EP | 2001312 B1 | 5/2014 | |
| EP | 2339013 B1 | 7/2014 | |
| EP | 2271222 B1 | 2/2015 | |
| EP | 2862933 A2 | 4/2015 | |
| EP | 2964775 A1 | 1/2016 | |
| EP | 3083966 A1 | 10/2016 | |
| EP | 1467615 B2 | 3/2017 | |
| ES | 2188336 A1 | 6/2003 | |
| ES | 2329316 B1 | 10/2010 | |
| FR | 2458585 A1 | 1/1981 | |
| GB | 1211361 A | 11/1970 | |
| GB | 2033905 B | 10/1982 | |
| JP | 2007259805 A | 10/2007 | |
| JP | 2008507270 A | 3/2008 | |
| JP | 5048487 B2 | 10/2012 | |
| JP | 2014171424 A | 9/2014 | |
| WO | WO-0200856 A2 | 1/2002 | |
| WO | WO-03102187 A1 | 12/2003 | |
| WO | WO-2004065593 A1 | 8/2004 | |
| WO | WO-2007106731 A2 | 9/2007 | |
| WO | WO-2012129036 A2 | 9/2012 | |
| WO | WO-2013148330 A1 | 10/2013 | |
| WO | WO-2015048339 A2 | 4/2015 | |
| WO | WO-2015048342 A2 | 4/2015 | |
| WO | WO-2016014900 A2 | 1/2016 | |
| WO | WO-2016077457 A1 | 5/2016 | |
| WO | WO-2016081645 A1 | 5/2016 | |
| WO | WO-2016160655 A1 | 10/2016 | |
| WO | WO-2016183056 A1 | 11/2016 | |
| WO | WO-2018162557 A2 | 9/2018 | |
| WO | WO-2020041483 A1 | 2/2020 | |

OTHER PUBLICATIONS

Fredericq, E. et al. J. Biol. Chem. 181: 499-510 (Year: 1949).*
Pelegrine, D.H.G. et al. Lebensm. Wiss U-Technol. 38: 77-80 (Year: 2005).*
Alleoni et al. Albumen foam stability and s-ovalbumin contents in eggs coated with whey protein concentrate. Brazilian Journal of Poultry Science, vol. 6, No. 2, pp. 105-110 (Apr.-Jun. 2004).
Ambort et al., Perspectives on Mucus Properties and Formation—Lessons from the Biochemical World, Cold Spring Harb Perspect Med; 2:a014159 (9 pages) (2012).
Anumula et al., A comprehensive procedure for preparation of partially methylated alditol acetates from glycoprotein carbohydrates, Anal Biochem., 203(1): 101-108 (1992).
AOAC Official Method 925.09. Solids (Total) and Moisture in Flour, Vacuum Oven Method. Final Action. JAOAC 8, 665(1925); 9, 39, 88(1926); 34, 278(1951). In Official Methods of Analysis of AOAC International, 16th Edition, vol. 2 (Copyright 1995, 1996, 1997, 1998, 1999).

AOAC Official Method 997.02. Yeast and Mold Counts in Foods, Dry Rehydratable Film Method (Petrifilm Method). First Action 1997, Final Action 2000. J AOAC Int 80, 806 (1997). Revised Mar. 2002. AOAC International. One page.
Arii et al. Structural properties of recombinant ovalbumin and its transformation into a thermostabilized form by alkaline treatment. Biosci Biotechnol Biochem. Aug. 1999;63(8):1392-9.doi: 10.1271/bbb.63.1392.
Arntfield et al. Characteristics of heat-induced networks for mixtures of ovalbumin and lysozyme. J Agric. Food Chem 41:2291-2295 (1993).
AW et al. Can too many copies spoil the broth? Microb Cell Fact. 2013; 12: 128.Published online Dec. 20, 2013. doi: 10.1186/1475-2859-12-128. 9 pages.
Babu. Modulation of Allergic Immune Responses by Engineered Recombinant Ovomucoid Third Domain and Potential Use for Immunotherapy. A Thesis Presented to The Faculty of Graduate Studies of The University of Guelph (Jan. 2006). 162 pages.
Buell et al. Isolation of recombinant plasmids bearing cDNA to hen ovomucoid and lysozyme mRNAs. J Biol Chem 254(18): 9277-9283 (Sep. 25, 1979).
Callewaert et al., Use of HDEL-tagged Trichoderma reesei mannosyl oligosaccharide 1,2-α-D-mannosidase for N-glycan engineering in Pichia pastoris, FEBS Letters, 503:173-178 (2001).
Catterall et al. Primary sequence of ovomucoid messenger RNA as determined from cloned complementary DNA. J Cell Biol 87(2 Pt 1):480-7 (Nov. 1980).
Charoenrat et al. Oxygen-limited fed-batch process: an alternative control for Pichia pastoris recombinant protein processes. Bioprocess Biosyst Eng. Oct. 2005;27(6):399-406. doi: 10.1007/s00449-005-0005-4. Epub Nov. 3, 2005.
Co-pending U.S. Appl. No. 16/891,835, filed Jun. 3, 2020.
Cre-Lox recombination, Wikipedia, downloaded Jun. 12, 2017.
Damasceno et al. An optimized fermentation process for high-level production of a single-chain Fv antibody fragment in Pichia pastoris. Protein Expr Purif. Sep. 2004;37(1):18-26.doi: 10.1016/j.pep.2004.03.019.
Digan et al. Continuous Production of a Novel Lysozyme via Secretion from the Yeast, *Pichia pastoris*. Bio/Technology 7:160-164(1989).
EP15858729.5 Extended European Report dated Aug. 13, 2018.
EP15858729.5 Partial Supplementary European Search Report dated May 11, 2018.
Hughey et al. Antimicrobial activity of lysozyme against bacteria involved in food spoilage and food-borne disease. Appl Environ Microbiol 53(9):2165-70 (Sep. 1987).
Hynes et al. mRNA complexity and egg white protein mRNA content in mature and hormone-withdrawn oviduct. Cell 11:923-932 (Aug. 1977).
International Search Report and Written Opinion dated Feb. 1, 2016 for International Application No. PCT/US2015/060147.
Jensen. The Basics of Western Blotting. Anat Rec (Hoboken) Mar. 2012;295(3):369-71.doi: 10.1002/ar.22424. Epub Feb. 3, 2012.
Johnson et al. Gelation Properties of Albumen Proteins, Singly and in Combination. Poultry Science 60:2071-2083 (1981).
Julshamin et al. Determination of Arsenic, Cadmium, Mercury, and Lead by Inductively Coupled Plasma/Mass Spectrometry in Foods after Pressure Digestion: NMKL Interlaboratory Study. Journal of AOAC International 90(3):844-856 (2007).
Kato et al. Chicken ovomucoid: determination of its amino acid sequence, determination of the trypsin reactive site, and preparation of all three of its domains. Biochemistry 26(1):193-201 (Jan. 13, 1987).
Krainer et al. Biotechnological advances towards an enhanced peroxidase production in Pichia pastoris. Journal of Biotechnology 233:181-189 (2016).
Lai et al. Molecular structure and flanking nucleotide sequences of the natural chicken ovomucoid gene. Cell 18:829-842 (1979).
Lin et al. Synthesis, Purification, and Active Site Mutagenesis of Recombinant Porcine Pepsinogen. The Journal of Biological Chemistry 264(8):4482-4489 (Mar. 15, 1989).
Lindenmaier et al. Isolation and characterization of the chicken ovomucoid gene. Nucleic Acids Res 7(5):1221-32 (Nov. 10, 1979).

(56) References Cited

OTHER PUBLICATIONS

Liu et al. Improved antioxidant activity and physicochemical properties of curcumin by adding ovalbumin and its structural characterization. Food Hydrocolloids 72:304-311 (2017). Available online Jun. 9, 2017.
Lv et al. Structural and Functional Properties of Ovalbumin Glycated by Dry-Heating in the Presence of Maltodextrin. International Journal of Food Properties, 18:1326-1333, 2015. DOI: 10.1080/10942912.2011.620204. Published online Mar. 3, 2015.
Mainwaring et al. Effect of pH on hen egg white lysozyme production and evolution of a recombinant strain of Aspergillus niger. Journal of Biotechnology 75(1):1-10 (Sep. 24, 1999). DOI: 10.1016/S0168-1656(99)00123-6.
Martinet et al. Modification of the protein glycosylation pathway in the methylotrophic yeast *Pichia pastoris*. Biotechnology Letters 20(12):1171-1177 (Dec. 1998).
(Martinez, D. et al.) GenBank Accession No. EGR49218. Version No. EGR49218.1. glycoside hydrolase family 79 [Trichoderma reesei QM6a] (Jul. 25, 2016). Retrieved Dec. 9, 2019 at URL: https://www.ncbi.nlm.nih.gov/protein/EGR49218.1. 2 pages.
Martinez et al. Genome sequencing and analysis of the biomass-degrading fungus Trichoderma reesei (syn. Hypocrea jecorina). Nat Biotechnol 26(5):553-60 (May 2008). Epub May 4, 2008. doi: 10.1038/nbt1403.
Masuda et al. High yield secretion of the sweet-tasting protein lysozyme from the yeast *Pichia pastoris*. Protein Expression and Purification 39:35-42 (Nov. 2, 2004).
Mine et al. Reduction of antigenicity and allergenicity of genetically modified egg white allergen, ovomucoid third domain. Biochemical and Biophysical Research Communications 302:133-137 (2003).
Mizutani et al., Structural and Functional Characterization of Ovotransferrin Produced by Pichia pastoris, Biosci. Biotechnol. Biochem., 68(2): 376-383 (2004).
Muñoz et al. Cloning of the authentic bovine gene encoding pepsinogen a and its expression in microbial cells. Appl Environ Microbiol. May 2004;70(5):2588-95.doi: 10.1128/aem.70.5.2588-2595.2004.
Nakayama et al., Substrate specificity of $\alpha$-1,6-mannosyltransferase that initiates N-linked mannose outer chain elongation in *Saccharomyces cerevisiae*, FEBS Letters, 412(3): 547-550 (1997).
Nilsson et al., Intestinal MUC2 mucin supramolecular topology by packing and release resting on D3 domain assembly, J Mol Biol., 426(14): 2567-2579 (2014).
Palmieri et al. [Topical treatment of some dystrophic and inflammatory lesions of the skin and soft tissues.] Archivio per le Scienze Mediche, Oct.-Dec. 1977, 134(4):481-485.
Partow et al. Characterization of different promoters for designing a new expression vector in *Saccharomyces cerevisiae*. Yeast 27:955-964 (2010). Published online Jul. 12, 2010. DOI: 10.1002/yea.1806.
PCT/US2019/047521 International Search Report and Written Opinion dated Jan. 2, 2020.
Pepsin Activity, Food Chemicals Codex, 11th ed, Pharmacopeial Convention, pp. 1386-1387 (2018). Retrieved Jun. 9, 2020 at URL: https://app.knovel.com/web/view/khtml/print.v/rcid:kpFCCE0042/cid:kt011MEBGL/viewerType:khtml/?notes=off.
Proctor et al. The chemistry of lysozyme and its use as a food preservative and a pharmaceutical. Crit Rev Food Sci Nutr 26(4):359-95 (1988).
Rajamanickam et al. A novel bi-directional promoter system allows tunable recombinant protein production in Pichia pastoris. Microb Cell Fact 16:152 (2017). 7 pages. DOI 10.1186/s12934-017-0768-8.
Ramat et al. Protein Purification Using Expanded Bed Chromatography. Master of Science in Chemical Engineering Thesis. Worcester Polytechnic Institute Chemical Engineering Department, Winter 2004. 46 pages.
Ramon et al. Sorbitol co-feeding reduces metabolic burden caused by the overexpression of a Rhizopus oryzae lipase in Pichia pastoris. J Biotechnol. May 31, 2007;130(1):39-46.doi: 10.1016/j.jbiotec.2007.02.025. Epub Mar. 3, 2007.
Roth et al., Identification and Quantification of Protein Glycosylation, International Journal of Carbohydrate Chemistry, vol. 2012, Article ID 640923, 10 pages.
Rupa et al. Engineered recombinant ovomucoid third domain can modulate allergenic response in Balb/c mice model. Biochemical and Biophysical Research Communications 342:710-717 (2006).
Rupa et al. Genetically glycosylated ovomucoid third domain can modulate Immunoglobin E antibody production and cytokine response in BALB/c mice. Clinical and Experimental Allergy 37:918-928 (2007).
Rupa et al. Structural and immunological characterization of recombinant ovomucoid expressed in *Escherichia coli*. Biotechnology Letters 25:427-433 (2003).
Score report to Mcmillan et al per instant SEQ ID No. 1 (U.S. Pat. No. 8,227,436 issued Jul. 24, 2012 & published as 2008/0214485) (Year: 2012).
Score result for SEQ ID No. 3 for Berry et al (WO2015048339 & Silver et al WO2015048342 published Apr. 2, 2015) (Year: 2015).
Score result for SEQ ID No. 9 for Koentgen (WO2003102187-A1 published Dec. 11, 2003) (Year: 2003).
Teh et al., Expression and analysis of the glycosylation properties of recombinant human erythropoietin expressed in Pichia pastoris, Genetics and Molecular Biology, 34(3):464-470 (2011).
Thiex et al. Determination of Ash in Animal Feed: AOAC Official Method 942.05 Revisited. J AOAC Int Sep.-Oct. 2012 95(5):1392-7.
Towbin. Western Blotting. In Encyclopedia of Immunology Second Edition, P. J. Delves, ed., pp. 2503-2507 (1998).Elsevier Ltd.
U.S. Appl. No. 15/522,986 Office Action dated Aug. 8, 2019.
U.S. Appl. No. 15/522,986 Office Action dated Jan. 25, 2019.
U.S. Appl. No. 16/701,022 First Action Interview Pilot Program Pre-Interview Communication dated Apr. 28, 2020.
USP, Pepsin Activity. Ninth Edition of the Food Chemicals Codex (FCC 9). United States Pharmacopeia Convention, Rockville, MD, 2015e, pp. 1410-1411. Retrieved Jun. 9, 2020 at URL: https://app.knovel.com/web/view/khtml/print.v/rcid:kpFCCE0021/cid:kt00U53N01/viewerType:khtml/?notes=off.
Wang et al. Methanol-Independent Protein Expression by AOX1 Promoter with trans-Acting Elements Engineering and Glucose-Glycerol-Shift Induction in Pichia pastoris.Sci Rep. 2017; 7: 41850. Sci Rep. 2017; 7: 41850.Published online Feb. 2, 2017. doi: 10.1038/srep41850.
Wang et al., Proteomic analysis of fertilized egg white during early incubation, EuPA Open Proteomics, 2: 38-59 (2014).
Xiong et al. Effects of site-specific phosphorylation on the mechanical properties of ovalbumin-based hydrogels. International Journal of Biological Macromolecules 102:1286-1296 (2017). Available online May 8, 2017.
Yoshimasu et al. Soluble expression and purification of porcine pepsinogen from Pichia pastoris. Protein Expression and Purification 25(2):229-236 (2002).
Zhang et al. Fermentation strategies for recombinant protein expression in the methylotrophic yeast *Pichia pastoris*. Biotechnol Bioprocess Eng 5, 275-287 (2000). DOI: https://doi.org/10.1007/BF02942184.
Zocchi et al. Expression and purification of a recombinant avidin with a lowered isoelectric point in Pichia pastoris. Protein Expression and Purification 32:167-174 (2003).
Bagger et al. Hydration of a glycoprotein: relative water affinity of peptide and glycan moieties. Eur Biophys J. Apr. 2006;35(4):367-71.doi: 10.1007/s00249-005-0035-5. Epub Dec. 8, 2005.
Duan et al. Effect of oxidative modification on structural and foaming properties of egg white protein. Food Hydrocolloids, vol. 75, pp. 223-228, (Feb. 2018). Available online Aug. 13, 2017.
Goda et al. Effect of extra N-terminal residues on the stability and folding of human lysozyme expressed in Pichia pastoris. Protein Eng. Apr. 2000;13(4):299-307. doi: 10.1093/protein/13.4.299.
Ioannou et al. Human alpha-galactosidase A: glycosylation site 3 is essential for enzyme solubility. Biochem J. Jun. 15, 1998; 332(Pt 3): 789-797. doi: 10.1042/bj3320789.
Kallas et al. Enzymatic properties of native and deglycosylated hybrid aspen (Populus tremula $^x$ tremuloides) xyloglucan endotransglycosylase 16A expressed in Pichia pastoris. Biochem J.

(56) References Cited

OTHER PUBLICATIONS

Aug. 15, 2005; 390(Pt 1): 105-113. Published online Aug. 9, 2005. Prepublished online Apr. 1, 2005. doi: 10.1042/BJ20041749.

Karpusas et al. The structure of human interferon-beta: implications for activity. Cell Mol Life Sci. Nov. 1998;54(11): 1203-16.doi: 10.1007/s000180050248.

Malik et al. A novel fusion protein system for the production of native human pepsinogen in the bacterial periplasm. Protein Expr Purif. Jun. 2006;47(2): 662-71.doi: 10.1016/j.pep.2006.02.018. Epub Mar. 20, 2006.

Ovalbumin, Uptima. Interchim, France. Retrieved Nov. 12, 2020 at URL: http://www.interchim.fr/ft/R/R5851B.pdf. Published on Apr. 8, 2009 as per Google Search results. 2 pages.

PCT/US2020/041720 International Search Report and Written Opinion dated Oct. 8, 2020.

PCT/US2020/045519 International Search Report and Written Opinion dated Oct. 28, 2020.

PCT/US2020/047076 International Search Report and Written Opinion dated Oct. 20, 2020.

Pepsin. Sigma Aldrich Pepsin Product Sheet. Sigma Aldrich. Retrieved Aug. 24, 2020 from URL: https://www.sigmaaldrich.com/life-science/metabolomics/enzyme-explorer/analytical-enzymes/pepsin.html. 3 pages.

Peptide Solubility Guidelines. GenScript. 2 pages. Downloaded from GenScript website Dec. 10, 2020. Available on or before Dec. 10, 2020.

Shintani et al. Engineering of Porcine Pepsin: Alteration of S1 Substrate Specificity of Pepsin To Those of Fungal Aspartic Proteinases By Site-Directed Mutagenesis.J. Biol. Chem. 1997 272:18855-18861. doi:10.1074/jbc.272.30.18855.

Takao et al. Production of swine pepsinogen by protein-producing Bacillus brevis carrying swine pepsinogen cDNA. Appl Microbiol Biotechnol 30, 75-80 (1989). DOI: https://doi.org/10.1007/BF00256000.

Takegawa et al. Effect of deglycosylation of N-linked sugar chains on glucose oxidase from Aspergillus niger. Biochem Cell Biol. Aug. 1989;67(8): 460-4.doi: 10.1139/o89-072.

Tams et al. Adapting protein solubility by glycosylation. N-glycosylation mutants of Coprinus cinereus peroxidase in salt and organic solutions. Biochim Biophys Acta.Jul. 13, 1999;1432(2): 214-21.doi: 10.1016/s0167-4838(99)00103-x.

Tams, JW and Welinder, KG. Mild chemical deglycosylation of horseradish peroxidase yields a fully active, homogeneous enzyme. Anal Biochem. Jun. 10, 1995;228(1): 48-55.doi: 10.1006/abio.1995.1313.

U.S. Appl. No. 16/701,022 First Action Interview—Office Action dated Sep. 24, 2020.

U.S. Appl. No. 16/891,835 Office Action dated Sep. 4, 2020.

Verostek et al. Selective organic precipitation/extraction of released N-glycans following large-scale enzymatic deglycosylation of glycoproteins. Anal Biochem. Feb. 15, 2000;278(2):111-22. doi: 10.1006/abio.1999.4433.

Wang et al. High-level expression of endo-β-N-acetylglucosaminidase H from Streptomyces plicatus in Pichia pastoris and its application for the deglycosylation of glycoproteins. PLoS One. Mar. 17, 2015;10(3): e0120458.doi: 10.1371/journal.pone.0120458. eCollection 2015.

Wieser et al. Preparation of a Defined Gluten Hydrolysate for Diagnosis and Clinical Investigations of Wheat Hypersensitivities. Nutrients. Oct. 2018; 10(10): 1411. Published online Oct. 2, 2018. doi: 10.3390/nu10101411.14 pages.

Yamamoto et al. Characterization of *Bacillus* sp. endo-beta-N-acetylglucosaminidase and its application to deglycosylation of hen ovomucoid. Biotechnol Appl Biochem. Dec. 1998;28 (Pt 3):235-42.

\* cited by examiner

| pH of rOVD solution (4.23% w/v protein basis) | Absorbance of DI water | Absorbance of rOVD solution (4.23% w/v protein basis) | Photo of rOVD solution in DI water (4.23% w/v protein basis) |
|---|---|---|---|
| 4.11 | 0.037 | 0.047 | |

FIG. 2

| | Parameter | Pre processing | Post pasteurization | Post hot fill |
|---|---|---|---|---|
| rOVD solution (30% w/v protein based) in deionized water, at pH 4.06 | Absorbance at 600nm | 0.175 | 0.101 | 0.104 |
| | Photos | | | |
| rOVD solution (30% w/v protein based) at pH 6.3 | Absorbance at 600nm | 0.116 | 0.089 | 0.094 |
| | Photos | | | |

FIG. 3 rOVD in deionized water
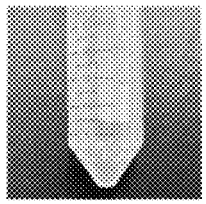 Room temperature
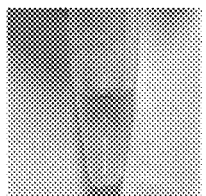 After pasteurization
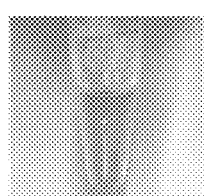 After hot fill
FIG. 4
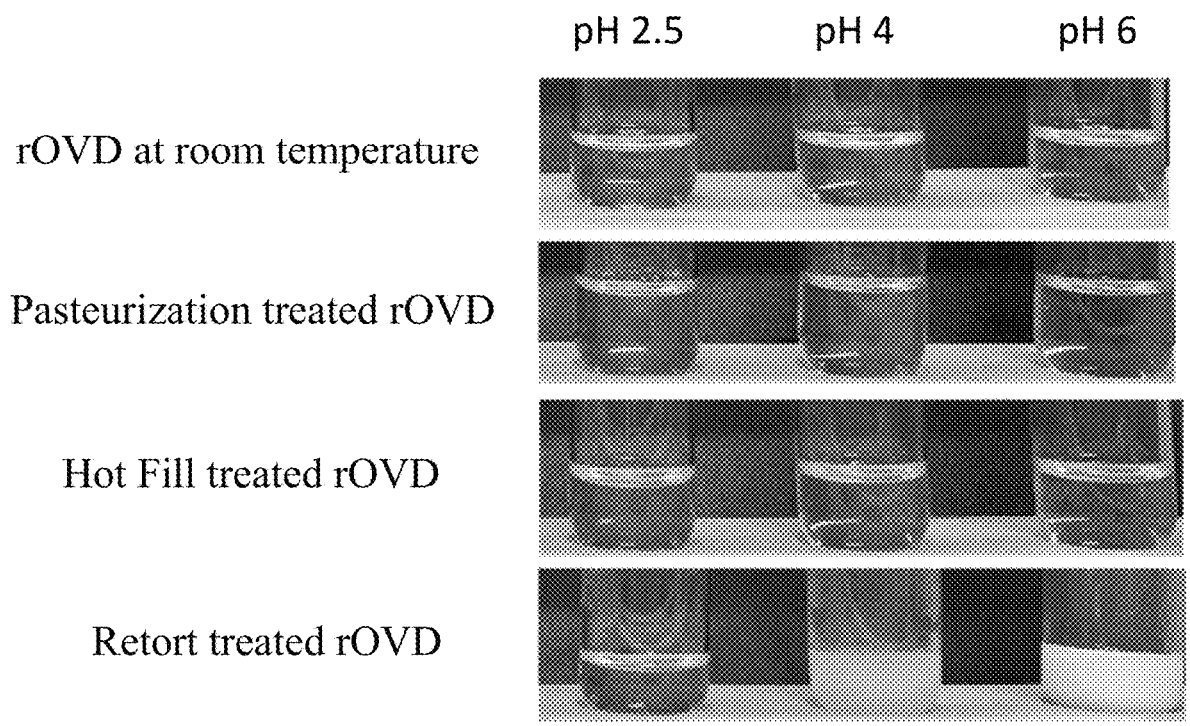
FIG. 5A

San Pellegrino®
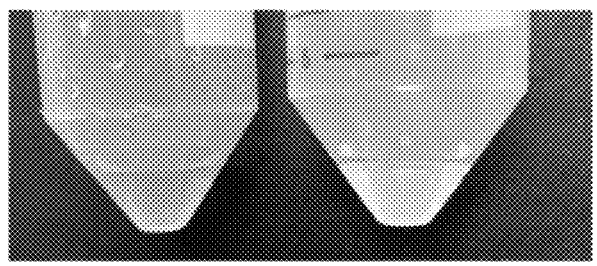
Diet Coke®
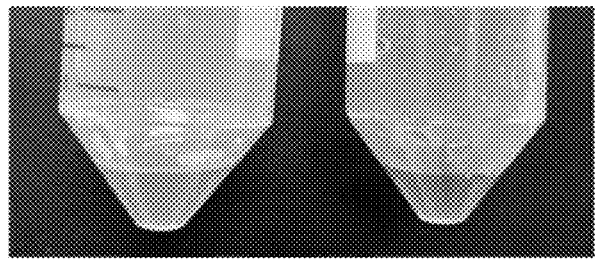
Gatorade™
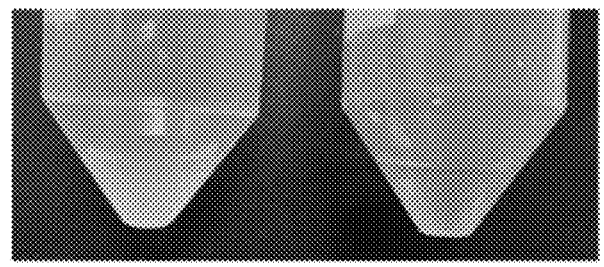
Red Bull™
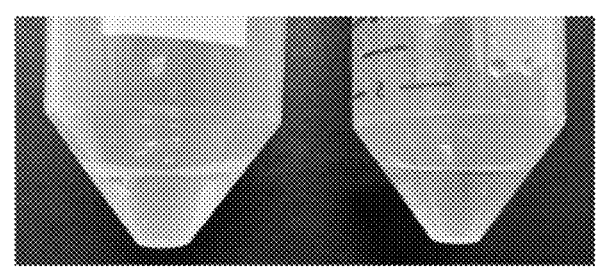
Pedialyte®
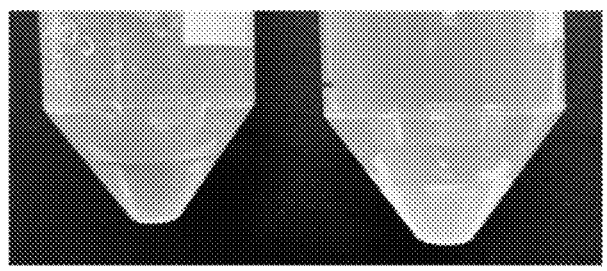
rOVD in Beverage No rOVD
FIG. 6A

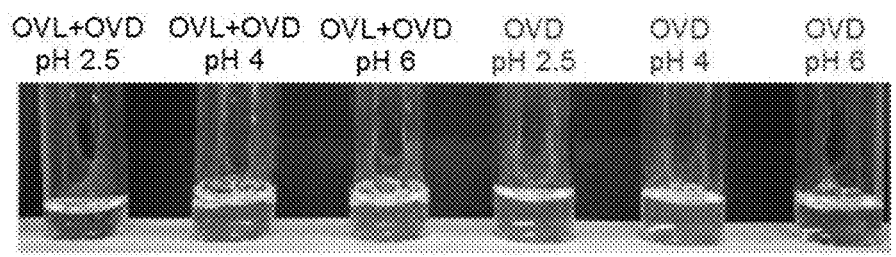
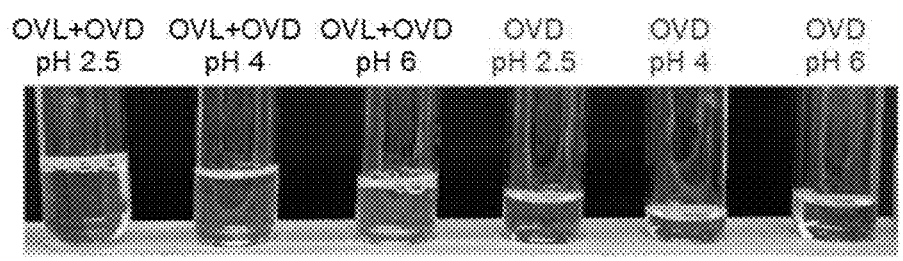
FIG. 7
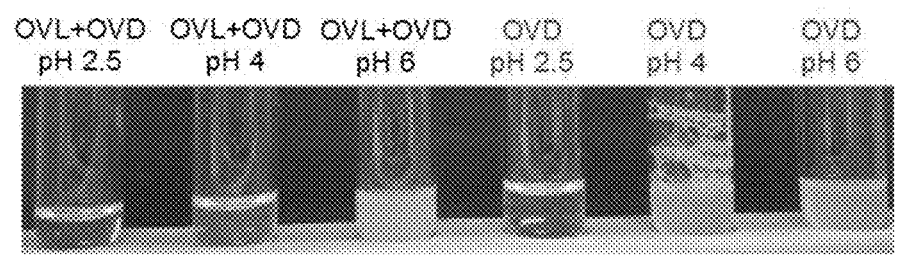
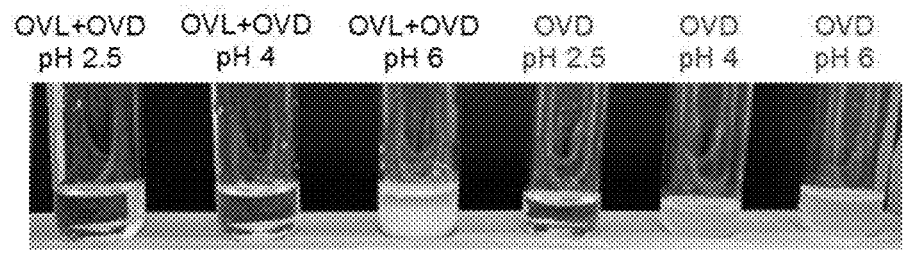
FIG. 8

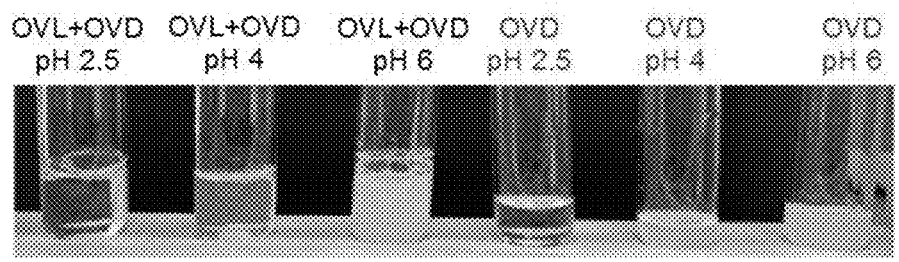
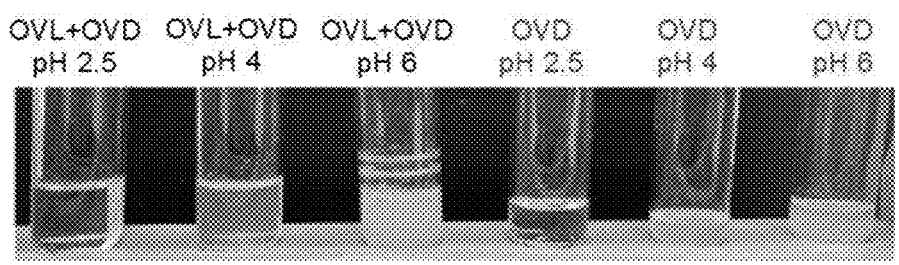
FIG. 9
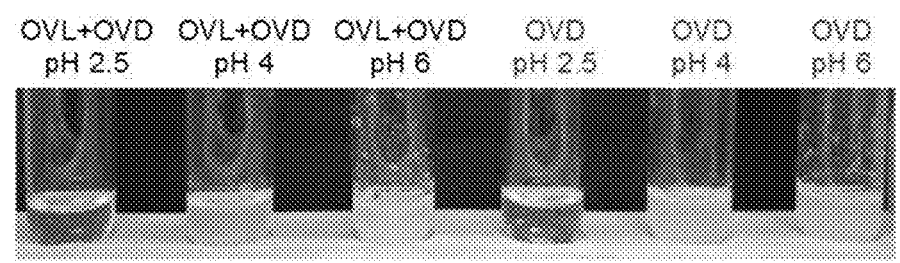
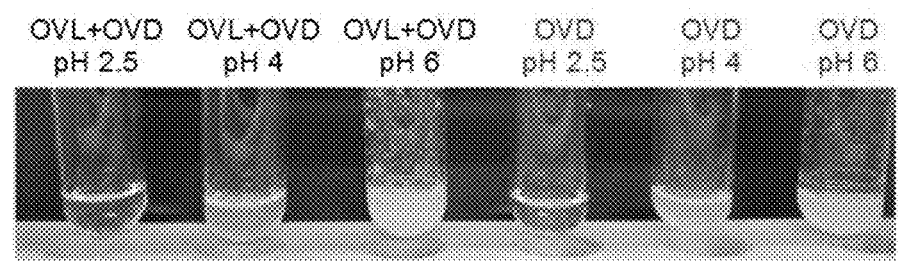
FIG. 10

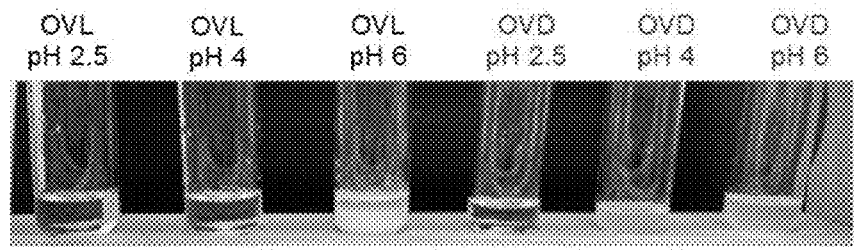
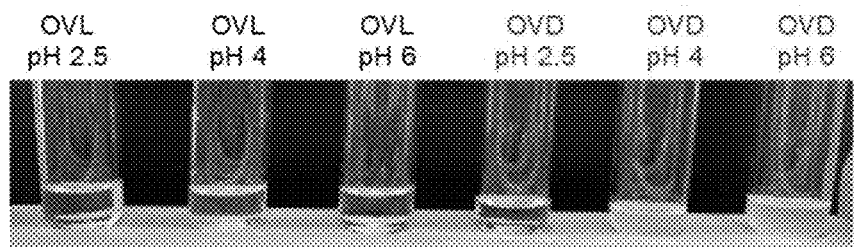
FIG. 11
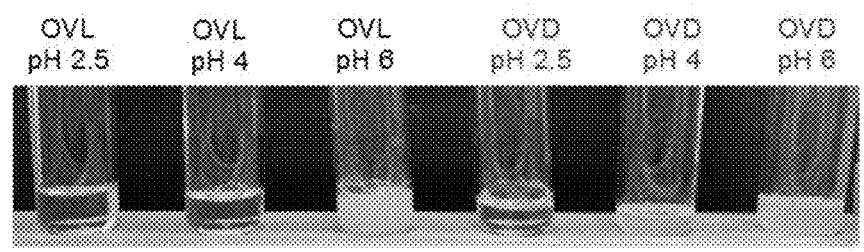
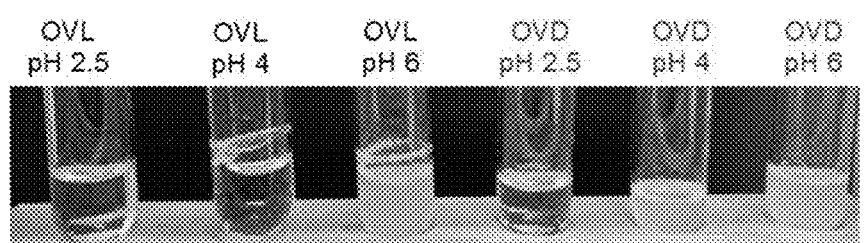
FIG. 12 rOVD-H concentration   30%   20%   10%   4.23% rOVD-T concentration   20%   10%   4.23

PROTEIN COMPOSITIONS AND CONSUMABLE PRODUCTS THEREOF

CROSS-REFERENCE TO RELATED APPLICATIONS

This application claims priority to International Patent Application Ser. No. PCT/US2020/041720, filed Jul. 10, 2020, which claims the benefit of U.S. Provisional Patent Application Ser. No. 62/873,154, filed Jul. 11, 2019 and U.S. Provisional Patent Application Ser. No. 62/873,159, filed Jul. 11, 2019; the entire contents of the aforementioned patent applications are incorporated herein by reference.

SEQUENCE LISTING

The instant application contains a Sequence Listing which has been submitted in ASCII format via EFS-Web and is hereby incorporated by reference in its entirety. Said ASCII copy, created on Jul. 10, 2020, is named 49160-714.601_ST25.txt and is 95,504 bytes in size.

BACKGROUND

Proteins are important dietary nutrients. They can serve as a fuel source or as sources of amino acids, including the essential amino acids that cannot be synthesized by the body. The daily recommended intake of protein for healthy adults is 10% to 35% of a person's total calorie needs, and currently the majority of protein intake for most humans is from animal-based sources. In addition, athletes and bodybuilders may rely upon increased protein consumption to build muscle mass and improve performance. With the world population growth and the coinciding growth in global food demand, there is a need to provide alternative sustainable, non-animal-based sources of proteins as useful source of protein for daily diet, dietary supplementation and sports nutrition.

SUMMARY

An aspect of the present disclosure is a composition comprising a recombinant ovomucoid protein (rOVD). The rOVD comprises at least one glycosylated asparagine residue and the rOVD is substantially devoid of N-linked mannosylation.

In some embodiments, each glycosylated asparagine comprises a single N-acetylglucosamine. The rOVD may comprise at least three glycosylated asparagine residues. In some cases, the rOVD is a secreted form of the rOVD protein. In various embodiments, the composition is a powder. The composition may have a protein content of at least 30% rOVD protein, at least 40% rOVD protein, at least 50% rOVD protein, at least 60% rOVD protein, at least 70% rOVD protein, at least 80% rOVD protein, at least 85% rOVD protein, at least 90% rOVD protein, or at least 95% rOVD protein on a weight/weight basis and/or a weight per total volume of composition basis. In some cases, the powder is capable of being dissolved in a liquid.

Another aspect of the present disclosure is a composition comprising a recombinant ovomucoid protein (rOVD). The composition is a powder formulated for human or animal consumption and the composition has a protein content of at least 70% rOVD protein, at least 80% rOVD protein, at least 85% rOVD protein, at least 90% rOVD protein, or at least 95% rOVD protein on a weight/weight basis and/or a weight per total volume of composition basis.

The powder may comprise less than 15%, 12%, 10%, 8%, 6%, 5%, 3%, 2% or 1% moisture on a weight/weight basis and/or a weight per total volume of composition basis. The powder may comprise less than 30%, 27%, 25%, 22%, 20%, 17%, 15%, 12%, 10%, 8%, 5%, 3% or 1% free carbohydrate content. In some embodiments, the powder is capable of being dissolved in a liquid.

In embodiments, a composition comprises one or more additional ingredients selected from the group consisting of a flavoring, a coloring agent, a sweetener, an amino acid, a protein, an acidulant, a preservative, and ash. In some cases, the composition comprises less than 5%, 4.5%, 4%, 3.5%, 3%, 2.5%, 2%, 1.5%, 1%, 0.75%, 0.5%, 0.25% or 0.1% ash. The amino acid may be selected from tryptophan, isoleucine, leucine, and valine, or a combination thereof.

Yet another aspect of the present disclosure is a composition comprising a recombinant ovomucoid protein (rOVD). The composition is in a solid form formulated for human or animal consumption, wherein the rOVD provides protein fortification to the composition and at least one additional feature selected from the group consisting of mouthfeel, texture, hardness, stability to heat treatment, and stability to pH.

In various embodiments, the rOVD comprises at least one asparagine residue linked to N-acetyl glucosamine and the rOVD is substantially devoid of N-linked mannosylation. The concentration of rOVD may be greater than about 5%, about 10%, about 15%, about 20%, or about 25% on a weight/weight basis and/or a weight per total volume of composition basis and/or a weight per total volume of composition basis. In some cases, the rOVD does not substantially alter the visible appearance or mouthfeel of the solid consumable composition as compared to a solid consumable composition lacking rOVD; the rOVD does not substantially alter the visible appearance or mouthfeel of the solid consumable composition as compared to a solid consumable composition containing whey protein, soy protein, or pea protein at the same concentration as the rOVD; the rOVD does not substantially affect a sensory rating for odor and/or for taste as compared to a solid consumable composition lacking rOVD; and/or the rOVD does not substantially affect a sensory rating for odor and/or for taste as compared to a comparable composition containing whey protein, soy protein, or pea protein at the same concentration as the rOVD. In some embodiments, the solid consumable composition is a snack bar, a protein bar, a nutrition bar, an energy bar, or a protein supplement. In some cases, the solid consumable composition comprises one or more additional ingredients selected from the group consisting of a flavoring, a coloring agent, a sweetener, an amino acid, a protein, an acidulant, a preservative, and ash.

In an aspect, the present disclosure provides a composition comprising a recombinant ovomucoid protein (rOVD). The composition is a liquid formulated for human or animal consumption, wherein the rOVD provides protein fortification to the composition and at least one additional feature selected from the group consisting of solubility, mouthfeel, stability to heat treatment, and stability to pH.

In some cases, the composition has a protein content comprising at least 15% rOVD, at least 20% rOVD protein, at least 30% rOVD protein, or at least 40% rOVD protein on a weight/weight basis and/or a weight per total volume of composition basis. The composition may have a protein content comprising at least 5% rOVD, and in which the liquid consumable composition is substantially optically clear. In embodiments, the composition has an optical clarity greater than a comparable composition containing whey protein, soy protein, or pea protein at the same concentration as the rOVD. In some cases, the rOVD does not substantially alter the visible appearance or mouthfeel of the liquid consumable composition as compared to a liquid consumable composition lacking rOVD; the rOVD does not substantially alter the visible appearance or mouthfeel of the liquid consumable composition as compared to a comparable composition containing whey protein, soy protein, or pea protein at the same concentration as the rOVD; the rOVD does not substantially affect a sensory rating for odor and/or for taste as compared to a liquid consumable composition lacking rOVD; and/or the rOVD does not substantially affect a sensory rating for odor and/or for taste as compared to a comparable composition containing whey protein, soy protein, or pea protein at the same concentration as the rOVD. The rOVD may remain substantially soluble after the liquid consumable composition has been heated to a temperature of between about 72° C. and about 121° C. In some cases, the rOVD has a greater solubility, optical clarity or both solubility and optical clarity in the liquid following a heat treatment than the stability of whey protein, soy protein, or pea protein at the same concentration as the rOVD. In some embodiments, the heat treatment comprises exposure of the liquid to a temperature of between about 72° C. and about 121° C. The rOVD may have a solubility in the liquid greater than the solubility of whey protein, soy protein, or pea protein at the same concentration as the rOVD. In some cases, the liquid consumable composition has a pH of between about 2.0 and about 8.0.

In some embodiments, a solid form formulated for human or animal consumption or a liquid formulated for human or animal consumption may comprise one or more additional ingredients selected from the group consisting of a flavoring, a coloring agent, a sweetener, an amino acid, a protein, an acidulant and a preservative. In various embodiments, the amino acid is selected from tryptophan, isoleucine, leucine, and valine, or a combination thereof. In some cases, the protein is a lysozyme protein, e.g., an egg white lysozyme (OVL). The ratio of rOVD to OVL may between about 60% rOVD:40% OVL and about 82% rOVD:18% OVL. The lysozyme may be a recombinant lysozyme protein. In some cases, the protein and/or the amino acid provides an improved amino acid balance to the solid form or the liquid. In embodiments, a protein digestibility corrected amino acid score (PDCAAS) is equal to or greater than about 0.75, e.g., greater than or equal to about 0.8, 0.85, 0.90, 0.95 or the PDCAAS is about or is 1.0. The liquid consumable composition may comprise rOVD and OVL and the proteins are soluble and composition is optically clear.

In some cases, the liquid consumable composition is a beverage selected from the group consisting of a juice, a broth, a soup, a soda, a soft drink, a flavored water, a protein water, a fortified water, a carbonated water, a nutritional drink, an energy drink, a sports drink, a recovery drink, a heated drink, a coffee-based drink, a tea-based drink, a plant-based milk, a milk based drink, a non-dairy, plant based mild drink, infant formula drink, a meal replacement drink. In some embodiments, the beverage comprises carbonation.

A liquid consumable composition may be a syrup comprising between 20% rOVD protein and at least 60% rOVD protein on a weight/weight basis and/or a weight per total volume of composition basis.

In some cases, the liquid consumable composition is an emulsion, e.g., a sauce, a gravy, or a salad dressing.

In another aspect, the present disclosure provides a composition comprising a recombinant ovomucoid protein (rOVD). The composition is in a semi-solid form formulated for human or animal consumption, in which the rOVD provides at least one additional feature selected from the group consisting of mouthfeel, texture, hardness, stability to heat treatment, and stability to pH.

In various embodiments, the semi-solid consumable composition is a gummy, candy, jelly, syrup, gel, a gelled preparation. In some cases, the rOVD does not substantially alter the visible appearance or mouthfeel of the semi-solid consumable composition as compared to a semi-solid consumable composition lacking rOVD; the rOVD does not substantially alter the visible appearance or mouthfeel of the semi-solid consumable composition as compared to a semi-solid consumable composition containing whey protein, soy protein, or pea protein at the same concentration as the rOVD; the rOVD does not substantially affect a sensory rating for odor and/or for taste as compared to a semi-solid consumable composition lacking rOVD; and/or the rOVD does not substantially affect a sensory rating for odor and/or for taste as compared to a comparable composition containing whey protein, soy protein, or pea protein at the same concentration as the rOVD. The semi-solid consumable composition may have an optical clarity greater than a comparable composition containing whey protein, soy protein, or pea protein at the same concentration as the rOVD.

The semi-solid consumable composition may comprise one or more additional ingredients selected from the group consisting of a flavoring, a coloring agent, a sweetener, an amino acid, a protein, an acidulant, and a preservative. The protein and/or the amino acid may provide an improved amino acid balance to the semi-solid consumable composition. In some cases, the amino acid is selected from tryptophan, isoleucine, leucine, and valine, or a combination thereof. In some embodiments, the protein and/or the amino acid provides an improved amino acid balance to the semi-solid consumable composition. The protein and/or the amino acid may provide an improved amino acid balance to the semi-solid consumable composition. In some cases, the amino acid is selected from tryptophan, isoleucine, leucine, and valine, or a combination thereof. In embodiments, the protein is a lysozyme protein, e.g., the lysozyme protein is an egg white lysozyme (OVL). The ratio of rOVD to OVL may be between about 60% rOVD:40% OVL and about 82% rOVD:18% OVL. The lysozyme may be a recombinant lysozyme protein. In various embodiments, a protein digestibility corrected amino acid score (PDCAAS) is equal to or greater than about 0.75, 0.8, 0.85, 0.90, 0.95 or the PDCAAS is about or is 1.0.

In some cases, the rOVD comprises an rOVD that has been exposed to an oxidizing agent or an oxygen-generating agent. In various embodiments, the oxygen-generating agent is hydrogen peroxide, sodium percarbonate, bubbled oxygen, activated chlorine dioxide, or ozone.

In some cases, the rOVD comprises an amino acid sequence that is naturally found in an avian species, e.g., chicken, quail, turkey, turkey vulture, hummingbird, duck, ostrich, goose, gull, guineafowl, pheasant, or emu, and any combination thereof.

The rOVD may comprise an amino acid sequence of one of SEQ ID No. 1-44 or an amino acid sequence having at least 85% sequence identity with one of SEQ ID No. 1-44.

In embodiments, the rOVD is substantially a full-length rOVD amino acid sequence.

In some cases, the rOVD provides protein fortification to the composition.

In some embodiments, the rOVD is produced by a microbial host cell, e.g., In some cases, the microbial host cell is a yeast, a filamentous fungus, or a bacterium. The microbial host cell may be a *Pichia* species, a *Saccharomyces* species, a *Trichoderma* species, a *Pseudomonas* species or an *E. coli* species. The microbial host cell may be *Pichia pastoris* or *Komagataella phaffii*.

Another aspect is a consumable composition comprising a recombinant ovomucoid protein (rOVD). The rOVD provides protein fortification to the composition; in which the rOVD provides a solubility that is comparable or higher than a native ovomucoid protein.

An aspect of the present disclosure is a consumable powder protein composition comprising a recombinant ovomucoid protein (rOVD). The protein content of the composition is greater than 70%; in which the composition comprises less than 2% ash, less than 20% carbohydrates, and less than 1% fat by acid hydrolysis on a weight/weight basis and/or a weight per total volume of composition basis.

Another aspect of the present disclosure is a consumable composition comprising a recombinant ovomucoid protein (rOVD). The composition has a protein content comprising at least 15% rOVD protein on a weight/weight basis and/or a weight per total volume of composition basis.

In an aspect, the present disclosure provides a consumable composition comprising a recombinant ovomucoid protein (rOVD). The rOVD provides protein fortification to the composition; in which the rOVD provides a water retention capacity higher than a native ovomucoid protein.

Yet another aspect of the present disclosure is a beverage composition comprising a recombinant ovomucoid protein (rOVD) and at least one consumable liquid, in which the rOVD is substantially soluble in the composition, in which the beverage composition is substantially optically clear, and in which the concentration of rOVD is greater than about 5% on a weight/weight basis and/or a weight per total volume of composition basis. The beverage is selected from the group consisting of a juice, a broth, a soup, a soda, a soft drink, a flavored water, a protein water, a fortified water, a carbonated water, a nutritional drink, an energy drink, a sports drink, a recovery drink, a heated drink, a coffee-based drink, a tea-based drink, a plant-based milk, a milk based drink, a non-dairy, plant based mild drink, infant formula drink, a meal replacement drink. The beverage may comprise carbonation.

In an aspect, the present disclosure provides a method of preparing a consumable food preparation. The method comprising the steps of: providing a recombinant OVD (rOVD) produced by a microbial host; in which the rOVD comprises N-linked glycosylation and in which rOVD is substantially devoid of N-linked mannosylation; producing a preparation by combining or mixing the rOVD with at least one consumable ingredient; in which the rOVD provides protein fortification to the composition and at least one additional feature selected from the group consisting of solubility, optical clarity, mouthfeel, texture, hardness, stability to heat treatment and stability to pH.

In various embodiments, the rOVD comprises one or more glycosylated asparagine residues, in which each glycosylated asparagine residue comprises a single N-acetylglucosamine. In some cases, the rOVD is present in the consumable food preparation in or in about 1%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% or 40% on a weight/weight basis and/or a weight per total volume of the preparation.

The method may further comprise heat-treating the preparation, e.g., exposing the preparation to a temperature between about 72° C. and about 121° C. The heat-treating may comprise hot fill, pasteurization, retort, boiling, baking, broiling or grilling. In embodiments, the preparation has a pH between about 2 and about 6.

In some cases, the method further comprises expressing rOVD protein in the microbial host, e.g., a yeast, a filamentous fungus, or a bacterium. In some embodiments, the microbial host is a *pichia* species, a *saccharomyces* species, a *Trichoderma* species, a *pseudomonas* species or an *E. coli* species. In some cases, the microbial host is *Pichia pastoris* or *Komagataella phaffii*.

In some embodiments, the method further comprises expressing an enzyme in the microbial host having an activity to remove a glycan by cleaving within a chitobiose core of high mannose and hybrid oligosaccharides on an N-linked glycoprotein. In various embodiments, the enzyme comprises EndoH, an OCH1-EndoH fusion or an active fragment of EndoH.

In some cases, the rOVD is secreted from the microbial host, and in which the method further comprises isolating the secreted rOVD prior to combining or mixing the rOVD with the at least one consumable ingredient.

The method may further comprise separating the secreted rOVD from the microbial host and exposing the rOVD to an oxidizing agent or an oxygen-generating agent, e.g., hydrogen peroxide, sodium percarbonate, activated chlorine dioxide, bubbled oxygen, or ozone.

In some cases, the method further comprises drying, powdering, and/or spray-drying the rOVD.

In various embodiments, preparation is suitable for human consumption and/or for animal consumption.

An aspect of the present disclosure is a consumable composition produced by a herein-disclosed method.

Another aspect of the present disclosure is a recombinant ovomucoid (rOVD) protein comprising N-linked glycosylation, in which the N-linked glycosylation comprises N-acetyl glucosamine and substantially lacks mannose residues.

In some cases, the rOVD further comprises O-linked glycosylation. At least one asparagine residue of the OVD is glycosylated and has a single N-acetyl glucosamine residue. In embodiments, at least three asparagine residues of rOVD have a single N-acetyl glucosamine residue. The rOVD protein may comprise an rOVD that has been exposed to an oxidizing agent or an oxygen-generating agent, e.g., hydrogen peroxide, sodium percarbonate, bubbled oxygen, activated chlorine dioxide, or ozone.

Yet another aspect is a composition comprising the rOVD protein according to any herein disclosed aspect or embodiment.

In some embodiments, the composition is in powdered form and in which the protein content of the composition is about 70% or greater on a weight/weight basis and/or a weight per total volume of composition basis. In some cases, the rOVD protein is present in the composition at about 80% or greater on a weight/weight basis and/or a weight per total volume of composition basis.

In an aspect, the present disclosure provides a method of making an rOVD protein. The method comprising: producing rOVD protein in a eukaryotic host cell, in which the rOVD protein is secreted from the host cell and in which the host cell expresses an enzyme having an activity that removes mannose residues from N-acetyl glucosamine linkage; separating the rOVD protein from the host cell; exposing the rOVD protein to an oxidizing agent or an oxygen-generating agent; and separating rOVD from the oxidizing agent or oxygen-generating agent.

In some embodiments, the enzyme comprises EndoH, an OCH1-EndoH fusion, or an active fragment of EndoH. In some cases, the oxidizing agent or oxygen-generating agent comprises hydrogen peroxide, sodium percarbonate, bubbled oxygen, activated chlorine dioxide, or ozone. In some embodiments, the host cell is a yeast or fungal cell.

In some cases, the host cell is a *Pichia* sp.

In any of the herein disclosed methods or compositions, the rOVD may be derived from an avian species.

In any of the herein disclosed methods or compositions, the rOVD may comprise an amino acid sequence of a chicken OVD, a goose OVD protein, a hummingbird OVD, or a turkey vulture OVD.

In any of the herein disclosed methods or compositions, the rOVD may comprise an amino acid sequence selected from the group consisting of SEQ ID No. 1-44 and an amino acid sequence having at least 85% sequence identity with SEQ ID No. 1-44.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. The drawings and description are to be regarded as illustrative in nature, and not as restrictive. Any description herein concerning a specific composition and/or method apply to and may be used for any other specific composition and/or method as disclosed herein. Additionally, any composition disclosed herein is applicable to any herein-disclosed method. In other words, any aspect or embodiment described herein can be combined with any other aspect or embodiment as disclosed herein.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 2 illustrates rOVD solution properties with 4.23% w/v rOVD.

FIG. 3 illustrates rOVD solution clarity at about pH 4 and about pH 6 with 30% w/v rOVD after different heat treatments, measured using absorbance at 600 nm.

FIG. 4 illustrates rOVD solution clarity after different heat treatments with 30% w/v rOVD in deionized water.

FIG. 5A illustrates rOVD solution (9% w/v) appearance at pH 2.5, 4, and 6 after different heat treatment conditions.

FIG. 6A illustrates rOVD solubility in different beverages.

FIG. 7 illustrates, left to right, a comparison of samples at room temperature: OVL+OVD with OVD control at pH 2.5, 4, 6.

FIG. 8 illustrates, left to right, a comparison of Pasteurized (72° C.) samples: OVL+OVD with OVD control at pH 2.5, 4, 6.

FIG. 9 illustrates, left to right, a comparison of Hot Fill (85° C.) samples of OVL+OVD with OVD control at pH 2.5, 4, 6.

FIG. 10 illustrates, left to right, a comparison of retorted (121° C.) samples of OVL+OVD with OVD control at pH 2.5, 4, 6.

FIG. 11 illustrates, left to right, a comparison of Pasteurized (72° C.) samples of OVL control with OVD control at pH 2.5, 4, 6.

FIG. 12 illustrates, left to right, a comparison of Hot Fill (85° C.) samples of OVL control with OVD control at pH 2.5, 4, 6.

FIG. 17A: solution at time 0 hours and FIG. 17B: after 48 hours storage at 4° C.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Provided herein are compositions and methods of making compositions for non-animal-based sources of proteins as useful source of consumable protein for ingestion by an animal, including a human, such as for daily diet, dietary supplementation, consumer food and beverage, and nutrition.

Provided herein are consumable compositions comprising ovomucoid (OVD). Such consumable compositions can be used in a food product, drink product, nutraceutical, pharmaceutical, cosmetic, or as an ingredient for a final product. In embodiments herein, the consumable composition is in a liquid form or a semi-solid form. In embodiments herein, the consumable composition is provided in a powdered form; this powder may be used to produce a liquid, solid, or semi-solid consumable composition. Preferably, the OVD in such consumable compositions is made recombinantly, and may be referred to herein as a recombinant OVD (rOVD).

Unless indicated otherwise, the term OVD includes both native OVD (nOVD) and rOVD. The nOVD or rOVD in the consumable compositions herein is provided in concentrations that both increase the protein content of the consumable composition and also maintain one or more additional characteristics such as high clarity, high solubility, reduced turbidity, or substantial sensory neutrality.

The use of rOVD in any of the consumable compositions herein allows for a non-animal-based source of protein, while providing additional features such as solubility, clarity, hardness, texture, mouthfeel, compatibility with heat treatment, compatibility with pH ranges and maintaining a consumer-favorable sensory profile. Various embodiments of such compositions, methods of making them, and methods of using them are provided herein.

In some embodiments, the compositions and methods for making compositions herein increase the protein content of a consumable, and also provide additional features such as compatibility with other ingredients (such as, for example, compatibility with gluten, vitamins, minerals, and carbonation), coloration, smell, taste and compatibility with food and beverage preparation and/or storage conditions.

Figure 1A:
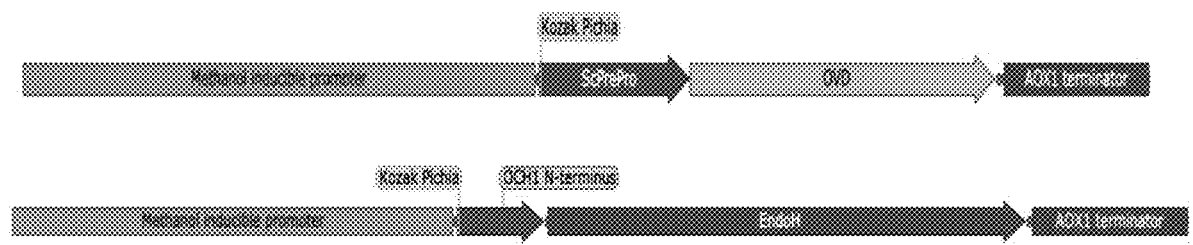
FIG. 1A illustrates the vector constructs used for the expression of rOVD.
Figure 1B:
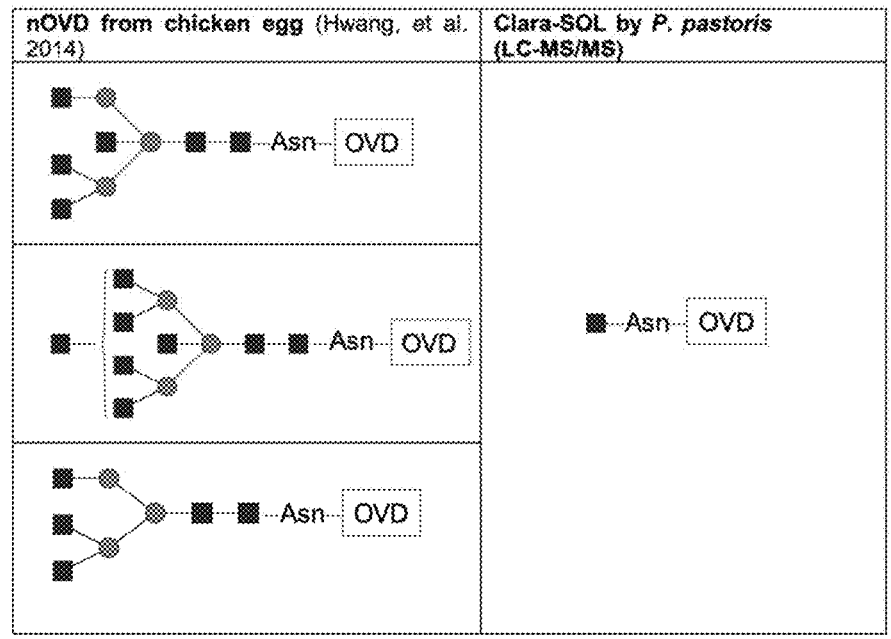
FIG. 1B illustrates a comparison in the glycosylation pattern of native ovomucoid and a recombinant ovomucoid produced in *P. pastoris* and according to the present disclosure. Shown is a lack of the complex branched glycosylation (including a lack of mannose residues) on the recombinant ovomucoid when produced in a strain of *P. pastoris* comprising endoglycosidases.
Figure 1C:
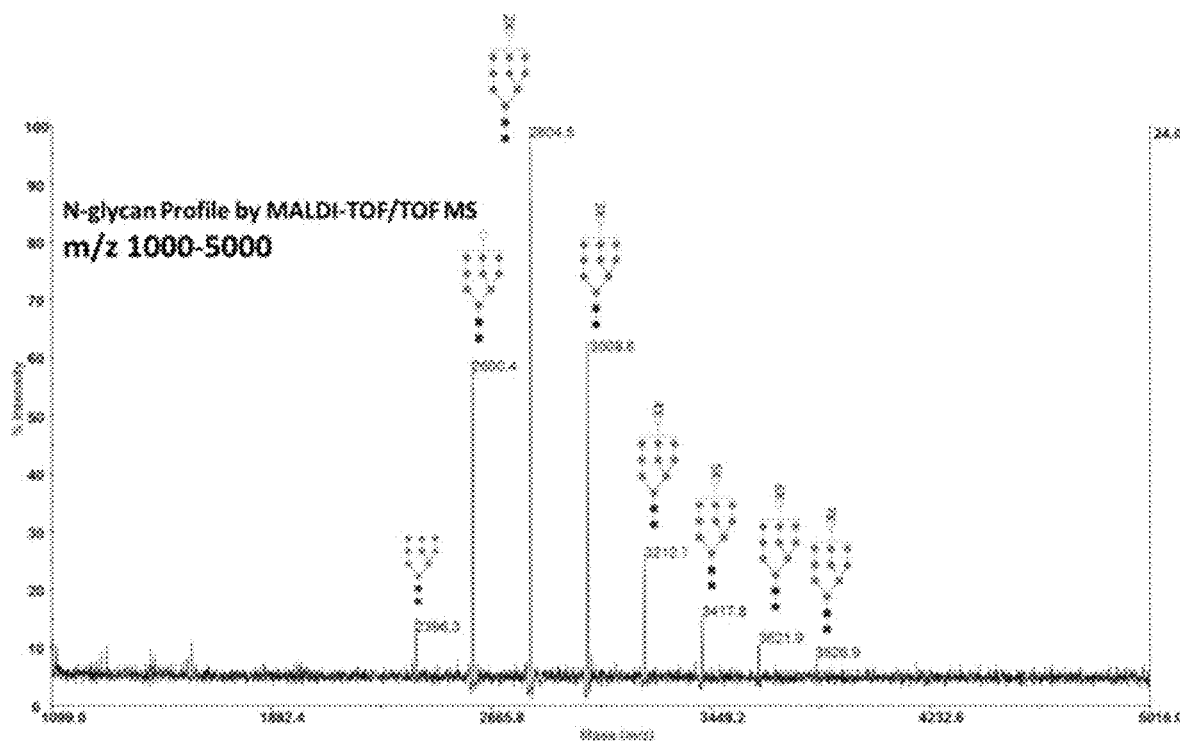
FIG. 1C illustrates the glycosylation patterns of the recombinant OVD produced by *P. pastoris* without an endoglycosidase treatment. rOVD thus produced have complex branched glycosylation patterns.

Native ovomucoid (nOVD), such as isolated from a chicken or other avian egg, has a highly complex branched form of glycosylation. The glycosylation pattern comprises N-linked glycan structures such as N-acetylglucosamine units and N-linked mannose units. See, e.g., FIG. 1B (left-hand column). In some cases, the rOVD for use in a herein disclosed consumable composition and produced using the methods described herein has a glycosylation pattern which is different than the glycosylation pattern of nOVD. For example, when rOVD is produced in a *Pichia* sp., the protein may be highly glycosylated. FIG. 1C illustrates the glycosylation patterns of rOVD produced by *P. pastoris*, showing a complex branched glycosylation pattern. In some embodiments of the compositions and methods herein, rOVD is treated such that the glycosylation pattern is modified from that of nOVD and also modified as compared to rOVD produced by a *Pichia* sp. without such treatment. In some cases, the rOVD has no glycosylation. In other cases, the rOVD has reduced glycosylation. In some cases, the rOVD is modified by N-acetylglucosamine at one or more asparagine residues of the protein and lacks or is substantially devoid of N-linked mannosylation. See, e.g., FIG. 1B (right hand column). The changes in glycosylation described herein may lead to an increase in the solubility and clarity of rOVD as compared to other forms of protein such as whey proteins, soy proteins, pea proteins, and nOVD. The modifications in glycosylation of rOVD may lead to a change in the nitrogen to carbon ratio of the protein, such that reducing or removing substantially all of the mannose residues, the nitrogen to carbon ratio is increased (such as compared to nOVD or to rOVD produced without the modification to the glycosylation pattern).

In some embodiments, the composition is a consumable food product. In some embodiments, the consumable food product is a finished product. In some embodiments, the composition is an ingredient of a finished product, e.g., a powder comprising rOVD or consisting essentially of rOVD.

As used herein, the term "consumable food composition" refers to a composition, which comprises an isolated protein and may be consumed by an animal, including but not limited to humans and other mammals. Consumable food compositions include food products, beverage products, dietary supplements, food additives, and nutraceuticals, as non-limiting examples.

Consumable food compositions also include compositions as an ingredient of a food or beverage or a product ingested as part of an animal diet.

Since the rOVD of the present disclosure is not obtained from an animal source, a consumable composition comprising the rOVD is considered vegetarian and/or vegan.

As used herein, a "finished product" refers to a consumable food composition directed to or suitable itself as a food or beverage for animal consumption. As used herein, an "ingredient" or "component" in reference to a consumable food composition refers to a composition that is used with other ingredient(s) or component(s) to create a finished product.

Compositions with rOVD

Provided herein are consumable food compositions and methods of making such compositions that increase the protein content of a consumable food composition through the addition of a recombinant ovomucoid protein (rOVD). In some embodiments, rOVD is added to a consumable food composition to increase the protein content, such as for added nutrition. In some embodiments, rOVD is present in the consumable food composition between about 1% and about 40% on a weight per total weight (w/w) and/or weight per total volume (w/v) of composition basis. For example, in a composition of 100 ml, rOVD is present at 30 g and the rOVD is thus at a 30% concentration. In some embodiments, the concentration of rOVD is or is about 1%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% or 40% on a w/w and/or w/v of composition basis. In some embodiments, the rOVD is present at a concentration of or of about 1-5%, 5-10%, 10-15%, 15-20%, 20-25%, 25-30% or rOVD is present concentration greater than 5%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% or 40% w/w and/or w/v.

A consumable product can include one or more other proteins, such as a non-OVD protein or a non-recombinant protein. The rOVD can increase amount of protein content in a consumable product, and/or it can also increase solubility of the one or more other proteins. For example, the consumable composition can include a whey protein, a pea protein, a soy protein, an almond protein, an oat protein, a flax seed protein, a vegetable protein, or an egg-white protein. In some cases, the one or more other proteins can comprise OVD having an amino acid sequence naturally found in an avian or a reptile.

In some embodiments, the compositions and methods for making compositions increase the protein content, and provide solubility of the protein in the composition, as well as maintain or not substantially reduce the clarity of the composition. In some embodiments, the compositions and methods for making compositions increase the protein content, and provide solubility and maintain clarity, while not adversely affecting the stability, or one or more sensory qualities of the composition.

In some embodiments, the consumable food compositions and methods for making consumable food compositions comprise rOVD and the rOVD increases the protein content of the consumable food composition and the rOVD is substantially soluble in the consumable food composition. The consumable food composition may be a finished product or an ingredient for making a finished product, e.g., a powdered rOVD composition.

rOVD protein may be used on its own or in combination with other components to form a composition. In some embodiments, a composition may contain about or at least about 10%, 20%, 30%, 40%, 50%, 55%, 60%, 65%, 70%, 75%, 80%, 85%, 90%, 95%, 96%, 97%, 98%, or 99% protein, e.g., rOVD, by weight per total weight (w/w) and/or weight per total volume (w/v). In some cases, a composition described herein may contain up to about 10%, 20%, 30%, 40%, 50%, 55%, 60%, 65%, 70%, 75%, 80%, 85%, 90%, 95%, 96%, 97%, 98%, or 99% protein, e.g., rOVD, by w/w or w/v.

In some embodiments, a composition described herein contains total protein at a concentration of about or at least 5, 6, 7, 8, 9, 10, 11, 12, 13, 13.2, 14, 15, 16, 17, 18, 19, 20, 21, 22, 23, 24, 25, 30, 35, 40, 45, 50, 55, 60, 65, 70, or 75 g total protein per 100 mL liquid (e.g., water). In some cases, a composition described herein contains total protein at a concentration of about or at least 5, 6, 7, 8, 9, 10, 11, 12, 13, 13.2, 14, 15, 16, 17, 18, 19, 20, 21, 22, 23, 24, 25, 30, 35, 40, 45, 50, 55, 60, 65, 70, 75, 80, 85, 90, 95, or 100 g total protein per 100 g composition (e.g., powder).

In some embodiments, a composition described herein contains total protein at a concentration of about or at least 0.1, 0.2, 0.3, 0.5, 0.7, 1.0, 1.2, 1.5, 1.7, 2.0, 2.2, 2.5, 2.7, 3.0, 3.2, 3.5, 3.7, 4.0, 4.2, 4.5, 4.7 or 5 g total protein per 100 mL liquid (e.g., water). In some cases, a composition described herein contains total protein at a concentration of about or at least 0.1, 0.2, 0.3, 0.5, 0.7, 1.0, 1.2, 1.5, 1.7, 2.0, 2.2, 2.5, 2.7, 3.0, 3.2, 3.5, 3.7, 4.0, 4.2, 4.5, 4.7 or 5 g total protein per 100 g composition (e.g., powder).

In some embodiments, the rOVD consumable composition is a liquid composition. In such cases, the concentration of rOVD in the liquid composition may be between 0.1% to 40%. The concentration of rOVD in the liquid composition may be at least 0.1%. The concentration of rOVD in the liquid composition may be at most 40%. The concentration of rOVD in the liquid composition may be from 0.1% to 1%, 0.1% to 5%, 0.1% to 10%, 0.1% to 15%, 0.1% to 20%, 0.1% to 25%, 0.1% to 30%, 0.1% to 35%, 0.1% to 40%, 1% to 5%, 1% to 10%, 1% to 15%, 1% to 20%, 1% to 25%, 1% to 30%, 1% to 35%, 1% to 40%, 5% to 10%, 5% to 15%, 5% to 20%, 5% to 25%, 5% to 30%, 5% to 35%, 5% to 40%, 10% to 15%, 10% to 20%, 10% to 25%, 10% to 30%, 10% to 35%, 10% to 40%, 15% to 20%, 15% to 25%, 15% to 30%, 15% to 35%, 15% to 40%, 20% to 25%, 20% to 30%, 20% to 35%, 20% to 40%, 25% to 30%, 25% to 35%, 25% to 40%, 30% to 35%, 30% to 40%, or 35% to 40% in weight per total volume (w/v). The concentration of rOVD in the liquid composition may be about 0.1%, 1%, 5%, 10%, 15%, 20%, 25%, 30%, 35%, or 40% w/v. The concentration of rOVD in the liquid composition may be at least 0.1%, 1%, 5%, 10%, 15%, 20%, 25%, 30% or 35% w/v. The concentration of rOVD in the liquid composition may be at most 1%, 5%, 10%, 15%, 20%, 25%, 30%, 35% or 40% w/v.

In some embodiments, the rOVD consumable composition is a solid composition. In such cases, the concentration of rOVD in the solid composition may be between 0.1% to 70%. The concentration of rOVD in the solid composition may be at least 0.1%. The concentration of rOVD in the solid composition may be at most 70%. The concentration of rOVD in the solid composition may be 0.1% to 1%, 0.1% to 10%, 0.1% to 20%, 0.1% to 30%, 0.1% to 40%, 0.1% to 50%, 0.1% to 60%, 0.1% to 70%, 1% to 10%, 1% to 20%, 1% to 30%, 1% to 40%, 1% to 50%, 1% to 60%, 1% to 70%, 10% to 20%, 10% to 30%, 10% to 40%, 10% to 50%, 10% to 60%, 10% to 70%, 20% to 30%, 20% to 40%, 20% to 50%, 20% to 60%, 20% to 70%, 30% to 40%, 30% to 50%, 30% to 60%, 30% to 70%, 40% to 50%, 40% to 60%, 40% to 70%, 50% to 60%, 50% to 70%, or 60% to 70% weight per total weight (w/w) and/or weight per total volume (w/v). The concentration of rOVD in the solid composition may be 0.1%, 1%, 10%, 20%, 30%, 40%, 50%, 60%, or 70% w/w or w/v. The concentration of rOVD in the solid composition may be at least 0.1%, 1%, 10%, 20%, 30%, 40%, 50% or 60% w/w or w/v. The concentration of rOVD in the solid composition may be at most 1%, 10%, 20%, 30%, 40%, 50%, 60%, or 70% w/w or w/v.

In some embodiments, the rOVD consumable composition is a powdered composition. In such cases, the concentration of rOVD in the powder composition may be between 15% to 99% weight per total weight (w/w) and/or weight per total volume (w/v). The concentration of rOVD in the powder composition may be at least 15% w/w or w/v. In embodiments, the concentration of rOVD in the powder composition may be at most 99% w/w or w/v. The concentration of rOVD in the powder composition may be 15% to 30%, 15% to 45%, 15% to 60%, 15% to 75%, 15% to 80%, 15% to 85%, 15% to 90%, 15% to 95%, 15% to 99%, 30% to 45%, 30% to 60%, 30% to 75%, 30% to 80%, 30% to 85%, 30% to 90%, 30% to 95%, 30% to 99%, 45% to 60%, 45% to 75%, 45% to 80%, 45% to 85%, 45% to 90%, 45% to 95%, 45% to 99%, 60% to 75%, 60% to 80%, 60% to 85%, 60% to 90%, 60% to 95%, 60% to 99%, 75% to 80%, 75% to 85%, 75% to 90%, 75% to 95%, 75% to 99%, 80% to 85%, 80% to 90%, 80% to 95%, 80% to 99%, 85% to 90%, 85% to 95%, 85% to 99%, 90% to 95%, 90% to 99%, or 95% to 99% w/w or w/v. The concentration of rOVD in the powder composition may be about 15%, 30%, 45%, 60%, 75%, 80%, 85%, 90%, 95%, or 99% w/w or w/v. The concentration of rOVD in the powder composition may be at least 15%, 30%, 45%, 60%, 75%, 80%, 85%, 90% or 95% w/w or w/v. The concentration of rOVD in the powder composition may be at most 30%, 45%, 60%, 75%, 80%, 85%, 90%, 95%, or 99% w/w or w/v.

In some embodiments, the rOVD consumable composition is a concentrated syrup composition. In such cases, the concentration of rOVD in the syrup composition may be between 10% to 60% weight per total weight (w/w) and/or weight per total volume (w/v). The concentration of rOVD in the syrup may be at least 10% w/w or w/v. The concentration of rOVD in the syrup may be at most 60% w/w or w/v. The concentration of rOVD in the syrup may be 10% to 20%, 10% to 30%, 10% to 40%, 10% to 50%, 10% to 60%, 20% to 30%, 20% to 40%, 20% to 50%, 20% to 60%, 30% to 40%, 30% to 50%, 30% to 60%, 40% to 50%, 40% to 60%, or 50% to 60% w/w or w/v. The concentration of rOVD in the syrup may be about 10%, 20%, 30%, 40%, 50%, or 60% w/w or w/v. The concentration of rOVD in the syrup may be at least 10%, 20%, 30%, 40% or 50% w/w or w/v. The concentration of rOVD in the syrup may be at most 20%, 30%, 40%, 50%, or 60% w/w or w/v. The syrup may include any solvent, e.g., water and juice.

Solubility and Clarity

Provided herein, in particular, are compositions of OVD where the OVD protein remains soluble in the composition. In some embodiments of any composition described herein, the proteins are fully soluble at a protein concentration between the lowest amounts of rOVD (e.g., 0.1 g or less) and in increasing amounts up to and including about 30 or 40 grams of rOVD protein per 100 mL of solution. In some embodiments of any composition described herein, the proteins are fully soluble at a concentration of about 1, 2, 5, 7, 10, 12 or 15 g, total OVD protein per 100 mL volume, for example when formulated in a liquid such as water. In some embodiments of any composition described herein, the proteins are fully soluble at a concentration of about 15, about 20, about 25, about 30, or about 40 g, total OVD protein per 100 mL volume, for example when formulated in a liquid such as water. In the compositions herein, the OVD may be native OVD or a recombinant OVD. In some embodiments, OVD is an isolated recombinant protein. In some embodiments, OVD is rOVD with modified glycosylation, such as having one or more asparagine residues modified by N-acetylglucosamine and substantially devoid of N-linked mannosylation.

Solubility of rOVD may be measured by a variety of techniques including visual detection and measuring absorbance of the solution at a wavelength of 600 nm (D600). In some embodiments, solubilized protein composition described herein have absorbance less than 1 (<1) as measured using 600 nm wavelength. In some embodiments, solubilized rOVD compositions described herein have an observed measured transmittance at 600 nm of greater than about 90%, 91%, 92%, 93%, 94%, 95%, 96%, 97%, 98% or 99%. In some embodiments, the addition of rOVD to a composition does not change or only slightly changes the OD600 measurement as compared to the composition without rOVD.

In some embodiments, the addition of rOVD to a composition may increase the OD600 measurement as compared to the composition without rOVD and the increase is less than what would be seen with the addition of another protein, such as whey protein or a native OVD added to the composition in the same amount.

In some embodiments, the addition of rOVD to a composition has a solubility better than whey protein or native OVD, when compared at the same protein concentration and under equivalent conditions (such as pH and temperature treatment). In some embodiments, the addition of rOVD to a composition has a solubility better than whey protein or native OVD when compared at the same protein concentration and the composition is a consumable food composition such as an ingredient or a finished product.

"Clear" or "clarity" as used herein refers to a lack of turbidity. Clarity may be assessed by visual observation, including by comparison to a solution that has no protein included. Such comparisons can be made by machine, by an individual or by a panel of testers, e.g., testers trained in the art of detecting clarity. Clarity of a solution can be tested by a panel of (at least 3, 5, 7, 10, or 12 individuals) or people skilled at such tests. Preferably, at least a majority of testers may be unable to visibly differentiate the rOVD composition from a solution comprising no protein, or a different protein at the same concentration.

In some embodiments, the rOVD compositions exhibit improved clarity as compared to composition with other compositions having a different protein at an equivalent concentration, such as a composition containing pea protein, whey isolates or whey protein, native egg white proteins (e.g., nOVD), or whole egg white. In some embodiments, at least a majority or more of testers may be unable to visibly differentiate the rOVD added to a composition from a solution comprising no protein.

A clear solution may be colored or may be colorless. In some embodiments, a solubilized rOVD protein in a composition may have a lack of color as measured by less than 0.15 absorbance at wavelengths between 350 nm and 850 nm. In some embodiments, a solubilized rOVD protein in a composition may provide a color such as yellow, green or brown or shades thereof to a consumable food composition. In some cases, rOVD and/or the solubilized rOVD protein may be treated with an oxidizing agent or oxygen generating agent to modify the color of the solution to a lighter or less intense color.

In some embodiments, a composition of rOVD in solution, such as in a liquid consumable food composition, is essentially clear at a protein concentration between the lowest amounts of rOVD (e.g., 0.1 g) and in increasing amounts up to and including about 30 grams of rOVD protein per 100 mL of solution. In some embodiments, a composition of rOVD in solution, such as in a liquid consumable food composition, is essentially clear at a high protein concentration of about 10, 11, 12, 13, 14, 15, 16, 17, 18, 19, 20, 21, 22, 23, 24, 25, 26, 27, 28, 29 or 30 grams of rOVD protein per 100 mL of solution. In some embodiments, an rOVD composition is essentially clear with at least about 9, 10, 11, 12, 13, 14, 15, 16, 17, 18, 19, 20, 21, 22, 23, 24, 25, 26, 27, 28, 29, or 30 g of total rOVD protein per 100 mL of solution (e.g., such as in 100 mL of water).

In some embodiments, an rOVD composition has a clarity better than whey protein, such as whey protein isolate or whey protein concentrate, when compared at the same protein concentration and under equivalent conditions (such as pH and temperature). In some embodiments, an rOVD composition has a clarity better than whey protein when compared at the same protein concentration and the rOVD composition is a component of a consumable food composition such as a finished product or as an ingredient in a finished product.

In some embodiments, an rOVD composition has a clarity better than native OVD (nOVD) when compared at the same protein concentration and under equivalent conditions (such as pH and temperature). In some embodiments, an rOVD composition has a clarity better than an nOVD composition when compared at the same protein concentration and the rOVD composition is a component of a consumable food composition such as a finished product or as an ingredient in a finished product.

In some embodiments herein, a composition of rOVD has both substantial solubility and is substantially clear at concentrations at least about 9, 10, 11, 12, 13, 14, 15, 16, 17, 18, 19, 20, 21, 22, 23, 24, 25, 26, 27, 28, 29, 30 g or more than 30 g of total rOVD protein per 100 mL of solution (e.g., such as in 100 mL of water).

In some cases, rOVD remains soluble and clear in a consumable composition when the composition is heated to a temperature greater than 50° C., 60° C., or 70° C. or between about 70° C. and about 120° C., even when the rOVD is at a concentration of at least 2%, 4%, 10%, 20, 30%, 40%, or 50% on a w/v basis.

In one instance, clarity of a consumable composition herein is determined using absorbance of visible light, such as by measuring absorbance of the solution at a wavelength of 600 nm (OD600). Preferably, a liquid or semi-liquid consumable composition herein has an absorbance that is less than 1.2, 1.1, 1, 0.5, 0.4, 0.3, 0.2, 0.1, 0.09, 0.08, 0.07, 0.06, 0.05 or 0.04 when determined using visible light at 600 nm. Other methods to measure solubility include examining solubility by centrifuge concentration followed by protein concentration assays such as Coomassie Plus (Bradford) Protein Assay (Thermo Scientific) and Bicinchoninic Acid (BCA) Protein Assay (Sigma-Aldrich).

In some instances, clarity of a consumable composition is one that is not substantially different from the clarity of the solution before the addition of rOVD. For example, an addition of rOVD to a solution (consumable composition) does not change or does not substantially change (change of less than 0.03, 0.02, 0.01) the OD600 measurement as compared to the composition without rOVD.

Thus, a consumable composition comprising rOVD may have a clarity less than 2 as measured at OD600 in room temperature, with a concentration of rOVD of at least or about 10%, 15%, 20%, 25%, or 30% rOVD weight per total weight (w/w) and/or weight per total volume (w/v). Alternatively, a solution comprising rOVD at a concentration greater than 10% w/w or w/v can have a clarity that is less than 2, 1.8, 1.6, 1.4, 1.2, 1, 0.8, 0.6, 0.4, 0.2, 0.1, 0.08, 0.06, 0.04 or 0.02 as measured at OD 600 in room temperature. A substantially optically clear solution may refer to a solution where the OD600 measurement is less than or equal to about 0.1. In some cases, a substantially optically clear solution has an OD600 measurement of less than 0.08, 0.06, 0.05 or 0.02.

In some embodiments, addition of rOVD increases the protein concentration by at least 1%, 2%, 3%, 4%, 5%, 6%, 7%, 8%, 9%, 10%, 11%, 12%, 13%, 14%, 15%, 16%, 17%, 18%, 19% or 20% weight per total weight (w/w) and/or weight per total volume (w/v) without reducing clarity or increasing turbidity by more than 1%, 2%, 3%, 4%, 5%, 6%, 7%, 8%, 9%, or 10% w/w or w/v of the solution as compared to the solution before introduction of the rOVD.

In some embodiments, rOVD protein may be added in an amount (such as a percentage by total weight or volume of the consumable food composition) that is greater than what could be added with other protein sources used in edible products such as whey proteins (such as whey protein isolate (WPI) and whey protein concentrate (WPC)), all embodiments of pea protein, soy protein, whole egg or egg white proteins (e.g., native OVD), while still maintaining the solubility, or solubility and clarity properties of the composition.

Sensory Neutrality and Improved Sensory Appeal

In some embodiments, in addition to the increased protein nutrition content, the addition of rOVD to a consumable food composition provides sensory neutrality or an improved sensory appeal as compared to other proteins in such compositions. As used herein "sensory neutrality" refers to the absence of a strong or distinctive taste, odor (smell) or combination of taste and smell, as well as texture, mouth-feel, aftertaste and color. A sensory panel such as one described in Kemp et al. 2009 may be used by a panel of trained analysts. Sensory neutrality may provide an improved sensory appeal to a taster, such as a tester of foods or a consumer, when a consumable food composition containing rOVD with another like composition that has a different protein such as whey protein, pea protein, soy protein, whole egg or egg white protein at the same concentration.

In some embodiments, rOVD when added to a consumable food composition is substantially odorless, such as measured by a trained sensory panel, in comparison with different solutions with a different protein component present in an equal concentration to the rOVD containing solution, for example, in the comparison is whey, soy, collagen, pea, egg white solid isolates and/or native OVD. In some embodiments of the rOVD compositions described herein, such compositions are essentially odorless at a protein concentration between about 5-10%, 10-15%, 15-20%, 20-25%, 25-30% or greater than 30% rOVD weight per total weight (w/w) and/or weight per total volume (w/v) or at a protein concentration of about 10, 11, 12, 13, 14, 15, 16, 17, 18, 19, 20, 21, 22, 23, 24, 25, 26, 27, 28, 29, 30 or more than 30 g of total rOVD protein per 100 mL solution (e.g., per 100 mL water).

In some embodiments, the addition of rOVD to a consumable food composition also provides a neutral taste in addition to the characteristics such as increased protein nutrition content, solubility, clarity, and/or odorless. A neutral taste can be measured for example, by a trained sensory panel in comparison with solutions containing a different protein present in an equal concentration to the rOVD, for example, whey, soy, collagen, pea, whole egg, and egg white solid isolates (including native OVD).

In some embodiments, the addition of rOVD provides a reduction in a certain odor and/or taste that is associated with other proteins used for supplementation. For example, addition of rOVD has less of an "egg-like" odor or taste as compared to the addition of whole egg, fractionated egg or egg-white to a consumable food composition. In some embodiments, addition of rOVD has less of a metallic odor or taste as compared to other protein sources.

In some embodiments, the addition of rOVD has an improved mouth-feel as compared to the addition of other protein sources. For example, the addition of rOVD is less grainy or has less precipitate or solids as compared to other protein sources.

In some embodiments, the addition of rOVD has an improved texture, for example, as compared to other available supplemental protein sources.

In some embodiments, the addition of rOVD has an improved or appealing color or visual appeal as compared to other available supplemental protein sources. For example, the addition of rOVD may maintain the clarity of a liquid (such as a carbonated drink, a protein water, sports drink) and provide visual appeal for the consumer.

A consumable composition with rOVD may also have an improved sensory appeal as compared to the composition without rOVD or with a different protein present in an equal concentration to the rOVD. Such improved sensory appeal may relate to taste and/or smell. Taste and smell can be measured, for example, by a trained sensory panel. In some instances, a sensory panel compares a consumable composition with rOVD to one without it or with a different protein in an equivalent amount.

As described herein, a consumable composition herein can be in a liquid form. A liquid form can be an intermediate product such as soluble rOVD solution. In some cases, a liquid form can be a final product, such as a beverage comprising rOVD. Example of different types of beverages contemplated herein include: a juice, a soda, a soft drink, a flavored water, a protein water, a fortified water, a carbonated water, a nutritional drink, an energy drink, a sports drink, a recovery drink, a heated drink, a coffee-based drink, a tea-based drink, a plant-based milk, a milk based drink, a non-dairy, plant based mild drink, infant formula drink, and a meal replacement drink.

Non-limiting examples of juice drinks include Odwalla®, Naked®, and MinuteMaid®.

Non-limiting examples of soda drinks include: Coca-Cola®, Pepsi®, Sprite® and 7Up®.

Non-limiting examples of recovery drinks include Gatorade™, Pedialyte®, Powerade® and Propel®.

Non-limiting examples of an energy drink include Red Bull™, Monster™, Full Throttle®, AMP®, Rockstar®, Bang™, Reign™, NOS®, Venom®, and energy shots such as 5-Hour Energy™.

Other examples of liquid form final products include broth, soup and liquid food.

A liquid form can be a cold drink, a hot or warm drink, or a room-temperature drink Any of the liquid forms herein can be carbonated. Carbonation can be achieved using any safe gas such as carbon dioxide.

In one embodiment, a consumable composition is sparkling water (such as San Pellegrino™) and has between 0.5 and 30% w/w or w/v rOVD. Such product has an OD 600 less than 0.2, preferably less than 0.15 while remaining essentially colorless, odorless and tasteless.

In one embodiment, a consumable composition is a soda drink (such as Diet Coke™ Pepsi™ Coke™) and has between 0.5 and 30% w/w or w/v rOVD. Such product retains a sensory profile (taste, odor, smell and clarity) comparable to the composition without the addition of rOVD.

In some embodiments, a consumable composition is in a semi-sold form. Examples of semi-solid consumable compositions include: a jelly, a candy, a broth, a soup, a syrup, a gelatin-containing product, a gelled product, and a gummy product, or a combination thereof.

Compatibility with Additional Ingredients

Provided herein are compositions with rOVD wherein the rOVD is compatible with one or more additional ingredients that are used in the preparation of a consumable food composition, including a finished product. Such compatibility provides fortification of protein content to the consumable food composition, while maintaining one or more desired characteristics of the consumable food composition.

In some embodiments, rOVD is compatible with gluten-containing ingredients. For example, rOVD can be added with a gluten-containing ingredient to achieve protein fortification and maintain gluten-structure necessary for the ingredient and/or finished product. For example, rOVD can be used as an ingredient for the production of protein fortified baked goods, a bread, a cookie, a cracker, a biscuit, a frozen dairy product, a frozen "dairy-like" product, a prepared meal, a meat product, a meatless product, a burger, a patty, a protein supplement, a snack bar, a protein bar, a nutrition bar, an energy bar, a dessert, a salad dressing, an egg-wash product, or an "egg-like" product, pastries, cakes and noodles. In the finished product, the rOVD does not substantially interfere with the gluten structure or has a substantially reduced interference with gluten structure as compared to other protein sources.

In some embodiments, rOVD is compatible with gluten-free ingredients. For example, rOVD can be added with a gluten-free ingredient mix to achieve protein fortification and provide structure and/or texture to the finished product. Gluten-free ingredients and finished products include such grains and starches (rice, corn, sorghum, and other cereals), root tubers such as potato, and legumes and pulses such as chickpeas and lentils. For example, rOVD can be used as an ingredient for the production of protein fortified gluten-free products including baked goods, a bread, a cookie, a cracker, a biscuit, a frozen dairy product, a frozen "dairy-like" product, a prepared meal, a meat product, a meatless product, a burger, a patty, a protein supplement, a snack bar, a protein bar, a nutrition bar, an energy bar, a dessert, or an "egg-like" product, pastries, cakes and noodles.

In some embodiments, rOVD is compatible with salts such that rOVD protein does not precipitate out from solution. For example, for use in foods and beverages such as protein smoothies, vegan milk and fruit juices fortified with rOVD, the protein remains substantially in solution. Addition of rOVD does not precipitate in vitamin/mineral fortified environment such as present with fruit juice and juice-like products, and rOVD provides increased protein content and nutrition.

rOVD Combinations with a Second Source of Amino-Acids

In some embodiments, rOVD is added to a consumable food composition and a second source of amino acids is added, such that the combination has an increased protein content and provides a desired amount or balance of amino acid content. In some embodiments, the second source of amino acids is a second protein (either a native protein or a recombinant protein). In some embodiments, the second source of amino acids is provided by adding one or more free amino acids.

In some embodiments, rOVD is added to a consumable food composition and a second protein is added, such that the combination has an increased protein content and provides a desired amount or balance of amino acid content. In some embodiments, the second protein is a recombinant protein. In some embodiments, the second protein is a native protein, e.g., isolated from its native source.

Protein content of compositions can be measured by various methods such as the protein digestibility-corrected amino acid score (PDCAAS) method. PDCAAS refers to a method for the measurement of the protein value in human nutrition. The method is based on comparison of the concentration of the first limiting essential amino acid in the test protein with the concentration of that amino acid in a reference (scoring) pattern. The method compares the amino acid profile of the specific food protein against a standard amino acid profile with the highest possible score being a 1.0, such 1.0 score meaning the specific food protein provides per unit of protein 100% or more of the indispensable amino acids required for human nutrition (see e.g., FAO/WHO/UNU Expert Consultation 1985).

The formula for calculating the PDCAAS percentage is: (mg of limiting amino acid in 1 g of test protein/mg of same amino acid in 1 g of reference protein)×fecal true digestibility percentage. PDCAAS scores above 1.0 are truncated to 1.0. Amino acid score (not corrected or truncated) can exceed 1.0.

In some embodiments, the combination of rOVD and a second protein increases the protein content and provides a PDCAAS of greater than about 0.75. In some embodiments, the combination provides a PDCAAS of or of about 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99 or 1.0. In some embodiments, the combination provides a PDCAAS of greater than or greater than about 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, or 0.95. In some embodiments the combination provides a PDCAAS of or of about 1.0.

In some embodiments, the ratio of rOVD and second protein is selected to provide a PDCAAS of at least about 0.75 and wherein the combination of rOVD and second protein remains soluble in the consumable food composition. In some embodiments of a herein-disclosed combination of rOVD and a second protein, rOVD is present in the combination at or at about 95%, 90%, 89%, 88%, 87%, 86%, 85%, 84%, 83%, 82%, 81%, 80%, 79%, 78%, 77%, 76%, 75%, 74%, 73%, 72%, 71%, or 70% weight per total weight (w/w) and/or weight per total volume (w/v). In some embodiments of a herein-disclosed combination of rOVD and a second protein, rOVD is present in the combination at or at about 69%, 78%, 67%, 66%, 65%, 64%, 63%, 62%, 61%, 60%, 59%, 58%, 57%, 56%, 55%, 54%, 53%, 52%, 51%, or 50% w/w or w/v. In some embodiments of the combination of rOVD and the second protein, rOVD is present in the combination in a percentage of total protein at least or at least about 60%, 65%, 70%, 75%, 80% or greater than 80% w/w or w/v. In some embodiments of a herein-disclosed combination of rOVD and a second protein, the second protein is present in the combination at an above percentage, such the rOVD is provided in a lesser amount than the second protein.

In some embodiments, a second protein is selected based on its amino acid composition. In some embodiments, a second protein provides tryptophan to the composition. In some embodiments, a second protein provides tryptophan such that the combination with rOVD has a tryptophan content of at least about 1.7 g per 100 g total protein.

In some embodiments, the second protein is lysozyme. In some embodiments, the second protein is egg white lysozyme. In some embodiments, the second protein is a recombinant protein. In some embodiments, the second protein is a recombinant egg white lysozyme (rOVL).

The rOVD and rOVL can be processed or mixed together prior to mixing with any other food ingredients or consumable food products. Alternatively, either the rOVD or the rOVL can be processed or mixed individually, either at the same time or separately, with any other food ingredients or consumable food products. In embodiments, a single transformed cell expresses both rOVL and rOVD.

In some embodiments, the second protein is rOVL and the combination of rOVD and rOVL provides protein fortification while remaining soluble in the composition and providing a PDCAAS of about 1.0. The ratio of rOVD to rOVL can be between about 60% rOVD:40% rOVL to about 82% rOVD:18% rOVL, or between about 75% rOVD:25% rOVL to about 82% rOVD:18% rOVL weight per total weight (w/w) and/or weight per total volume (w/v).

Native OVD has a PDCAAS of approximately 0.02. Addition of rOVL to rOVD increases the amino acid score and PDCAAS of the combination. As an example, a 78.3% rOVD and 21.7% rOVL blend result in an amino acid score of 0.86 and a PDCAAS of 0.79. With a ratio of rOVD to rOVL from about 78.3% rOVD+21.7% rOVL to about 60% rOVD+40% rOVL provides a range of 0.86 to 1.06 amino acid score. In these exemplary ranges, the combination of rOVD and rOVL remains soluble.

In some embodiments, a consumable composition comprises a protein mixture of rOVD and rOVL. In some cases, a composition comprising a mixture of rOVD and rOVL has about 20%-99% rOVD and 1-20% rOVL. In some examples, the concentration of rOVD in a protein mixture of rOVD and rOVL may be at least 20%. The concentration of rOVD in a protein mixture of rOVD and rOVL may be at most 99%. The concentration of rOVD in a protein mixture of rOVD and rOVL may be about 20% to 30%, 20% to 40%, 20% to 50%, 20% to 60%, 20% to 70%, 20% to 80%, 20% to 90%, 20% to 99%, 30% to 40%, 30% to 50%, 30% to 60%, 30% to 70%, 30% to 80%, 30% to 90%, 30% to 99%, 40% to 50%, 40% to 60%, 40% to 70%, 40% to 80%, 40% to 90%, 40% to 99%, 50% to 60%, 50% to 70%, 50% to 80%, 50% to 90%, 50% to 99%, 60% to 70%, 60% to 80%, 60% to 90%, 60% to 99%, 70% to 80%, 70% to 90%, 70% to 99%, 80% to 90%, 80% to 99%, or 90% to 99% weight per total weight (w/w) and/or weight per total volume (w/v). The concentration of rOVD in a protein mixture of rOVD and rOVL may be about 20%, 30%, 40%, 50%, 60%, 70%, 80%, 90%, or 99% w/w or w/v. The concentration of rOVL in a protein mixture of rOVD and rOVL may be 1% to 20%. The concentration of rOVL in a protein mixture of rOVD and rOVL may be at least 1%. The concentration of rOVL in a protein mixture of rOVD and rOVL may be at most 20%. The concentration of rOVL in a protein mixture of rOVD and rOVL may be 1% to 5%, 1% to 10%, 1% to 15%, 1% to 20%, 5% to 10%, 5% to 15%, 5% to 20%, 10% to 15%, 10% to 20%, or 15% to 20% w/w or w/v. The concentration of rOVL in a protein mixture of rOVD and rOVL may be about 1%, 5%, 10%, 15%, or 20% w/w or w/v.

In some embodiments, the rOVD and second protein provide a PDCAAS similar to other protein sources such as whey protein and whey protein isolate, and the rOVD and second protein provide at least one feature improved as compared to the other protein source including solubility, clarity, sensory neutrality or improvement of taste and/or odor, improved mouthfeel, and compatibility with an additional ingredient. In some embodiments, the rOVD and second protein provide a PDCAAS similar to other protein sources and provided improved solubility and clarity in food preparation and processing conditions, such as pH, heating and carbonation.

In some embodiments, the second source of amino acids added with rOVD is one or more free amino acids. In some embodiments, rOVD can be combined with free amino acids such as Tryptophan, Isoleucine, Leucine and Valine to selectively increase PDCAAS. In some embodiments, the addition of one or more free amino acids provides an amino acid balance similar to the addition of a second protein, such as similar to the PDCAAS achieved with the addition of rOVL. For example, one or more of the following can be added with rOVD: Tryptophan=1.7 g/100 g sample, Isoleucine=2.03 g/100 g sample, Leucine=4.55 g/100 g sample, Valine=4.94 g/100 g sample.

Heating Conditions and pH of Compositions

In some embodiments, the consumable food compositions and methods of making such compositions include a particular pH range, and in such range, the rOVD remains soluble in the composition. In some embodiments, the pH is between about 1.0 and about 8.0. In some embodiments, the pH is between about 2.0 and about 6.0, 6.5, or 7.0. In some embodiments, the pH is between about 2.0 to about 2.5, about 2.5 to about 3.0, about 2.5 to about 3.5, about 3.5 to about 4.0, about 2.5 to about 4.5, about 2.0 to about 4.0, about 4.0 to about 6.0, about 2.0 to about 6.0, about 4.0 to about 6.5, or about 2.0 to about 6.5. In some embodiments, the pH is less than 2.0, or equal to 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5 or greater than 4.5. At such pH or pH range, rOVD remains soluble in the consumable food composition, when the rOVD is an ingredient of a finished product (e.g., as a powdered form for use in a finished product) or in a finished product itself. At such pH or pH range, rOVD remains soluble in the consumable food composition without affecting the texture or graininess of the composition. In semi-solid and solid foods, the solubility of rOVD enables protein fortification without jeopardizing functional and sensory properties of the food product. For instance, the addition of rOVD provides fortification and maintains sensory appeal such as a good mouth-feel and lack of graininess. In some embodiments, the addition of rOVD provides fortification, maintains solubility and as such provides the ability of the rOVD to blend with other ingredients.

In some embodiments, the consumable food compositions and methods of making such compositions include a heating condition. For example, a consumable food composition may be a heated (e.g., fried, boiled, or baked) or may it may be a hot beverage, such as a warm or hot drink, a soup or a broth. In some cases, a consumable food composition may have a heating step as part of the preparation or sterilization process for producing an ingredient or a finished product. For example, a heating step may include pasteurization, hot fill, and/or retorting. In some embodiments, the heating step include heating to a temperature between about 72° C. and about 121° C. For example, a heating step may be a pasteurization, where the composition is heated to 72° C. for 1 minute and then cooled and stored, including storage at room temperature or refrigerated. For hot fill, a composition may be heated to 85° C. to 95° C., such as for 30 seconds and then placed at room temperature. Retorting may include heating to 121° C. under pressure, such as heating for 15 minutes at 19 psi, and then storing at room temperature.

Preparation of a consumable composition can also include one or more heating steps. A heating step can comprise pasteurization, hot fill, and/or retorting. In some embodiments, the heating step includes heating to a temperature between about 70° C. and about 150° C.

In one example, a pasteurization heating step is performed at temperatures ranging between 70° C. and 100° C.

In one example, hot filling heating step is performed at about 90° C. to about 97° C.

In one example, retorting is performed at about 100° C. to about 140° C. The retorting may be performed for about 10 or more minutes and at about or at least 12 psi.

In some embodiments, the consumable food compositions and methods of making such compositions with rOVD provide a greater protein solubility or a greater protein solubility and improved clarity at pH ranges and/or with heating as compared to composition containing a different protein, such as whey protein, soy protein, pea protein, whole egg protein (e.g., native OVD), or whole egg white protein at the same concentration.

In some cases, rOVD provides protein solubility in a consumable food composition at a pH between about 2 and about 6, at rOVD concentrations of concentrations of about 9, 10, 11, 12, 13, 14, 15, 16, 17, 18, 19, 20, 21, 22, 23, 24, 25, 26, 27, 28, 29, 30 g or more than 30 g of total rOVD protein per 100 mL of solution (e.g., such as in 100 mL of water) or at a percentage of about 9, 10, 11, 12, 13, 14, 15, 16, 17, 18, 19, 20, 21, 22, 23, 24, 25, 26, 27, 28, 29, 30 percent on a weight per total composition volume basis. In some cases, rOVD provides protein solubility and clarity in a consumable food composition at a pH between about 2 and about 6, at rOVD concentrations of about 9, 10, 11, 12, 13, 14, 15, 16, 17, 18, 19, 20, 21, 22, 23, 24, 25, 26, 27, 28, 29, 30 g or more than 30 g of total rOVD protein per 100 mL of solution (e.g., such as in 100 mL of water) or at a percentage of about 9, 10, 11, 12, 13, 14, 15, 16, 17, 18, 19, 20, 21, 22, 23, 24, 25, 26, 27, 28, 29, 30 percent on a weight per total composition volume basis.

In some cases, rOVD provides protein solubility in a consumable food composition when the composition is heated to a temperature between about 72° C. and about 121° C. at rOVD concentrations of concentrations of about 9, 10, 11, 12, 13, 14, 15, 16, 17, 18, 19, 20, 21, 22, 23, 24, 25, 26, 27, 28, 29, 30 g or more than 30 g of total rOVD protein per 100 mL of solution (e.g., such as in 100 mL of water) or at a percentage of about 9, 10, 11, 12, 13, 14, 15, 16, 17, 18, 19, 20, 21, 22, 23, 24, 25, 26, 27, 28, 29, 30 percent on a weight per total composition volume basis. In some cases, rOVD provides protein solubility and clarity in a consumable food composition when the composition is heated to a temperature between about 72° C. and about 121° C. at rOVD concentrations of concentrations of about 9, 10, 11, 12, 13, 14, 15, 16, 17, 18, 19, 20, 21, 22, 23, 24, 25, 26, 27, 28, 29, 30 g or more than 30 g of total rOVD protein per 100 mL of solution (e.g., such as in 100 mL of water) or at a percentage of about 9, 10, 11, 12, 13, 14, 15, 16, 17, 18, 19, 20, 21, 22, 23, 24, 25, 26, 27, 28, 29, 30 percent on a weight per total composition volume basis.

In some cases, rOVD provides protein solubility in a consumable food composition when the composition is heated to a temperature between about 72° C. and about 121° C. and where the composition has a pH between about 2 and about 4, or a pH about 2 to about 6, at rOVD concentrations of concentrations of about 9, 10, 11, 12, 13, 14, 15, 16, 17, 18, 19, 20, 21, 22, 23, 24, 25, 26, 27, 28, 29, 30 g or more than 30 g of total rOVD protein per 100 mL of solution (e.g., such as in 100 mL of water) or at a percentage of about 9, 10, 11, 12, 13, 14, 15, 16, 17, 18, 19, 20, 21, 22, 23, 24, 25, 26, 27, 28, 29, 30 percent on a weight per total composition volume basis. In some cases, rOVD provides protein solubility and clarity in a consumable food composition when the composition is heated to a temperature between about 72° C. and about 121° C., and where the composition has a pH between about 2 and about 4, or a pH about 2 to about 6, at rOVD concentrations of concentrations of about 9, 10, 11, 12, 13, 14, 15, 16, 17, 18, 19, 20, 21, 22, 23, 24, 25, 26, 27, 28, 29, 30 g or more than 30 g of total rOVD protein per 100 mL of solution (e.g., such as in 100 mL of water) or at a percentage of about 9, 10, 11, 12, 13, 14, 15, 16, 17, 18, 19, 20, 21, 22, 23, 24, 25, 26, 27, 28, 29, 30 percent on a weight per total composition volume basis.

Consumable Food Compositions

Consumable food compositions described herein include food products, beverage products, dietary supplements, food additives, and nutraceuticals as non-limiting examples, and also include compositions as an ingredient of a food or beverage or a product ingested as part of an animal diet. In some embodiments, a consumable food composition is a finished product, such as a food or beverage for animal consumption or for human consumption, a dietary supplement, or a nutraceutical product.

In some embodiments, a finished product is a beverage containing rOVD, and optionally a second protein, such as rOVL. The beverage can be a clear beverage, and can be selected from a juice, a soda, a soft drink, a flavored water, an unflavored water, a fortified water, a carbonated water, a nutritional drink, an energy drink, a sports drink, a recovery drink, a heated drink, a coffee-based drink, a tea-based drink, a cocoa based drink, a smoothie, a milk shake, coconut water, beer, wine, alcoholic beverage, nut milks, juice-based beverages, dairy-based beverages, and a plant-based milk. Many of these beverages have a pH that is between about 2 and about 7, and rOVD and/or rOVD and second protein combination remains soluble in such beverages. In some embodiments, the beverage is a heated beverage. In some embodiments, the beverage is a cold beverage or a beverage served or stored at room temperature. In some embodiments, the beverage contains alcohol from 3 to 40% weight per total weight (w/w) and/or weight per total volume (w/v).

In some embodiments the beverage is carbonated. The carbonation may be created by, for example, carbon dioxide, carbonic acid, sodium bicarbonate, and potassium bicarbonate. A composition described herein may be carbonated. In some cases, a composition described herein has about or at least about 0.1, 0.2, 0.3, 0.4, 0.5, 0.6, 0.7, 0.8, 0.9, 1, 1.5, 2, 2.5, 3, 3.5, or 4 volumes of carbon dioxide gas present per volume of beverage. In some cases, a composition described herein has up to about 0.1, 0.2, 0.3, 0.4, 0.5, 0.6, 0.7, 0.8, 0.9, 1, 1.5, 2, 2.5, 3, 3.5, or 4 volumes of carbon dioxide gas present per volume of beverage. In some cases, a composition described herein has about 0.1 volumes to about 4 volumes or about 1.5 volumes to about 3.5 volumes of carbon dioxide gas present per volume of beverage.

In some embodiments, a protein composition may comprise carbon dioxide, and wherein the amount of carbon dioxide added to the soluble protein composition may be in a proportion between 0.01 g and 4.4 g in 355 mL or the gaseous carbon dioxide may be between 0.02 volumes and 5 volumes for every 1 volume of soluble protein composition, and wherein the beverage may have a pH range between about 2 and about 6 or about 2 and about 4. In some embodiments, a carbonated beverage has a pH between 1.0 and 6.0 or about 1.0 and about 4 or between about 1.6 and about 3.4.

In some embodiments, the beverage preparation includes a heating step, such as hot fill, pasteurization or retorting and the rOVD in the beverage remains soluble during and subsequent to the heating step. In some embodiments, the addition of rOVD to the beverage does not substantially alter the visible appearance, smell, flavor or mouthfeel of the beverage as compared to a beverage that does not contain the composition. In some embodiments, the addition of rOVD to the beverage is sensory neutral and provides an improved sensory appeal as compared to other proteins when added to the beverage at the same concentration, such as whey protein, soy protein, pea protein, egg white proteins or whole egg proteins. In some embodiments, the beverage preparation also includes a second protein such as rOVL and the combination of rOVD and the second protein remains soluble during and subsequent to the heating step.

In some embodiments, a finished product is a food product containing rOVD. The food product can be a jelly, a candy, a broth, a soup, a gelatin-containing product, a gelled product and a gummy product. Additional exemplary categories of food products in which rOVD can be added include sauces, dressings, condiments.

rOVD can also be added to seasoning mixes and spices. rOVD can also be used in coating and breadings. rOVD may also be used to increase the protein content of snacks such as fruit and vegetable-based snacks.

rOVD may be used as an egg wash to promote adhesion of seeds or grains to a baked good and/or to improve the visual appearance, such as browning, of the baked good.

In some embodiments herein, a consumable food composition containing rOVD is a composition that is used as an ingredient with other ingredient(s) or component(s) to create a finished product. For example, rOVD can be mixed with water or other liquid, and then this mixture used as an ingredient to create a beverage, food product, dietary supplement or nutraceutical. In some cases, rOVD is mixed with other ingredients, such as other liquids (e.g., nut milks, fruit juices, vegetable extracts or carbonated solutions. This solution can be an ingredient that is then mixed with other ingredients to make a final product for an end-user; for example, the solution may be a syrup containing concentrated rOVD. A final or finished product is one that is ready for an end-user's consumption. The finished product can be a processed product, such as processed food or a processed drink. In some instances, the rOVD is provided in a separate container to be mixed into the final product by the end-user. In some cases, rOVD is mixed with other ingredients, such as gelling agents to make candies, gummy products, gelled products (such as a Jello™) or sportsgels.

During or after preparation of a consumable food product containing rOVD may be formulated as a liquid, solid, syrup, or powder. A composition may be refrigerated, frozen, stored warm, stored at room temperature or held at a heated temperature. Preparation of the food product can include a heating step or the food product is stored or served at a heated temperature, and the rOVD remains soluble in the food product during and subsequent to the heating step. In some cases, the food product can have a pH that is between about 2 and about 6, and rOVD remains soluble in the food product.

Examples of liquid consumable compositions or beverages include: a soda, a vitamin drink, a protein shake, a meal replacement shake, a juice, a refreshment drink, a milk-based drink or a non-dairy based drink, flavored water, a carbonated drink, coffee, caffeinated drink, tea, flower-based drink, beer, liquor, and a sports drink.

Any of the liquid or semi-solid consumable compositions herein can be created by mixing a powdered rOVD into a solution. The solution can be the final product or an intermediate solution which is then further modified to generate a final product.

Examples of solvents that can be used to prepare an rOVD solution include still water, carbonated water, alcohol, juices, and any other commercially available drink including those described in more detail herein.

A method of generating a consumable composition comprising rOVD may comprise mixing rOVD with a solvent and, optionally, one or more other components. The mixing may be performed by any conventionally used mixing method including mortar and pestle, mechanical grinder, blending, homogenization process or a sonication process.

The amount of rOVD added to the solution can be one that generates an rOVD concentration as derived herein (either in the final product or an intermediate product).

Preferably, addition of the rOVD to the solution results in most or nearly all of the rOVD solubilized into the solution at room temperature. In one instance, solubility is determined based on clarity or degree of lack of turbidity.

The consumable compositions herein can also be subjected to a heating step. Such a step can modify or increase solubility of the rOVD. For example, it was found that performing a heating step in the process of making a product such as retorting, hot filling, or pasteurization can increase solubility and hence clarity of an rOVD solution herein.

Preparation of a consumable food product containing rOVD may include processing steps, for example, freezing, chilling, heating, baking, roasting, broiling, boiling, blanching, packaging, canning, bleaching, enriching, drying, pressing, grinding, mixing, par cooking, cooking, proofing, marinating, cutting, slicing, dicing, crushing, shredding, chopping, shaking, coring, spiralizing, rolling, juicing, straining, filtering, kneading, whisking, beating, whipping, grating, stuffing, peeling, deseeding, smoking, curing, salting, preserving, pickling, fermenting, homogenizing, pasteurizing, sterilizing, irradiating, cold plasma processing, high pressure processing, pulse electric field processing, microwave assisted thermal sterilization, stabilizing, blending, pureeing, fortifying, refining, hydrogenating, aging, extending shelf life, or adding enzymes.

Preparation of a consumable food product containing rOVD may include drying and/or concentrating. In some cases, drying forms a dry, dehydrated, concentrated, and/or solid protein or composition. Some non-limiting examples of drying methods include thermal drying, evaporation (e.g., by means of vacuum or air), distillation, boiling, heating in an oven, vacuum drying, spray drying, freeze drying, and lyophilization, or any combination thereof.

Preparation of a consumable food product containing rOVD may include diluting and/or hydrating. In some cases, the diluting may comprise addition of a liquid, which may be water or another liquid form. For example, a composition can be diluted (e.g., from 20% water to 99.9% water). In another example, a dry composition can be hydrated (e.g., from a dry solid to 99.9% water).

In some embodiments, the consumable food composition containing rOVD is in powder form and when the powdered composition is formulated into a solution, the rOVD is substantially fully soluble. In some embodiments, when the powdered composition is formulated into a solution, the rOVD is substantially fully soluble and the solution is substantially clear. In some embodiments, when the powdered composition is formulated into a solution, the rOVD is substantially fully soluble, the solution is substantially clear and the solution is essentially sensory neutral or has an improved sensory appeal as compared to solutions made with other powder zed proteins such whey protein, soy protein, pea protein, egg white protein or whole egg proteins. In some embodiments, the powdered composition is solubilized in water where the concentration of rOVD is or is about 1%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% or 40% weight per total weight (w/w) and/or weight per total volume (w/v) of composition.

In some embodiments of the consumable food compositions described herein, the composition is essentially free of animal-derived component, whey protein, caseinate, fat, lactose, hydrolyzed lactose, soy protein, collagen, hydrolyzed collagen, or gelatin, or any combination thereof. A composition described herein may be essentially free of cholesterol, glucose, fat, saturated fat, trans fat, or any combination thereof. In some cases, a composition described herein comprises less than 10%, 5%, 4%, 3%, 2%, 1%, or 0.5% fat by dry weight. In some embodiments, the composition may be fat-containing (e.g., such as a mayonnaise) and such composition may include up to about 60% fat or a reduced-fat composition (e.g., reduced fat mayonnaise) and such composition may include lesser percentages of fat. A composition that free of an animal-derived component can be considered vegetarian and/or vegan.

In some embodiments, an rOVD powder composition comprises less than 5% ash. The term "ash" is an art-known term and represents inorganics such as one or more ions, elements, minerals, and/or compounds In some cases, the rOVD powder composition comprises less than 5%, 4.5%, 4%, 3.5%, 3%, 2.5%, 2%, 1.5%, 1%, 0.75%, 0.5%, 0.25% or 0.1% ash weight per total weight (w/w) and/or weight per total volume (w/v).

In some embodiments, the moisture content of an rOVD powder composition may be less than 15%. The rOVD powder composition may have less than 15%, 12%, 10%, 8%, 6%, 5%, 3%, 2% or 1% moisture weight per total weight (w/w) and/or weight per total volume (w/v). In some embodiments, the carbohydrate content of an rOVD powder composition may be less than 30%. The rOVD powder composition may have less than 30%, 27%, 25%, 22%, 20%, 17%, 15%, 12%, 10%, 8%, 5%, 3% or 1% carbohydrate content w/w or w/v.

In some cases, the protein content of an rOVD powder composition may be 30% to 99% weight per total weight (w/w) and/or weight per total volume (w/v). In some cases, the protein content of an rOVD powder composition may be at least 30% w/w or w/v. In some cases, the protein content of an rOVD powder composition may be at most 99% w/w or w/v. In some cases, the protein content of an rOVD powder composition may be 30% to 40%, 30% to 50%, 30% to 60%, 30% to 70%, 30% to 75%, 30% to 80%, 30% to 85%, 30% to 90%, 30% to 95%, 30% to 99%, 40% to 50%, 40% to 60%, 40% to 70%, 40% to 75%, 40% to 80%, 40% to 85%, 40% to 90%, 40% to 95%, 40% to 99%, 50% to 60%, 50% to 70%, 50% to 75%, 50% to 80%, 50% to 85%, 50% to 90%, 50% to 95%, 50% to 99%, 60% to 70%, 60% to 75%, 60% to 80%, 60% to 85%, 60% to 90%, 60% to 95%, 60% to 99%, 70% to 75%, 70% to 80%, 70% to 85%, 70% to 90%, 70% to 95%, 70% to 99%, 75% to 80%, 75% to 85%, 75% to 90%, 75% to 95%, 75% to 99%, 80% to 85%, 80% to 90%, 80% to 95%, 80% to 99%, 85% to 90%, 85% to 95%, 85% to 99%, 90% to 95%, 90% to 99%, or 95% to 99% w/w or w/v. In some cases, the protein content of an rOVD powder composition may be about 30%, 40%, 50%, 60%, 70%, 75%, 80%, 85%, 90%, 95%, or 99% w/w or w/v. In some cases, the protein content of an rOVD powder composition may be at least 30%, 40%, 50%, 60%, 70%, 75%, 80%, 85%, 90% or 95% w/w or w/v. In some cases, the protein content of an rOVD powder composition may be at most 40%, 50%, 60%, 70%, 75%, 80%, 85%, 90%, 95%, or 99% w/w or w/v.

Additional Components of Compositions

The consumable food compositions containing rOVD disclosed herein and the methods of making such compositions may including adding or mixing the rOVD with one or more ingredients. For example, food additives may be added in or mixed with the compositions. Food additives can add volume and/or mass to a composition. A food additive may improve functional performance and/or physical characteristics. For example, a food additive may prevent gelation or increased viscosity due to the lipid portion of the lipoproteins in the freeze-thaw cycle. An anticaking agent may be added to make a free-flowing composition. Carbohydrates can be added to increase resistance to heat damage, e.g., less protein denaturation during drying and improve stability and flowability of dried compositions. Food additives include, but are not limited to, food coloring, pH adjuster, natural flavoring, artificial flavoring, flavor enhancer, batch marker, food acid, filler, anticaking agent (e.g., sodium silico aluminate), antigreening agent (e.g., citric acid), food stabilizer, foam stabilizer or binding agent, antioxidant, acidity regulatory, bulking agent, color retention agent, whipping agent (e.g., ester-type whipping agent, triethyl citrate, sodium lauryl sulfate), emulsifier (e.g., lecithin), humectant, thickener, excipient, solid diluent, salts, nutrient, sweetener, glazing agent, preservative, vitamin, dietary elements, carbohydrates, polyol, gums, starches, flour, oil, or bran.

Food coloring includes, but is not limited to, FD&C Yellow #5, FD&C Yellow #6, FD&C Red #40, FD&C Red #3, FD&C Blue No. 1, FD&C Blue No. 2, FD&C Green No. 3, carotenoids (e.g., saffron, β-carotene), anthocyanins, annatto, betanin, butterfly pea, caramel coloring, chlorophyllin, elderberry juice, lycopene, carmine, pandan, paprika, turmeric, curcuminoids, quinoline yellow, carmoisine, Ponceau 4R, Patent Blue V, and Green S.

Ingredients for pH adjustment include, but are not limited to, Tris buffer, potassium phosphate, sodium hydroxide, potassium hydroxide, citric acid, sodium citrate, sodium bicarbonate, and hydrochloric acid.

Salts include, but are not limited to, acid salts, alkali salts, organic salts, inorganic salts, phosphates, chloride salts, sodium salts, sodium chloride, potassium salts, potassium chloride, magnesium salts, magnesium chloride, magnesium perchlorate, calcium salts, calcium chloride, ammonium chloride, iron salts, iron chlorides, zinc salts, and zinc chloride.

Nutrient includes, but is not limited to, macronutrient, micronutrient, essential nutrient, non-essential nutrient, dietary fiber, amino acid, essential fatty acids, omega-3 fatty acids, and conjugated linoleic acid.

Sweeteners include, but are not limited to, sugar substitute, artificial sweetener, acesulfame potassium, advantame, alitame, aspartame, sodium cyclamate, dulcin, glucin, neohesperidin dihydrochalcone, neotame, P-4000, saccharin, aspartame-acesulfame salt, sucralose, brazzein, curculin, glycyrrhizin, glycerol, inulin, mogroside, mabinlin, maltooligosaccharide, mannitol, miraculin, monatin, monellin, osladin, pentadin, stevia, trilobatin, and thaumatin.

Carbohydrates include, but are not limited to, sugar, sucrose, glucose, fructose, galactose, lactose, maltose, mannose, allulose, tagatose, xylose, arabinose, high fructose corn syrup, high maltose corn syrup, corn syrup (e.g., glucose-free corn syrup), sialic acid, monosaccharides, disaccharides, and polysaccharides (e.g., polydextrose, maltodextrin).

Polyols include, but are not limited to, xylitol, maltitol, erythritol, sorbitol, threitol, arabitol, hydrogenated starch hydrolysates, isomalt, lactitol, mannitol, and galactitol (dulcitol).

Gums include, but are not limited to, gum arabic, gellan gum, guar gum, locust bean gum, acacia gum, cellulose gum, and xanthan gum.

Vitamins include, but are not limited to, niacin, riboflavin, pantothenic acid, thiamine, folic acid, vitamin A, vitamin B6, vitamin B12, vitamin D, vitamin E, lutein, zeaxanthin, choline, inositol, and biotin.

Dietary elements include, but are not limited to, calcium, iron, magnesium, phosphorus, potassium, sodium, zinc, copper, manganese, selenium, chlorine, iodine, sulfur, cobalt, molybdenum, nickel, and bromine.

Packaging

One of the benefits of the consumable compositions disclosed herein is that they allow for simpler packaging. In one instance, a consumable liquid composition disclosed herein may be packaged in a clear container as the lack of turbidity in the composition results in a more consumer-appealing product.

A consumable composition can be refrigerated, frozen, stored warm, stored at room temperature or held at a heated temperature.

An rOVD composition may be packaged as a powder, a concentrated syrup, a consumable food product, a beverage, a ready-to-use foodstuff, an ingredient, or a finished product.

Recombinant OVD and OVL

In any composition described herein, the protein may be recombinantly expressed in a host cell. The recombinant protein may be OVD, a first non-recombinant protein (e.g., OVD) and a second recombinant protein such as lysozyme (e.g. rOVL), or OVD and at least one second protein may both be recombinantly produced (for example rOVD and rOVL).

rOVD or rOVL can have an amino acid sequence from any species. For example, an rOVD can have an amino acid sequence of OVD native to a bird (avian) or a reptile or Platypus and a rOVL can have an amino acid sequence of OVL native to a bird or a reptile or Platypus. An rOVD and/or rOVL having an amino acid sequence from an avian OVD and/or OVL can be selected from the group consisting of: poultry, fowl, waterfowl, game bird, chicken, quail, turkey, turkey vulture, hummingbird, duck, ostrich, goose, gull, guineafowl, pheasant, emu, and any combination thereof. An rOVD and/or rOVL can have an amino acid sequence native to a single species, such as *Gallus Gallus domesticus*. Alternatively, an rOVD and/or rOVL can have an amino acid sequence native to two or more species, and as such be a hybrid.

Exemplary OVD and OVL amino acid sequences contemplated herein are provided in Table 1 below as SEQ ID NOs: 1-44 and 45-51, respectively.

TABLE 1

| Sequence Description | SEQ ID NOs | SEQUENCES |
|---|---|---|
| Ovomucoid (canonical) mature chicken OVD | SEQ ID NO: 1 | AEVDCSRFPNATDKEGKDVLVCNKDLRPICGTDGVTYTNDCLLCAYSIEFGT NISKEHDGECKETVPMNCSSYANTTSEDGKVMVLCNRAFNPVCGTDGVTYD NECLLCAHKVEQGASVDKRHDGGCRKELAAVSVDCSEYPKPDCTAEDRPLC GSDNKTYGNKCNFCNAVVESNGTLTLSHFGKC |

TABLE 1-continued

Sequences

| Sequence Description | SEQ ID NOs | SEQUENCES |
|---|---|---|
| Ovomucoid variant of SEQ ID 1 | SEQ ID NO: 2 | AEVDCSRFPNATDMEGKDVLVCNKDLRPICGTDGVTYTNDCLLCAYSVEFGT NISKEHDGECKETVPMNCSSYANTTSEDGKVMVLCNRAFNPVCGTDGVTYD NECLLCAHKVEQGASVDKRHDGGCRKELAAVSVDCSEYPKPDCTAEDRPLC GSDNKTYGNKCNFCNAVVESNGTLTLSHFGKC |
| G162MF167A Ovomucoid Variant of Chicken OVD in Genbank | SEQ ID NO: 3 | AEVDCSRFPNATDMEGKDVLVCNKDLRPICGTDGVTYTNDCLLCAYSVEFGT NISKEHDGECKETVPMNCSSYANTTSEDGKVMVLCNRAFNPVCGTDGVTYD NECLLCAHKVEQGASVDKRHDGGCRKELAAVSVDCSEYPKPDCTAEDRPLC GSDNKTYMNKCNACNAVVESNGTLTLSHFGKC |
| Ovomucoid isoform 1 precursor full length | SEQ ID NO: 4 | MAMAGVFVLFSFVLCGFLPDAAFGAEVDCSRFPNATDKEGKDVLVCNKDLR PICGTDGVTYTNDCLLCAYSIEFGTNISKEHDGECKETVPMNCSSYANTTSED GKVMVLCNRAFNPVCGTDGVTYDNECLLCAHKVEQGASVDKRHDGGCRKE LAAVSVDCSEYPKPDCTAEDRPLCGSDNKTYGNKCNFCNAVVESNGTLTLSH FGKC |
| Ovomucoid [Gallus gallus] | SEQ ID NO: 5 | MAMAGVFVLFSFVLCGFLPDAVFGAEVDCSRFPNATDMEGKDVLVCNKDLR PICGTDGVTYTNDCLLCAYSVEFGTNISKEHDGECKETVPMNCSSYANTTSED GKVMVLCNRAFNPVCGTDGVTYDNECLLCAHKVEQGASVDKRHDGGCRKE LAAVSVDCSEYPKPDCTAEDRPLCGSDNKTYGNKCNFCNAVVESNGTLTLSH FGKC |
| Ovomucoid isoform 2 precursor [Gallus gallus] | SEQ ID NO: 6 | MAMAGVFVLFSFVLCGFLPDAAFGAEVDCSRFPNATDKEGKDVLVCNKDLR PICGTDGVTYTNDCLLCAYSIEFGTNISKEHDGECKETVPMNCSSYANTTSED GKVMVLCNRAFNPVCGTDGVTYDNECLLCAHKVEQGASVDKRHDGGCRKE LAAVDCSEYPKPDCTAEDRPLCGSDNKTYGNKCNFCNAVVESNGTLTLSHFG KC |
| Ovomucoid [Gallus gallus] | SEQ ID NO: 7 | AEVDCSRFPNATDKEGKDVLVCNKDLRPICGTDGVTYNNECLLCAYSIEFGT NISKEHDGECKETVPMNCSSYANTTSEDGKVMVLCNRAFNPVCGTDGVTYD NECLLCAHKVEQGASVDKRHDGECRKELAAVSVDCSEYPKPDCTAEDRPLC GSDNKTYGNKCNFCNAVVESNGTLTLSHFGKC |
| Ovomucoid [Numida meleagris] | SEQ ID NO: 8 | MAMAGVFVLFSFALCGFLPDAAFGVEVDCSRFPNATNEEGKDVLVCTEDLRP ICGTDGVTYSNDCLLCAYNIEYGTNISKEHDGECREAVPVDCSRYPNMTSEEG KVLILCNKAFNPVCGTDGVTYDNECLLCAHNVEQGTSVGKKHDGECRKELA AVDCSEYPKPACTMEYRPLCGSDNKTYDNKCNFCNAVVESNGTLTLSHFGK C |
| PREDICTED: Ovomucoid isoform X1 [Meleagris gallopavo] | SEQ ID NO: 9 | MQTITWRQPQGDHLRSRAPAATCRAGQYLTMAMAGIFVLFSFALCGFLPDAA FGVEVDCSRFPNTTNEEGKDVLVCTEDLRPICGTDGVTHSECLLCAYNIEYGT NISKEHDGECREAVPMDCSRYPNTTNEEGKVMILCNKALNPVCGTDGVTYD NECVLCAHNLEQGTSVGKKHDGGCRKELAAVSVDCSEYPKPACTLEYRPLC GSDNKTYGNKCNFCNAVVESNGTLTLSHFGKC |
| Ovomucoid [Meleagris gallopavo] | SEQ ID NO: 10 | VEVDCSRFPNTTNEEGKDVLVCTEDLRPICGTDGVTHSECLLCAYNIEYGTNIS KEHDGECREAVPMDCSRYPNTTSEEGKVMILCNKALNPVCGTDGVTYDNEC VLCAHNLEQGTSVGKKHDGECRKELAAVSVDCSEYPKPACTLEYRPLCGSDN KTYGNKCNFCNAVVESNGTLTLSHFGKC |
| PREDICTED: Ovomucoid isoform X2 [Meleagris gallopavo] | SEQ ID NO: 11 | MQTITWRQPQGDHLRSRAPAATCRAGQYLTMAMAGIFVLFSFALCGFLPDAA FGVEVDCSRFPNTTNEEGKDVLVCTEDLRPICGTDGVTHSECLLCAYNIEYGT NISKEHDGECREAVPMDCSRYPNTTNEEGKVMILCNKALNPVCGTDGVTYD NECVLCAHNLEQGTSVGKKHDGGCRKELAAVDCSEYPKPACTLEYRPLCGS DNKTYGNKCNFCNAVVESNGTLTLSHFGKC |
| Ovomucoid [Bambusicola thoracicus] | SEQ ID NO: 12 | EYGTNISIKHNGECKETVPMDCSRYANMTNEEGKVMMPCDRTYNPVCGTDG VTYDNECQLCAHNVEQGTSVDKKHDGVCGKELAAVSVDCSEYPKPECTAEE RPICGSDNKTYGNKCNFCNAVVYVQP |
| Ovomucoid [Callipepla squamata] | SEQ ID NO: 13 | VDCSRFPNTTNEEGKDVLACTKELHPICGTDGVTYSNECLLCYYNIEYGTNIS KEHDGECTEAVPVDCSRYPNTTSEEGKVLIPCNRDFNPVCGSDGVTYENECLL CAHNVEQGTSVGKKHDGGCRKEFAAVSVDCSEYPKPDCTLEYRPLCGSDNK TYASKCNFCNAVVIWEQEKNTRHHASHSVFFISARLVC |
| Ovomucoid [Colinus virginianus] | SEQ ID NO: 14 | MLPLGLREYGTNTSKEHDGECTEAVPVDCSRYPNTTSEEGKVRILCKKDINPV CGTDGVTYDNECLLCSHSVGQGASIDKKHDGGCRKEFAAVSVDCSEYPKPAC MSEYRPLCGSDNKTYVNKCNFCNAVVYVQPWLHSRCRLPPTGTSFLGSEGRE TSLLTSRATDLQVAGCTAISAMEATRAAALLGLVLLSSFCELSHLCFSQASCD VYRLSGSRNLACPRIFQPVCGTDNVTYPNECSLCRQMLRSRAVYKKHDGRCV KVDCTGYMRATGGLGTACSQQYSPLYATNGVIYSNKCTFCSAVANGEDIDLL AVKYPEEESWISVSPTPWRMLSAGA |

TABLE 1-continued

Sequences

| Sequence Description | SEQ ID NOs | SEQUENCES |
|---|---|---|
| Ovomucoid-like isoform X2 [*Anser cygnoides domesticus*] | SEQ ID NO: 15 | MSWWGIKPALERPSQEQSTSGQPVDSGSTSTTTMAGIFVLLSLVLCCFPDAAF GVEVDCSRFPNTTNEEGKEVLLCTKDLSPICGTDGVTYSNECLLCAYNIEYGT NISKDHDGECKEAVPVDCSTYPNMTNEEGKVMLVCNKMFSPVCGTDGVTYD NECMLCAHNVEQGTSVGKKYDGKCKKEVATVDCSDYPKPACTVEYMPLCG SDNKTYDNKCNFCNAVVDSNGTLTLSHFGKC |
| Ovomucoid-like isoform X1 [*Anser cygnoides domesticus*] | SEQ ID NO: 16 | MSSQNQLHRRRRPLPGGQDLNKYYWPHCTSDRFSWLLHVTAEQFRHCVCIY LQPALERPSQEQSTSGQPVDSGSTSTTTMAGIFVLLSLVLCCFPDAAFGVEVDC SRFPNTTNEEGKEVLLCTKDLSPICGTDGVTYSNECLLCAYNIEYGTNISKDHD GECKEAVPVDCSTYPNMTNEEGKVMLVCNKMFSPVCGTDGVTYDNECMLC AHNVEQGTSVGKKYDGKCKKEVATVDCSDYPKPACTVEYMPLCGSDNKTY DNKCNFCNAVVDSNGTLTLSHFGKC |
| Ovomucoid [*Cotumix japonica*] | SEQ ID NO: 17 | VEVDCSRFPNTTNEEGKDEVVCPDELRLICGTDGVTYNHECMLCFYNKEYGT NISKEQDGECGETVPMDCSRYPNTTSEDGKVTILCTKDFSFVCGTDGVTYDNE CMLCAHNVVQGTSVGKKHDGECRKELAAVSVDCSEYPKPACPKDYRPVCGS DNKTYSNKCNFCNAVVESNGTLTLNHFGKC |
| Ovomucoid [*Cotumix japonica*] | SEQ ID NO: 18 | MAMAGVFLLFSFALCGFLPDAAFGVEVDCSRFPNTTNEEGKDEVVCPDELRLI CGTDGVTYNHECMLCFYNKEYGTNISKEQDGECGETVPMDCSRYPNTTSED GKVTILCTKDFSFVCGTDGVTYDNECMLCAHNIVQGTSVGKKHDGECRKEL AAVSVDCSEYPKPACPKDYRPVCGSDNKTYSNKCNFCNAVVESNGTLTLNHF GKC |
| Ovomucoid [*Anas platyrhynchos*] | SEQ ID NO: 19 | MAGVFVLLSLVLCCFPDAAFGVEVDCSRFPNTTNEEGKDVLLCTKELSPVCG TDGVTYSNECLLCAYNIEYGTNISKDHDGECKEAVPADCSMYPNMTNEEGK MTLLCNKMFSPVCGTDGVTYDNECMLCAHNVEQGTSVGKKYDGKCKKEVA TVDCSGYPKPACTMEYMPLCGSDNKTYGNKCNFCNAVVDSNGTLTLSHFGE C |
| Ovomucoid, partial [*Anas platyrhynchos*] | SEQ ID NO: 20 | QVDCSRFPNTTNEEGKEVLLCTKELSPVCGTDGVTYSNECLLCAYNIEYGTNI SKDHDGECKEAVPADCSMYPNMTNEEGKMTLLCNKMFSPVCGTDGVTYDN ECMLCAHNVEQGTSVGKKYDGKCKKEVATVSVDCSGYPKPACTMEYMPLC GSDNKTYGNKCNFCNAVV |
| Ovomucoid-like [*Tyto alba*] | SEQ ID NO: 21 | MTMPGAFVVLSFVLCCFPDATFGVEVDCSTYPNTTNEEGKEVLVCSKILSPIC GTDGVTYSNECLLCANNIEYGTNISKYHDGECKEFVPVNCSRYPNTTNEEGK VMLICNKDLSPVCGTDGVTYDNECLLCAHNLEPGTSVGKKYDGECKKEIATV DCSDYPKPVCSLESMPLCGSDNKTYSNKCNFCNAVVDSNETLTLSHFGKC |
| Ovomucoid [*Balearica regulorum gibbericeps*] | SEQ ID NO: 22 | MTMAGVFVLLSFALCCFPDAAFGVEVDCSTYPNTTNEEGKEVLVCTKILSPIC GTDGVTYSNECLLCAYNIEYGTNVSKDHDGECKEVVPVDCSRYPNSTNEEGK VVMLCSKDLNPVCGTDGVTYDNECVLCAHNVESGTSVGKKYDGECKKETA TVDCSDYPKPACTLEYMPFCGSDSKTYSNKCNFCNAVVDSNGTLTLSHFGKC |
| Turkey vulture [*Cathartes aura*] OVD (native sequence) bolded is native signal sequence | SEQ ID NO: 23 | MTTAGVFVLLSFALCSFPDAAFGVEVDCSTYPNTTNEEGKEVLVCTKILSPI CGTDGVTYSNECLLCAYNIEYGTNVSKDHDGECKEFVPVDCSRYPNTTNEDG KVVLLCNKDLSPICGTDGVTYDNECLLCARNLEPGTSVGKKYDGECKKEIAT VDCSDYPKPVCSLEYMPLCGSDKTYSNKCNFCNAVVDSNGTLTLSHFGKC |
| Ovomucoid-like [*Cuculus canorus*] | SEQ ID NO: 24 | MTTAGVFVLLSFTLCSFPDAAFGVEVDCSPYPNTTNEEGKEVLVCNKILSPICG TDGVTYSNECLLCAYNLEYGTNISKDYDGECKEVAPVDCSRHPNTTNEEGKV ELLCNKDLNPICGTNGVTYDNECLLCARNLESGTSIGKKYDGECKKEIATVDC SDYPKPVCTLEEMPLCGSDNKTYGNKCNFCNAVVDSNGTLTLSHFGKC |
| Ovomucoid [*Antrostomus carolinensis*] | SEQ ID NO: 25 | MTTAVVFVLLSFALCCFPDAAFGVEVDCSTYPNSTNEEGKDVLVCPKILGPIC GTDGVTYSNECLLCAYNIQYGTNVSKDHDGECKEIVPVDCSRYPNTTNEEGK VVFLCNKNFDPVCGTDGDTYDNECMLCARSLEPGTTVGKKHDGECKREIAT VDCSDYPKPTCSAEDMPLCGSDKTYSNKCNFCNAVVDSNGTLTLSRFGKC |
| Ovomucoid [*Cariama cristata*] | SEQ ID NO: 26 | MTMTGVFVLLSFAICCFPDAAFGVEVDCSTYPNTTNEEGKEVLVCTKILSPICG TDGVTYSNECLLCAYNIEYGTNVSKDHDGECKEVVPVDCSKYPNTTNEEGKV VLLCSKDLSPVCGTDGVTYDNECLLCARNLEPGSSVGKKYDGECKKEIATIDC SDYPKPVCSLEYMPLCGSDSKTYDNKCNFCNAVVDSNGTLTLSHFGKC |
| Ovomucoid-like isoform X2 [*Pygoscelis adeliae*] | SEQ ID NO: 27 | MTTAGVFVLLSFVLCCFPDAVFGVEVDCSTYPNTTNEEGKEVLVCTKILSPIC GTDGVTYSNECLLCAYNIEYGTNVSKDHDGECKEVVPVNCSRYPNTTNEEGK VVLRCSKDLSPVCGTDGVTYDNECLMCARNLEPGAVVGKNYDGECKKEIAT VDCSDYPKPVCSLEYMPLCGSDKTYSNKCNFCNAVVDSNGTLTLSHFGKC |

TABLE 1-continued

Sequences

| Sequence Description | SEQ ID NOs | SEQUENCES |
|---|---|---|
| Ovomucoid-like [Nipponia nippon] | SEQ ID NO: 28 | MTTAGVFVLLSIALCCFPDAAFGVEVDCSAYSNTTSEEGKEVLSCTKILSPICG TDGVTYSNECLLCAYNIEYGTNISKDHDGECKEVVSVDCSRYPNTTNEEGKA VLLCNKDLSPVCGTDGVTYDNECLLCAHNLEPGTSVGKKYDGACKKEIATV DCSDYPKPVCTLEYLPLCGSDSKTYSNKCDFCNAVVDSNGTLTLSHFGKC |
| Ovomucoid-like [Phaethon lepturus] | SEQ ID NO: 29 | MTTAGVFVLLSFALCCFPDAAFGVEVDCSTYPNTTNEEGKEVLVCTKILSPIC GTDGTTYSNECLLCAYNIEYGTNVSKDHDGECKVVPVDCSKYPNTTNEDGK VVLLCNKALSPICGTDRVTYDNECLMCAHNLEPGTSVGKKHDGECQKEVAT VDCSDYPKPVCSLEYMPLCGSDGKTYSNKCNFCNAVVNSNGTLTLSHFEKC |
| Ovomucoid-like isoform X1 [Melopsittacus undulatus] | SEQ ID NO: 30 | MTTAGVFVLLSFVLCCFFPDAAFGVEVDCSTYPNTTNEEGKEVLVCAKILSPV CGTDGVTYSNECLLCAHNIENGTNVGKDHDGKCKEAVPVDCSRYPNTTDEE GKVVLLCNKDVSPVCGTDGVTYDNECLLCAHNLEAGTSVDKKNDSECKTED TTLAAVSVDCSDYPKPVCTLEYLPLCGSDNKTYSNKCRFCNAVVDSNGTLTL SRFGKC |
| Ovomucoid [Podiceps cristatus] | SEQ ID NO: 31 | MTTAGVFVLLSFALCCSPDAAFGVEVDCSTYPNTTNEEGKEVLACTKILSPIC GTDGVTYSNECLLCAYNMEYGTNVSKDHDGKCKEVVPVDCSRYPNTTNEEG KVVLLCNKDLSPVCGTDGVTYDNECLLCARNLEPGASVGKKYDGECKKEIA TVDCSDYPKPVCSLEHMPLCGSDSKTYSNKCTFCNAVVDSNGTLTLHFGKC |
| Ovomucoid-like [Fulmarus glacialis] | SEQ ID NO: 32 | MTTAGVFVLLSFALCCFPDAAFGVEVDCSTYPNTTNEEGREVLVCTKILSPIC GTDGVTYSNECLLCAYNIEYGTNVSKDHDGECKEVAPVGCSRYPNTTNEEGK VVLLCNKDLSPVCGTDGVTYDNECLLCARHLEPGTSVGKKYDGECKKEIATV DCSDYPKPVCSLEYMPLCGSDSKTYSNKCNFCNAVLDSNGTLTLSHFGKC |
| Ovomucoid [Aptenodytes forsteri] | SEQ ID NO: 33 | MTTAGVFVLLSFALCFPDAVFGVEVDCSTYPNTTNEEGKEVLVCTKILSPIC GTDGVTYSNECLLCAYNIEYGTNVSKDHDGECKEVVPVDCSRYPNTTNEEGK VVLRCNKDLSPVCGTDGVTYDNECLMCARNLEPGAIVGKKYDGECKKEIAT VDCSDYPKPVCSLEYMPLCGSDSKTYSNKCNFCNAVVDSNGTLILSHFGKC |
| Ovomucoid-like isoform X1 [Pygoscelis adeliae] | SEQ ID NO: 34 | MTTAGVFVLLSFVLCCFPDAVFGVEVDCSTYPNTTNEEGKEVLVCTKILSPIC GTDGVTYSNECLLCAYNIEYGTNVSKDHDGECKEVVPVDCSRYPNTTNEEGK VVLRCSKDLSPVCGTDGVTYDNECLMCARNLEPGAVVGKNYDGECKKEIAT VDCSDYPKPVCSLEYMPLCGSDSKTYSNKCNFCNAVVDSNGTLTLSHFGKC |
| Ovomucoid isoform X1 [Aptenodytes forsteri] | SEQ ID NO: 35 | MSSQNQLPSRCRPLPGSQDLNKYYQPHCTGDRFCWLFYVTVEQFRHCICIYLQ LALERPSHEQSGQPADSRNTSTMTTAGVFVLLSFALCCFPDAVFGVEVDCST PNTTNEEGKEVLVCTKILSPICGTDGVTYSNECLLCAYNIEYGTNVSKDHDGE CKEVVPVDCSRYPNTTNEEGKVVLRCNKDLSPVCGTDGVTYDNECLMCARN LEPGAIVGKKYDGECKKEIATVDCSDYPKPVCSLEYMPLCGSDSKTYSNKCN FCNAVVDSNGTLILSHFGKC |
| Ovomucoid, partial [Antrostomus carolinensis] | SEQ ID NO: 36 | MTTAVVFVLLSFALCCFPDAAFGVEVDCSTYPNSTNEEGKDVLVCPKILGPIC GTDGVTYSNECLLCAYNIQYGTNVSKDHDGECKEIVPVDCSRYPNTTNEEGK VVFLCNKNFDPVCGTDGDTYDNECMLCARSLEPGTTVGKKHDGECKREIAT VDCSDYPKPTCSAEDMPLCGSDSKTYSNKCNFCNAVV |
| rOVD as expressed in pichia secreted form 1 | SEQ ID NO: 37 | EAEAAEVDCSRFPNATDKEGKDVLVCNKDLRPICGTDGVTYTNDCLLCAYSI EFGTNISKEHDGECKETVPMNCSSYANTTSEDGKVMVLCNRAFNPVCGTDGV TYDNECLLCAHKVEQGASVDKRHDGGCRKELAAVSVDCSEYPKPDCTAEDR PLCGSDNKTYGNKCNFCNAVVESNGTLTLSHFGKC |
| rOVD as expressed in pichia secreted form 2 | SEQ ID NO: 38 | EEGVSLEKREAEAAEVDCSRFPNATDKEGKDVLVCNKDLRPICGTDGVTYTN DCLLCAYSIEFGTNISKEHDGECKETVPMNCSSYANTTSEDGKVMVLCNRAF NPVCGTDGVTYDNECLLCAHKVEQGASVDKRHDGGCRKELAAVSVDCSEYP KPDCTAEDRPLCGSDNKTYGNKCNFCNAVVESNGTLTLSHFGKC |
| rOVD [gallus] coding sequence containing an alpha mating factor signal sequence (bolded) as expressed in pichia | SEQ ID NO: 39 | MRFPSIFTAVLFAASSALAAPVNTTTEDETAQIPAEAVIGYSDLEGDFDVA VLPFSNSTNNGLLFINTTIASIAAKEEGVSLEKREAEAAEVDCSRFPNATDK EGKDVLVCNKDLRPICGTDGVTYTNDCLLCAYSIEFGTNISKEHDGECKETVP MNCSSYANTTSEDGKVMVLCNRAFNPVCGTDGVTYDNECLLCAHKVEQGA SVDKRHDGGCRKELAAVSVDCSEYPKPDCTAEDRPLCGSDNKTYGNKCNFC NAVVESNGTLTLSHFGKC |
| Turkey vulture OVD coding sequence | SEQ ID NO: 40 | MRFPSIFTAVLFAASSALAAPVNTTTEDETAQIPAEAVIGYSDLEGDFDVA VLPFSNSTNNGLLFINTTIASIAAKEEGVSLEKREAEAVEVDCSTYPNTTNE EGKEVLVCTKILSPICGTDGVTYSNECLLCAYNIEYGTNVSKDHDGECKEFVP |

TABLE 1-continued

Sequences

| Sequence Description | SEQ ID NOs | SEQUENCES |
|---|---|---|
| containing secretion signals as expressed in pichia bolded is an alpha mating factor signal sequence | | VDCSRYPNTTNEDGKVVLLCNKDLSPICGTDGVTYDNECLLCARNLEPGTSV GKKYDGECKKEIATVDCSDYPKPVCSLEYMPLCGSDSKTYSNKCNFCNAVV DSNGTLTLSHFGKC |
| Turkey vulture OVD in secreted form expressed in Pichia | SEQ ID NO: 41 | EAEAVEVDCSTYPNTTNEEGKEVLVCTKILSPICGTDGVTYSNECLLCAYNIE YGTNVSKDHDGECKEFVPVDCSRYPNTTNEDGKVVLLCNKDLSPICGTDGVT YDNECLLCARNLEPGTSVGKKYDGECKKEIATVDCSDYPKPVCSLEYMPLCG SDSKTYSNKCNFCNAVVDSNGTLTLSHFGKC |
| Humming bird OVD (native sequence) bolded is the native signal sequence | SEQ ID NO: 42 | MTMAGVFVLLSFILCCFPDTAFGVEVDCSIYPNTTSEEGKEVLVCTETLSPIC GSDGVTYNNECQLCAYNVEYGTNVSKDHDGECKEIVPVDCSRYPNTTEEGR VVMLCNKALSPVCGTDGVTYDNECLLCARNLESGTSVGKKFDGECKKEIAT VDCTDYPKPVCSLDYMPLCGSDSKTYSNKCNFCNAVMDSNGTLTLNHFGKC |
| Humming bird OVD coding sequence as expressed in Pichia bolded is an alpha mating factor signal sequence | SEQ ID NO: 43 | MRFPSIFTAVLFAASSALAAPVNTTTEDETAQIPAEAVIGYSDLEGDFDVA VLPFSNSTNNGLLFINTTIASIAAKEEGVSLDKREAEAVEVDCSIYPNTTSEE GKEVLVCTETLSPICGSDGVTYNNECQLCAYNVEYGTNVSKDHDGECKEIVP VDCSRYPNTTEEGRVVMLCNKALSPVCGTDGVTYDNECLLCARNLESGTSV GKKFDGECKKEIATVDCTDYPKPVCSLDYMPLCGSDSKTYSNKCNFCNAVM DSNGTLTLNHFGKC |
| Humming bird OVD in secreted form from Pichia | SEQ ID NO: 44 | EAEAVEVDCSIYPNTTSEEGKEVLVCTETLSPICGSDGVTYNNECQLCAYNVE YGTNVSKDHDGECKEIVPVDCSRYPNTTEEGRVVMLCNKALSPVCGTDGVT YDNECLLCARNLESGTSVGKKFDGECKKEIATVDCTDYPKPVCSLDYMPLCG SDSKTYSNKCNFCNAVMDSNGTLTLNHFGKC |
| rOVL as expressed in pichia bolded is an alpha mating factor signal sequence | SEQ ID NO: 45 | MRFPSIFTAVLFAASSALAAPVNTTTEDETAQIPAEAVIGYSDLEGDFDVA VLPFSNSTNNGLLFINTTIASIAAKEEGVSLDKREAEAKVFGRCELAAAMK RHGLDNYRGYSLGNWVCAAKFESNFNTQATNRNTDGSTDYGILQINSRWWC NDGRTPGSRNLCNIPCSALLSSDITASVNCAKKIVSDGNGMNAWVAWRNRCK GTDVQAWIRGCRL |
| rOVL as found after secretion from Pichia | SEQ ID NO: 46 | EAEAKVFGRCELAAAMKRHGLDNYRGYSLGNWVCAAKFESNFNTQATNRN TDGSTDYGILQINSRWWCNDGRTPGSRNLCNIPCSALLSSDITASVNCAKKIVS DGNGMNAWVAWRNRCKGTDVQAWIRGCRL |
| Lysozyme (OVL) from *Gallus gallus* (without signal sequence) | SEQ ID NO: 47 | KVFGRCELAAAMKRHGLDNYRGYSLGNWVCAAKFESNFNTQATNRNTDGS TDYGILQINSRWWCNDGRTPGSRNLCNIPCSALLSSDITASVNCAKKIVSDGN GMNAWVAWRNRCKGTDVQAWIRGCRL |
| Lysozyme | SEQ ID NO: 48 | KVFGRCELAAAMKRHGLDNYRGYSLGNWVCAKFESNFNTQATNRNTDGS TDYGILQINSRWWCNDGRTPGSRNLCNIPCSALLSSDITASVNCAKKIVSDGN GMSAWVAWRNRCKGTDVQAWIRGCRL |
| Lysozyme C (Human) | SEQ ID NO: 49 | KVFERCELARTLKRLGMDGYRGISLANWMCLAKWESGYNTRATNYNAGDR STDYGIFQINSRYWCNDGKTPGAVNACHLSCSALLQDNIADAVACAKRVVRD PQGIRAWVAWRNRCQNRDVRQYVQGCGV |
| Lysozyme C (*Bos taurus*) | SEQ ID NO: 50 | KVFERCELARTLKKLGLDGYKGVSLANWLCLTKWESSYNTKATNYNPSSEST DYGIFQINSKWWCNDGKTPNAVDGCHVSCRELMENDIAKAVACAKHIVSEQ GITAWVAWKSHCRDHDVSSYVEGCTL |
| Lysozyme (OVL) from *Gallus gallus* Native secretion signal is bolded | SEQ ID NO: 51 | MRSLLILVLCFLPLAALGKVFGRCELAAAMKRHGLDNYRGYSLGNWVCAA KFESNFNTQATNRNTDGSTDYGILQINSRWWCNDGRTPGSRNLCNIPCSALLS SDITASVNCAKKIVSDGNGMNAWVAWRNRCKGTDVQAWIRGCRL |
| OCH1:EndoH fusion protein | SEQ ID NO: 52 | MAKADGSLLYYNPHNPPRRYYFYMAIFAVSVICVLYGPSQQLSSPKIDASAPA PVKQGPTSVAYVEVNNNSMLNVGKYTLADGGGNAFDVAVIFAANINYDTGT KTAYLHFNENVQRVLDNAVTQIRPLQQQGIKVLLSVLGNHQGAGFANPPSQQ AASAFAKQLSDAVAKYGLDGVDFDDEYAEYGNNGTAQPNDSSFVHLVTALR ANMPDKIISLYNIGPAASRLSYGGVDVSDKFDYAWNPYYGTWQVPGIALPKA QLSPAAVEIGRTSRSTVADLARRTVDEGYGVYLTYNLDGGDRTADVSAFTRE LYGSEAVRTP |

An rOVD or rOVL can include additional sequences. Expression of rOVD and rOVL in a host cell, for instance a *Pichia* species, a *Saccharomyces* species, a *Trichoderma* species, a *Pseudomonas* species may lead to an addition of peptides to the OVD or OVL sequence as part of post-transcriptional or post-translational modifications. Such peptides may not be part of the native OVD or OVL sequences. For instance, expressing an OVD sequence in a *Pichia* species, such as *Komagataella phaffii* and *Komagataella pastoris* may lead to addition of a peptide at the N-terminus or C-terminus. In some cases, a tetrapeptide EAEA (SEQ ID NO: 53) is added to the N-terminus of the OVD sequence upon expression in a host cell. In some embodiments, rOVD or rOVL or both include the amino acids EAEA at the N-terminus. An OVD or OVL protein sequence can include a signal sequence, such as for directing secretion from a host cell. In some cases, the signal sequence may be a native signal sequence. In some cases, a signal sequence may be a heterologous signal sequence. For instance, an alpha mating factor signal sequence can be fused to an OVD or OVL sequence for expression and secretion in a yeast cell such as a *Pichia* sp. In some cases, the signal sequence is removed in whole or in part when the protein, such as an rOVD or rOVL, is secreted from the host cell.

An rOVD and/or rOVL can be a non-naturally occurring variant of an OVD and/or OVL. Such variant can comprise one or more amino acid insertions, deletions, or substitutions relative to a native OVD or native OVL sequence.

Such an rOVD variant can have at least 70%, 75%, 80%, 85%, 90%, 95%, 96%, 97%, 98%, or 99% sequence identity to SEQ ID NOs: 1-44. A rOVL variant can have at least 70%, 75%, 80%, 85%, 90%, 95%, 96%, 97%, 98%, or 99% sequence identity to SEQ ID NOs: 45-51. The term "sequence identity" as used herein in the context of amino acid sequences is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

In some embodiments, a variant is one that confers additional features, such as reduced allergenicity. For example, an rOVD can include G162M and/or F167A (such as in SEQ ID NO: 3) relative to a wild type OVD sequence SEQ ID NO: 2 and have reduced allergenicity as compared to the wild type OVD sequence.

Depending on the host organism used to express the rOVD and/or rOVL, the rOVD and/or rOVL can have a glycosylation, acetylation, or phosphorylation pattern different from wildtype OVD (e.g., native OVD) or wildtype OVL (e.g., native OVL). For example, the rOVD and/or rOVL herein may or may not be glycosylated, acetylated, or phosphorylated. An rOVD and/or rOVL may have an avian, non-avian, microbial, non-microbial, mammalian, or non-mammalian glycosylation, acetylation, or phosphorylation pattern.

An rOVD and/or rOVL is recombinantly expressed in a host cell. As used herein, a "host" or "host cell" denotes here any protein production host selected or genetically modified to produce a desired product. Exemplary hosts include fungi, such as filamentous fungi, as well as bacteria, yeast, plant, insect, and mammalian cells. A host cell may be *Arxula* spp., *Arxula adeninivorans*, *Kluyveromyces* spp., *Kluyveromyces lactis*, *Komagataella phaffii*, *Pichia* spp., *Pichia angusta*, *Pichia pastoris*, *Saccharomyces* spp., *Saccharomyces cerevisiae*, *Schizosaccharomyces* spp., *Schizosaccharomyces pombe*, *Yarrowia* spp., *Yarrowia lipolytica*, *Agaricus* spp., *Agaricus bisporus*, *Aspergillus* spp., *Aspergillus awamori*, *Aspergillus fumigatus*, *Aspergillus nidulans*, *Aspergillus niger*, *Aspergillus oryzae*, *Bacillus subtilis*, *Colletotrichum* spp., *Colletotrichum gloeosporiodes*, *Endothia* spp., *Endothia parasitica*, *Escherichia coli*, *Fusarium* spp., *Fusarium graminearum*, *Fusarium solani*, *Mucor* spp., *Mucor miehei*, *Mucor pusillus*, *Myceliophthora* spp., *Myceliophthora thermophila*, *Neurospora* spp., *Neurospora crassa*, *Penicillium* spp., *Penicillium camemberti*, *Penicillium canescens*, *Penicillium chrysogenum*, *Penicillium (Talaromyces) emersonii*, *Penicillium funiculo sum*, *Penicillium purpurogenum*, *Penicillium roqueforti*, *Pleurotus* spp., *Pleurotus ostreatus*, *Rhizomucor* spp., *Rhizomucor miehei*, *Rhizomucor pusillus*, *Rhizopus* spp., *Rhizopus arrhizus*, *Rhizopus oligosporus*, *Rhizopus oryzae*, *Trichoderma* spp., *Trichoderma altroviride*, *Trichoderma reesei*, or *Trichoderma vireus*. A host cell can be an organism that is approved as generally regarded as safe by the U.S. Food and Drug Administration.

A recombinant protein can be recombinantly expressed in yeast, filamentous fungi or a bacterium. In some embodiments, recombinant protein is recombinantly expressed in a *Pichia* species (*Komagataella phaffii* and *Komagataella pastoris*), a *Saccharomyces* species, a *Trichoderma* species, a *Trichoderma* species, a *Pseudomonas* species or an *E. coli* species.

A host cell may be transformed to include one or more expression cassettes. As examples, a host cell may be transformed to express one expression cassette, two expression cassettes, three expression cassettes or more expression cassettes.

In some cases, rOVD and/or rOVL may be deglycosylated or modified in its glycosylation (e.g., chemically, enzymatically through endoglucanases (such as EndoH), endoglycosidases, mannosidases (such as alpha-1,2 mannosidase), PNGase F, β-Glycosidase, OCH1, Neuraminidase, β,1-4 Galactosidase, β-N-acetylglucosaminidases, etc.), deacetylated (e.g., protein deacetylase, histone deacetylase, sirtuin), or dephosphorylated (e.g., acid phosphatase, lambda protein phosphatase, calf intestinal phosphatase, alkaline phosphatase). Deglycosylation, deacetylation or dephosphorylation may produce a protein that is more uniform or is capable of producing a composition with less variation.

The present disclosure contemplates modifying glycosylation of the recombinant OVD to alter or enhance one or more functional characteristics of the protein and/or its production. A host cell may comprise heterologous enzymes that modify the glycosylation pattern of ovomucoid. In some cases, one or more enzymes may be used for modifying the glycosylation of rOVD protein. The enzymes used modifying glycosylation of rOVD may be an enzyme or a fusion protein comprising an enzyme or active fragment of an enzyme, for example EndoH or a fusion of OCH1 to EndoH (such as to provide for Golgi retention of the EndoH enzyme) may be provided in a host cell.

Native ovomucoid (nOVD), such as isolated from a chicken or other avian egg, has a highly complex branched form of glycosylation. The glycosylation pattern comprises N-linked glycan structures such as N-acetylglucosamine units and N-linked mannose units. See, e.g., FIG. 1B (left-hand column). In some cases, the rOVD for use in a herein disclosed consumable composition and produced using the methods described herein has a glycosylation pattern which is different than the glycosylation pattern of nOVD. For example, when rOVD is produced in a *Pichia* sp., the protein may be highly glycosylated. FIG. 1C illustrates the glycosylation patterns of rOVD produced by *P. pastoris*, showing a complex branched glycosylation pattern. In some embodiments of the compositions and methods herein, rOVD is treated such that the glycosylation pattern is modified from that of nOVD and also modified as compared to rOVD produced by a *Pichia* sp. without such treatment. In some cases, the rOVD has no glycosylation. In other cases, the rOVD has reduced glycosylation. In some cases, the rOVD is modified by N-acetylglucosamine at one or more asparagine residues of the protein and lacks or is substantially devoid of N-linked mannosylation. See, e.g., FIG. 1B (right hand column). The changes in glycosylation described herein may lead to an increase in the solubility and clarity of rOVD as compared to other forms of protein such as whey proteins, soy proteins, pea proteins, and nOVD.

In some cases, an enzyme used for modifying glycosylation may be transformed into a host cell. In some cases, the enzyme used for modifying glycosylation may be transformed into the same host cell that produces rOVD. In some cases, the enzyme may be provided transiently to the host cell, such as by an inducible expression system. In some cases, when a host cell expresses an enzyme used for modifying glycosylation, the recombinant protein (e.g., rOVD and rOVL) is secreted from the host cell in the modified state.

In one example, a host cell producing OVD comprises a fusion of EndoH and OCH1 enzymes. An exemplary OCH1-EndoH protein sequence is provided as SEQ ID No: 52. In such cases, an rOVD produced from the host cell comprises a glycosylation pattern substantially different from an rOVD which is produced in a cell without such enzymes. The rOVD produced in such cases is also substantially different as compared to a native OVD (e.g., produced by a chicken or other avian egg). FIG. 1B shows a comparison of nOVD (with mannose residues) and rOVD glycosylation patterns wherein the rOVD was treated with EndoH and comprises an N-acetylglucosamine residue at the asparagine but no mannose residues. FIG. 1C shows the glycosylation pattern of rOVD produced in a host cell such as *P. pastoris* and where rOVD was not treated with EndoH and has both N-acetylglucosamine resides as well as the chains of N-linked mannose residues. Modification of the glycosylation of rOVD may provide nutritional benefits to rOVD, such as a higher nitrogen to carbon ratio, and may improve the clarity and solubility of the protein. In some cases, the modification of the glycosylation of rOVD is performed within the host cell that produces rOVD before the rOVD is secreted from the host cell and/or before isolating the rOVD. In some cases, modification of the glycosylation of rOVD is performed after its secretion and/or after isolating rOVD from the host cell.

The molecular weight or rOVD may be different as compared to nOVD. The molecular weight of the protein may be less than the molecular weight of nOVD or less than rOVD produced by the host cell where the glycosylation of rOVD is not modified. In embodiments, the molecular weight of an rOVD may be between 20 kDa and 40 kDa. In some cases, an rOVD with modified glycosylation has a different molecular weight, such as compared to a native OVD (as produced by an avian host species) or as compared to a host cell that glycosylates the rOVD, such as where the rOVD includes N-linked mannosylation. In some cases, the molecular weight of rOVD is greater than the molecular weight of the rOVD that is completely devoid of post-translational modifications. or an rOVD that lacks all forms of N-linked glycosylation.

Expression of an rOVD or rOVL can be provided by an expression vector, a plasmid, a nucleic acid integrated into the host genome or other means. For example, a vector for expression can include: (a) a promoter element, (b) a signal peptide, (c) a heterologous OVD or OVL sequence, and (d) a terminator element.

Expression vectors that can be used for expression of OVD and OVL include those containing an expression cassette with elements (a), (b), (c) and (d). In some embodiments, the signal peptide (c) need not be included in the vector. In general, the expression cassette is designed to mediate the transcription of the transgene when integrated into the genome of a cognate host microorganism.

To aide in the amplification of the vector prior to transformation into the host microorganism, a replication origin (e) may be contained in the vector (such as PUC_ORIC and PUC (DNA2.0)). To aide in the selection of microorganism stably transformed with the expression vector, the vector may also include a selection marker (f) such as URA3 gene and Zeocin resistance gene (ZeoR). The expression vector may also contain a restriction enzyme site (g) that allows for linearization of the expression vector prior to transformation into the host microorganism to facilitate the expression vectors stable integration into the host genome. In some embodiments the expression vector may contain any subset of the elements (b), (e), (f), and (g), including none of elements (b), (e), (f), and (g). Other expression elements and vector element known to one of skill in the art can be used in combination or substituted for the elements described herein.

Exemplary promoter elements (a) may include, but are not limited to, a constitutive promoter, inducible promoter, and hybrid promoter. Promoters include, but are not limited to, acu-5, adh1+, alcohol dehydrogenase (ADH1, ADH2, ADH4), AHSB4m, AINV, alcA, α-amylase, alternative oxidase (AOD), alcohol oxidase I (AOX1), alcohol oxidase 2 (AOX2), AXDH, B2, CaMV, cellobiohydrolase I (cbh1), ccg-1, cDNA1, cellular filament polypeptide (cfp), cpc-2, ctr4+, CUP1, dihydroxyacetone synthase (DAS), enolase (ENO, ENO1), formaldehyde dehydrogenase (FLD1), FMD, formate dehydrogenase (FMDH), G1, G6, GAA, GAL1, GAL2, GAL3, GAL4, GAL5, GAL6, GAL7, GAL8, GAL9, GAL10, GCW14, gdhA, gla-1, α-glucoamylase (glaA), glyceraldehyde-3-phosphate dehydrogenase (gpdA, GAP, GAPDH), phosphoglycerate mutase (GPM1), glycerol kinase (GUT1), HSP82, invl+, isocitrate lyase (ICL1), acetohydroxy acid isomeroreductase (ILV5), KAR2, KEX2, β-galactosidase (lac4), LEU2, melO, MET3, methanol oxidase (MOX), nmt1, NSP, pcbC, PET9, peroxin 8 (PEX8), phosphoglycerate kinase (PGK, PGK1), pho1, PHO5, PHO89, phosphatidylinositol synthase (PIS1), PYK1, pyruvate kinase (pki1), RPS7, sorbitol dehydrogenase (SDH), 3-phosphoserine aminotransferase (SER1), SSA4, SV40, TEF, translation elongation factor 1 alpha (TEF1), THI11, homoserine kinase (THR1), tpi, TPS1, triose phosphate isomerase (TPI), XRP2, YPT1, a sequence or subsequence chosen from SEQ ID Nos: 121 to 132, and any combination thereof. Illustrative inducible promoters include methanol-induced promoters, e.g., DAS1 and pPEX11.

A signal peptide (b), also known as a signal sequence, targeting signal, localization signal, localization sequence, signal peptide, transit peptide, leader sequence, or leader peptide, may support secretion of a protein or polynucleotide. Extracellular secretion of a recombinant or heterologously expressed protein from a host cell may facilitate protein purification. A signal peptide may be derived from a precursor (e.g., prepropeptide, preprotein) of a protein. Signal peptides can be derived from a precursor of a protein other than the signal peptides in native OVD and/or OVL.

Any nucleic acid sequence that encodes OVD and/or OVL can be used as (c). Preferably such sequence is codon optimized for the host cell.

Exemplary transcriptional terminator elements include, but are not limited to, acu-5, adh1+, alcohol dehydrogenase (ADH1, ADH2, ADH4), AHSB4m, AINV, alcA, α-amylase, alternative oxidase (AOD), alcohol oxidase I (AOX1), alcohol oxidase 2 (AOX2), AXDH, B2, CaMV, cellobiohydrolase I (cbh1), ccg-1, cDNA1, cellular filament polypeptide (cfp), cpc-2, ctr4+, CUP1, dihydroxyacetone synthase (DAS), enolase (ENO, ENO1), formaldehyde dehydrogenase (FLD1), FMD, formate dehydrogenase (FMDH), G1, G6, GAA, GAL1, GAL2, GAL3, GAL4, GAL5, GAL6, GAL7, GAL8, GAL9, GAL10, GCW14, gdhA, gla-1, α-glucoamylase (glaA), glyceraldehyde-3-phosphate dehydrogenase (gpdA, GAP, GAPDH), phosphoglycerate mutase (GPM1), glycerol kinase (GUT1), HSP82, invl+, isocitrate lyase (ICL1), acetohydroxy acid isomeroreductase (ILV5), KAR2, KEX2, β-galactosidase (lac4), LEU2, melO, MET3, methanol oxidase (MOX), nmt1, NSP, pcbC, PET9, peroxin 8 (PEX8), phosphoglycerate kinase (PGK, PGK1), pho1, PHO5, PHO89, phosphatidylinositol synthase (PIS1), PYK1, pyruvate kinase (pki1), RPS7, sorbitol dehydrogenase (SDH), 3-phosphoserine aminotransferase (SER1), SSA4, SV40, TEF, translation elongation factor 1 alpha (TEF1), THI11, homoserine kinase (THR1), tpi, TPS1, triose phosphate isomerase (TPI1), XRP2, YPT1, and any combination thereof.

Exemplary selectable markers (f) may include but are not limited to: an antibiotic resistance gene (e.g. zeocin, ampicillin, blasticidin, kanamycin, nurseothricin, chloroamphenicol, tetracycline, triclosan, ganciclovir, and any combination thereof), an auxotrophic marker (e.g. ade1, arg4, his4, ura3, met2, and any combination thereof).

In one example, a vector for expression in *Pichia* sp. can include an AOX1 promoter operably linked to a signal peptide (alpha mating factor) that is fused in frame with a nucleic acid sequence encoding OVD and/or OVL, and a terminator element (AOX1 terminator) immediately downstream of the nucleic acid sequence encoding OVD and/or OVL.

In another example, a vector comprising a DAS1 promoter is operably linked to a signal peptide (alpha mating factor) that is fused in frame with a nucleic acid sequence encoding OVD and/or OVL and a terminator element (AOX1 terminator) immediately downstream of OVD and/or OVL.

A recombinant protein described herein may be secreted from the one or more host cells. In some embodiments, rOVD and/or rOVL protein is secreted from the host cell. The secreted rOVD and/or rOVL may be isolated and purified by methods such as centrifugation, fractionation, filtration, affinity purification and other methods for separating protein from cells, liquid and solid media components and other cellular products and byproducts. In some embodiments, rOVD and/or rOVL is produced in a *Pichia* Sp. and secreted from the host cells into the culture media. The secreted rOVD and/or rOVL is then separated from other media components for further use.

In some cases, multiple vectors comprising OVD may be transfected into one or more host cells. A host cell may comprise more than one copy of OVD. A single host cell may comprise 2, 3, 4, 5, 6, 7, 8, 9 10, 11, 12, 13, 14, 15, 16, 17, 18, 19 or 20 copies of OVD. A single host cell may comprise one or more vectors for the expression of OVD. A single host cell may comprise 2, 3, 4, 5, 6, 7, 8, 9 or 10 vectors for OVD expression. Each vector in the host cell may drive the expression of OVD using the same promoter. Alternatively, different promoters may be used in different vectors for OVD expression.

The consumable products and rOVD and/or rOVL compositions herein can be essentially free of any microbial cells or microbial cell contaminants. For instance, rOVD and/or rOVL may be isolated from a culture comprising microbial growth.

rOVD may be treated chemically or enzymatically before it is purified for use in a consumable composition. Such treatments may be performed to reduce impurities in an rOVD protein composition. Such treatments may be performed to improve the sensory attributes of the rOVD protein composition. Treatments may include but are not limited to purification steps, filtration, chemical treatments, and enzymatic treatments.

In some cases, rOVD protein and compositions containing rOVD protein, including forms of rOVD with modified glycosylation (e.g., such forms with N-acetylglucosamine but lacking N-linked mannose residues) may be treated with oxidizing agent or an oxygen-generating agent to modify components of the rOVD composition, such as impurities. The oxidizing agent or oxygen-generating agent may comprise hydrogen peroxide, sodium percarbonate, activated chlorine dioxide, bubbled oxygen or ozone. The treatment may improve the solubility and clarity of an rOVD composition. The treatment may reduce the odor of an rOVD composition. The treatment may neutralize the color of an rOVD composition; for instance, the rOVD composition may lose color after a treatment, e.g., to a less intense/lighter coloration. In embodiments, the color may change form greenish to yellowish and/or from yellowish to essentially colorless.

In some examples, rOVD may be treated with an oxidizing agent or an oxygen-generating agent, e.g., hydrogen peroxide or sodium percarbonate, before it is purified for use in a consumable composition. A culture medium comprising secreted or isolated rOVD may be treated with an oxygen-generating agent, e.g., hydrogen peroxide or sodium percarbonate. Using hydrogen peroxide as an example, a hydrogen peroxide treatment may be followed by one or more wash steps and/or filtration steps to remove hydrogen peroxide from the resulting rOVD compositions. Such steps may be performed following treatments with other oxygen-generating agents, e.g., sodium percarbonate.

In some cases, the concentration of hydrogen peroxide used for treating rOVD may be from 1% to 20%. The concentration of hydrogen peroxide used for treating rOVD may be at least 1%. The concentration of hydrogen peroxide used for treating rOVD may be at most 20%. The concentration of hydrogen peroxide used for treating rOVD may be 1% to 2%, 1% to 5%, 1% to 7%, 1% to 10%, 1% to 12%, 1% to 15%, 1% to 17%, 1% to 20%, 2% to 5%, 2% to 7%, 2% to 10%, 2% to 12%, 2% to 15%, 2% to 17%, 2% to 20%, 5% to 7%, 5% to 10%, 5% to 12%, 5% to 15%, 5% to 17%, 5% to 20%, 7% to 10%, 7% to 12%, 7% to 15%, 7% to 17%, 7% to 20%, 10% to 12%, 10% to 15%, 10% to 17%, 10% to 20%, 12% to 15%, 12% to 17%, 12% to 20%, 15% to 17%, 15% to 20%, or 17% to 20% weight per total weight (w/w) and/or weight per total volume (w/v). The concentration of hydrogen peroxide used for treating rOVD may be about 1%, 2%, 5%, 7%, 10%, 12%, 15%, 17%, or 20% w/w or w/v. The concentration of hydrogen peroxide used for treating rOVD may be at least 1%, 2%, 5%, 7%, 10%, 12%, 15% or 17% w/w or w/v. The concentration of hydrogen peroxide used for treating rOVD may be at most 2%, 5%, 7%, 10%, 12%, 15%, 17%, or 20% w/w or w/v.

rOVD may be treated with hydrogen peroxide for a limited duration of time. For instance, rOVD may be exposed to hydrogen peroxide for at least 1 hour, 2 hours, 3 hours, 5 hours, 7 hours, 10 hours, 12 hours, 15 hours, 17 hours, 20 hours, 22 hours, 24 hours, 26 hours, 28 hours, 30 hours, 34 hours, 36 hours, 40 hours, 44 hours or 48 hours. Hydrogen peroxide may be added to the rOVD culture media throughout the culturing process.

rOVD may be treated with hydrogen peroxide at a pH of about 3 to 6. rOVD may be treated with hydrogen peroxide at a pH of about 3, 3.2, 3.4, 3.6, 3.8, 4, 4.1, 4.2, 4.4, 4.6, 4.8, 5, 5.2, 5.4, 5.6, 5.8 or 6. rOVD may treated with hydrogen peroxide at a pH of at least 3, 3.2, 3.4, 3.6, 3.8, 4, 4.1, 4.2, 4.4, 4.6, 4.8, 5, 5.2, 5.4, 5.6 or 5.8. rOVD may treated with hydrogen peroxide at a pH of at most 3.2, 3.4, 3.6, 3.8, 4, 4.1, 4.2, 4.4, 4.6, 4.8, 5, 5.2, 5.4, 5.6, 5.8 or 6.

rOVD may be filtered before treatment with an oxygen-generating agent. In some cases, rOVD may be filtered before and after treatment with an oxygen-generating agent.

Definitions

The terminology used herein is for the purpose of describing particular cases only and is not intended to be limiting.

As used herein, unless otherwise indicated, the terms "a", "an" and "the" are intended to include the plural forms as well as the single forms, unless the context clearly indicates otherwise.

The terms "comprise", "comprising", "contain," "containing," "including", "includes", "having", "has", "with", or variants thereof as used in either the present disclosure and/or in the claims, are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean 10% greater than or less than the stated value. In another example, "about" can mean within 1 or more than 1 standard deviation, per the practice in the given value. Where particular values are described in the application and claims, unless otherwise stated the term "about" should be assumed to mean an acceptable error range for the particular value.

The term "substantially" is meant to be a significant extent, for the most part; or essentially. In other words, the term substantially may mean nearly exact to the desired attribute or slightly different from the exact attribute. Substantially may be indistinguishable from the desired attribute. Substantially may be distinguishable from the desired attribute but the difference is unimportant or negligible.

Any aspect or embodiment described herein can be combined with any other aspect or embodiment as disclosed herein.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Expression Constructs, Transformation, Protein Purification and Processing Two expression constructs were created for expression of OVD (SEQ ID NO: 1) in *Pichia pastoris*. The first construct included the Alcohol oxidase 1 (AOX1) promoter. An OVD coding sequenced was fused in-frame with the alpha mating factor signal sequence downstream of the promoter sequence. A transcriptional terminator from the AOX1 gene was placed downstream of the OVD sequence. The expression construct was placed into a Kpas-URA 3 vector.

A second expression construct was created containing the methanol-inducible DAS1 promoter (ATCC No. 28485) upstream of the alpha mating factor signal sequence fused in frame with a nucleic acid sequence encoding the same OVD protein sequence as in the first expression construct. A transcriptional terminator from the AOX1 gene was placed downstream of the OVD sequence.

In both expression constructs, the OVD sequence was that of chicken (*Gallus gallus*) having amino acid sequence of SEQ ID NO: 1.

Both expression constructs were transformed into *Pichia pastoris*. Successful integration of the two constructs were confirmed by genomic sequencing.

Fermentation: Recombinant OVD (rOVD) from each expression construct was produced in a bioreactor at ambient conditions. A seed train for the fermentation process began with the inoculation of shake flasks with liquid growth broth. The inoculated shake flasks were kept in a shaker after which the grown *Pichia pastoris* was transferred to a production scale reactor.

The culture was grown at 30° C., at a set pH and dissolved oxygen (DO). The culture was fed with a carbon source.

Secreted rOVD was purified by separating cells from the liquid growth broth, performing multiple filtration steps, performing chromatography using and drying the final protein product to produce pure rOVD powder.

Example 2: Expression Construct, Transformation, Protein Purification and Processing Three expression constructs were created for expression of a mature form of OVD (SEQ D NO: 1) in *Pichia pastoris*. The first construct included the AOX1 promoter. An OVD coding sequenced was fused in-frame with the alpha mating factor signal sequence downstream of the promoter sequence (SEQ ID NO: 39). A transcriptional terminator from the AOX1 gene was placed downstream of the OVD sequence. The host cells had eleven copies of OVD, ten of which were in the hybrid promoter system, with five driven by a shortened pAOX1. The eleventh copy was driven by a full-sized pAOX1 promoter.

A second expression construct was created containing a nucleic acid encoding the *P. pastoris* transcription factor HAC1 under the control of a strong methanol-inducible promoter. A transcriptional terminator from the AOX1 gene was placed downstream of the HAC1 sequence.

A third expression construct was created encoding a fusion protein. The construct comprises a nucleic acid that encodes the first 48 residues of *Pichia* OCH1 protein fused to a catalytically active version of the *Streptomyces coelicoflavus* EndoH (SEQ ID NO.: 52) and under a strong methanol-inducible promoter, pPEX11. A transcriptional terminator from the AOX1 gene was placed downstream of the EndoH-OCH1 fusion protein sequence.

The *P. pastoris* strain was modified to remove cytoplasmic killer plasmids and then further modified to have a deletion in the AOX1 gene. This deletion generated a methanol-utilization slow (mutS) phenotype that reduces the strain's ability to consume methanol. This base strain was transformed with the three expression constructs.

Linear cassettes of methanol-inducible promoter: ScPre-Pro (*Saccharomyces* pre-pro sequence)::ovomucoid:: AOX1term; linear cassettes of methanol-inducible promoter::HAC1::AOX1term; and a linear cassette of methanol-inducible promoter::EndoH-OCH1::AOX1term were introduced into the base *P. pastoris* strain using standard electroporation methods. FIG. 1A illustrates the vector constructs used for the expression of rOVD.

Fermentation: Recombinant OVD from each expression construct was produced in a bioreactor at ambient conditions. A seed train for the fermentation process began with the inoculation of shake flasks with liquid growth broth. The inoculated shake flasks were kept in a shaker after which the grown *P. pastoris* was transferred to a production-scale reactor.

The culture was grown at 30° C., at a set pH and dissolved oxygen (DO). The culture was fed with a carbon source.

To expand production, an rOVD *P. pastoris* seed strain is removed from cryo-storage and thawed to room temperature. Contents of the thawed seed vials are used to inoculate liquid seed culture media in baffled flasks which were grown at 30° C. in shaking incubators. These seed flasks are then transferred and grown in a series of larger and larger seed fermenters (number to vary depending on scale) containing a basal salt media, trace metals, and glucose. Temperature in the seed reactors are controlled at 30° C., pH at 5, and DO at 30%. pH is maintained by feeding ammonia hydroxide which also acts as a nitrogen source. Once sufficient cell mass is reached, the grown rOVD *P. pastoris* is inoculated in a production-scale reactor containing basal salt media, trace metals, and glucose. Like in the seed tanks, the culture is also controlled at 30° C., pH 5 and 30% DO throughout the process. pH is again maintained by feeding ammonia hydroxide. During the initial batch glucose phase, the culture is left to consume all glucose and subsequently-produced ethanol. Once the target cell density is achieved and glucose and ethanol concentrations are confirmed to be zero, the glucose fed-batch growth phase is initiated. In this phase, glucose is fed until the culture reaches a target cell density. Glucose is fed at a limiting rate to prevent ethanol from building up in the presence of non-zero glucose concentrations. In the final induction phase, the culture is co-fed glucose and methanol which induces it to produce rOVD. Glucose is fed at an amount to produce a desired growth rate, while methanol is fed to maintain the methanol concentration at 1% to ensure that expression is consistently induced. Regular samples are taken throughout the fermentation process for analyses of specific process parameters (e.g., cell density, glucose/methanol concentrations, product titer, and quality). After a designated amount of fermentation time, secreted rOVD is collected and transferred for downstream processing.

The rOVD products were purified by separating cells from the liquid growth broth, performing multiple filtration steps, performing chromatography, and/or drying the final protein product to produce pure rOVD powder.

Post-translation modification from the OCH1-EndoH fusion protein resulted in the removal of the alpha factor pre-pro sequence. N-terminal sequencing results showed imprecise cleavage of the N-terminal pro sequence by the *Pichia* host post-transcription machinery fusing an additional four amino acid residues (major) or 6 amino acid residues (minor) to the N-terminus of the produced rOVD (SEQ ID NO: 37) or (SEQ ID NO:38) in comparison to the amino acid sequence of mature OVD (SEQ ID NO:1).

Figure 1D:
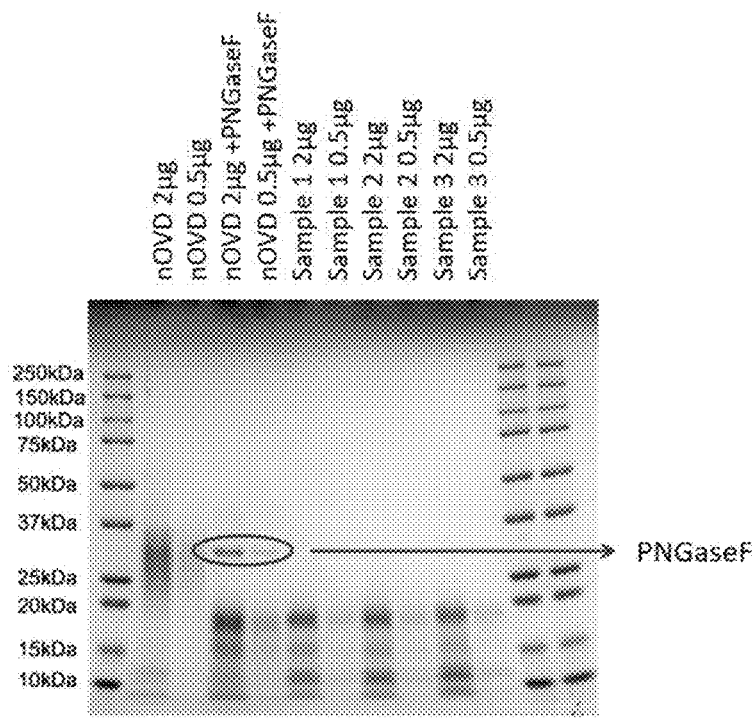
FIG. 1D compares the molecular weight of native OVD, native OVD treated with an endoglycosidase, and recombinant OVD samples.

The molecular weight of rOVD from *Pichia* was compared against native chicken ovomucoid (nOVD) using SDS-PAGE. The rOVD showed a difference in migration. To ascertain whether the difference in gel migration was due to differential post-translational glycosylation, deglycosylated native ovomucoid was treated with PNGase F, an enzyme that specifically deglycosylates proteins (BioLabs 2020), and compared to the rOVD sample. The deglycosylated native ovomucoid (nOVD+PNGaseF) displayed the same band patterns and molecular weight as three rOVD samples tested (FIG. 1D). The difference in glycosylation is attributed to the action of the OCH1-EndoH in the *Pichia* strain, such that rOVD has only the core N-acetylglucosamine unit attached to the Asn residue instead of the complex branched glycosylation (that includes mannose) of nOVD from chicken egg white (FIG. 1B and FIG. 1C).

Mass spectrometry analysis of rOVD expressed in *Pichia* without EndoH is shown to have eight different N-glycan structures (FIG. 1C). The structures include Man9 GlcNAc2, Man9 GlcNAc2 Hex, Man9 GlcNAc2Hex2, Man9 GlcNAc2Hex3, Man9 GlcNAc2Hex4, Man9 GlcNAc2 Hex5,v Man9 GlcNAc2Hex6, and Man9 GlcNAc2 Hex7. Table 2 below shows the percentage of N-linked glycans on the rOVD sample produced without endoglycosidase treatment.

TABLE 2

N-linked glycans from sample detected by MALDI TOF/TOF MS.

| Permethylated mass (m/z)[1] | Text description of structures | Percentage |
|---|---|---|
| 2396.2 | $Man_9\ GlcNAc_2$ | 5.6 |
| 2600.3 | $Man_9\ GlcNAc_2\ Hex$ | 25.1 |
| 2804.4 | $Man_9\ GlcNAc_2\ Hex_2$ | 31.6 |
| 3008.5 | $Man_9\ GlcNAc_2\ Hex_3$ | 18.2 |
| 3212.6 | $Man_9\ GlcNAc_2\ Hex_4$ | 6.0 |
| 3416.7 | $Man_9\ GlcNAc_2\ Hex_5$ | 7.2 |
| 3620.8 | $Man_9\ GlcNAc_2\ Hex_6$ | 3.8 |
| 3824.9 | $Man_9\ GlcNAc_2\ Hex_7$ | 2.6 |

Example 3: Solubility and Clarity Testing at Varying rOVD Concentrations

Lyophilized rOVD (from Example 2) was blended into aqueous solution (distilled water) at different concentrations and pHs. Clarity and solubility of the rOVD solutions was then assessed visually (e.g., for turbidity, precipitate, viscosity, and color) as well as by measuring absorbance at 600 nm.

FIG. 2 shows the absorbance at 600 nm of deionized water compared with the absorbance at 600 nm of a solution comprising rOVD in deionized water at a protein concentration of 4.23% w/v. The rOVD solution had a pH of 4.11. The deionized water had an absorbance of 0.037 (D600). The solution with 4.23% w/v rOVD had an absorbance of 0.047, an increase of 27%. The photo in FIG. 2 of the rOVD solution reveals a clear and colorless solution with no precipitate and no apparent viscosity changes in appearance and visual flow of liquid.

Example 4: Solubility and Clarity Testing at Varying Temperatures

The aqueous 30% rOVD (w/v) samples of Example 3, at pH 4.06 or pH 6.3 were incubated at room temperature and subjected to three heat treatments: pasteurization, hot fill, and retorting. The clarity and solubility of rOVD was then assessed visually (e.g., for turbidity, precipitate, viscosity, and color) and by measuring absorbance at 600 nm.

Heat treatments on each sample were executed as follows:

For pasteurization, the samples were heated to 72° C. for 1 minute and then placed in an ice bath for 10 minutes. Following the ice bath, the samples were placed at room temperature and then assessed for solubility and clarity.

For hot fill, the samples were heated to 85° C. for 30 seconds and then placed at room temperature for assessment of solubility and clarity.

For retorting, the samples were heated to 121° C. for 15 minutes at 19 psi and then kept at room temperature for assessment of solubility and clarity.

FIG. 3 shows the results for pH, absorbance and clarity of an rOVD solution comprising 30% rOVD in deionized water. The rOVD was surprisingly soluble in deionized water at 30% (w/v based on protein amount) at either pH 4.06 or pH 6.3. The photos of the rOVD solutions at both pH 4.06 and 6.3 look clear, pale green, and viscous, though less so under the "pre-processing" condition, which was prior to a heat treatment. It can be concluded from FIG. 3 that rOVD can remain soluble in both acidic (pH ~4.0) and slightly acidic (pH ~6) solutions at a concentration of rOVD of 30% w/v. More specifically, the 30% rOVD solution at pH 4.06 had an OD600 of 0.101 after pasteurization and an OD600 of 0.104 after hot filling. At the less acidic pH of 6.3, the OD600 of the 30% rOVD solution after pasteurization was 0.089 and after hot filling was 0.094. As such, there appeared to be greater clarity and solubility of the rOVD at higher pH values.

FIG. 4 shows the photos from the pH 4.06 experiments of FIG. 3. It can be concluded from FIG. 4 that rOVD can surprisingly remain in solution following heat application. 30% w/v.

Example 5: Solubility and Clarity Testing at Varying Temperatures and pH

Lyophilized rOVD (from Example 2) was blended into aqueous solution (distilled water) at concentration of 9% (w/v). Sodium citrate buffer (0.1M) was used to adjust the pH of the solutions to pH's of 2.5, 4 or 6, as shown in Table 3 below:

TABLE 3

Composition of the citrate buffer at pH 2.5, 4 or 6

| Citric acid (mL) | Sodium citrate (mL) | DI water (mL) | pH | rOVD |
|---|---|---|---|---|
| 49.2 | 0.8 | 50 | 2.5 | 9% w/v |
| 37 | 13 | 50 | 4 | 9% w/v |
| 6 | 44 | 50 | 6 | 9% w/v |

Following pH adjustment, separate aqueous rOVD samples at each pH were incubated at room temperature and subjected to three types of heat treatments: pasteurization, hot fill and retorting (as described below). The clarity and solubility of rOVD was then assessed visually (e.g., for turbidity, precipitate, viscosity, and color) and by measuring absorbance at 600 nm.

The heat treatments on each sample were executed as follows:

For pasteurization, the samples were heated to 72° C. for 1 minute and then placed in an ice bath for 10 minutes. Following the ice bath, the samples were placed at room temperature and then assessed for solubility and clarity.

For hot fill, the samples were heated to 85° C. for 30 seconds and then placed at room temperature for assessment of solubility and clarity.

For retorting, the samples were heated to 121° C. for 15 minutes at 19 psi and then kept at room temperature for assessment of solubility and clarity.

Figure 5B:
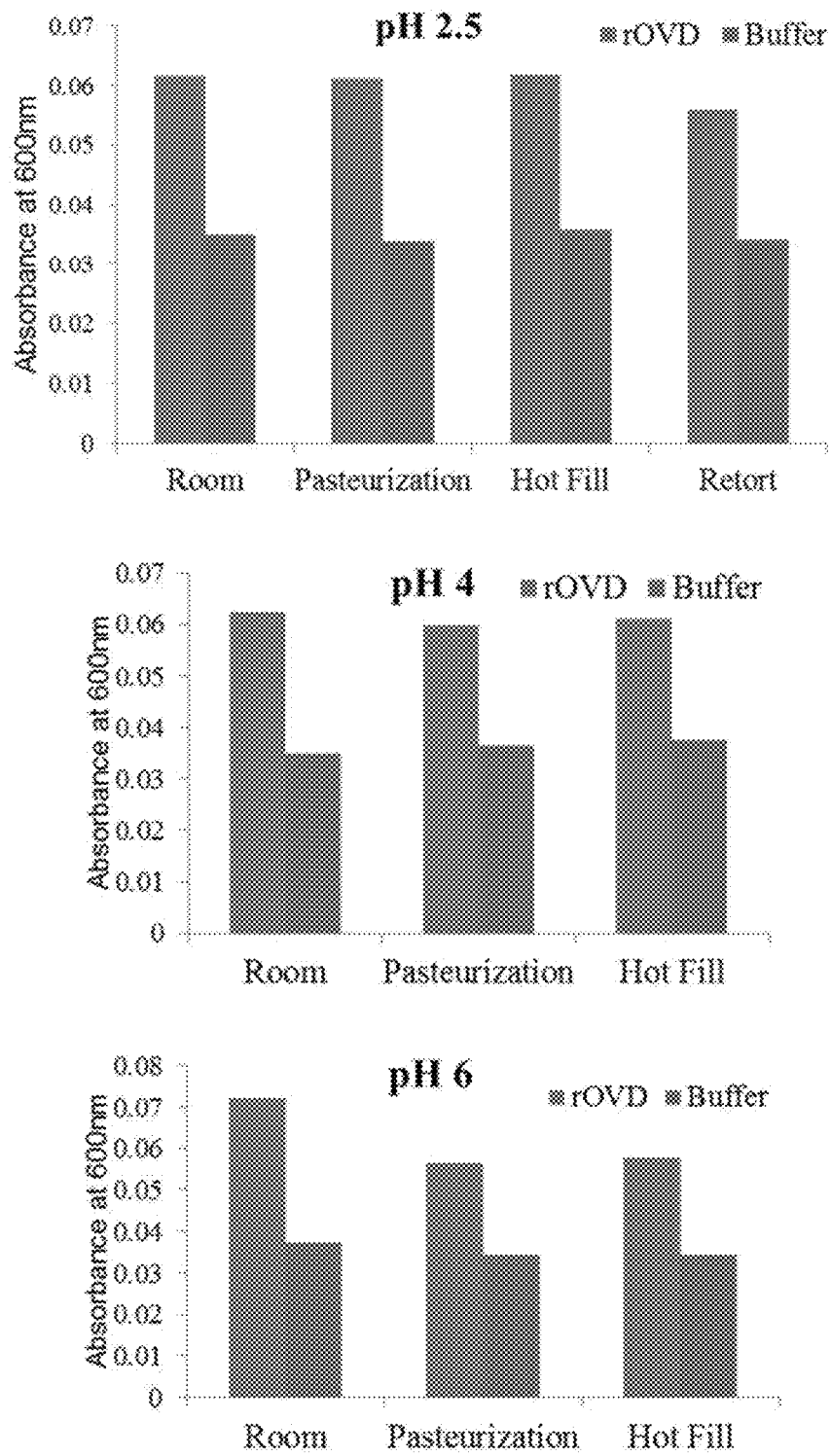
FIG. 5B are graphs showing absorbance of rOVD solution (9% w/v) at 600 nm after different heat treatment conditions at pH 2.5, 4 and 6. In each data pair, data in left columns relate to rOVD and data in right columns relates to Buffer.

The results of visual inspection and OD600 measurements of the samples are provided in FIG. 5A and FIG. 5B.

Pictures of the samples are shown in FIG. 5A. Effect of different heating treatments on absorbance (600 nm) of rOVD solution and buffer.

The addition of rOVD was found to increase the absorbance of the buffer solution. The absorbance of the rOVD solution remained the same following pasteurization and hot fill (no significant difference between pH 2.5 and pH 4). The absorbance was reduced following retorting. It was surprising that at different pH's, the rOVD solution remained clear even after the heating treatments of pasteurization and hot fill. An exception was that the rOVD solution coagulated at retorting conditions at pH 4 or pH 6. These results indicate that rOVD of the present disclosure remains soluble in solution at different acidic pHs, before and after application of heat.

Example 6: Solubility and Clarity of rOVD in Commercially-Available Beverages Based on carbonation levels published in literature (Table 4, below), San Pellegrino® was selected to represent a low carbonated beverage whereas Diet Coke™ was selected as a beverage with higher carbonation level. Gatorade™ and Red Bull™ represented the (non-carbonated) Energy Drink category. Pedialyte® was selected to study effect of electrolytes in a beverage on rOVD solubility.

TABLE 4

Carbonation levels for various commercially-available beverages

| Typical carbonation levels | Volume | g/L |
|---|---|---|
| Lightly Sparkling | 2 | 4 |
| Fruit juice carbonate | 2.5 | 5 |
| Lemonade | 3.0-3.5 | 6-7 |
| Cola | 4 | 8 |
| Mixer | 4.5-5.0 | 9-10 |

Lyophilized rOVD was blended into various drink solutions at a range of concentrations of 30-50% (% expressed as weight protein/volume). Surprisingly rOVD of the present disclosure was soluble at 30% w/v in Pedialyte®, San Pellegrino®, Diet Coke™, and Gatorade™. Red Bull™, was solubility at 26% w/v protein. At higher concentrations (e.g., >30%) rOVD exhibited solubility at some concentrations but was accompanied by a decrease in clarity and an increase in viscosity. At even higher concentrations (e.g., approaching 50% w/v), rOVD was no longer soluble and in some samples did not wet when placed into the drink solution. Results are shown in the tables below for concentrations 30% and higher (26% for Redbull™). A marked color change was seen with added rOVD for beverages that are colorless, whereas for colored beverages (e.g., Diet Coke™), little to no color change was observed with rOVD addition.

TABLE 5

Solubility study of rOVD in San Pellegrino ®

| Protein concentration (%) | Visual inspection | pH of San Pellegrino ® | pH of San Pellegrino ® with rOVD |
| --- | --- | --- | --- |
| 50 | Protein powder was not completely wetted. Did not form a solution | | |
| 40 | Protein powder was completely wetted. Formed a thick, pale green syrup-like mixture | | |
| 35 | Viscous suspension, pale brown syrup-like | | |
| 30 | Clear solution, pale green, viscous | 6.46 | 5.03 |

TABLE 6

Solubility study of rOVD in Diet Coke ®

| Protein concentration (%) | Visual inspection | pH of Diet Coke ® base | pH of Diet Coke ® with rOVD |
| --- | --- | --- | --- |
| 50 | Protein powder was not completely wetted. Did not form a solution | | |
| 40 | Protein powder was completely wetted. Formed a thick, pale brown syrup-like mixture | | |
| 35 | Viscous suspension, pale brown syrup-like | | |
| 30 | Clear solution, brown, viscous | 3.0 | 3.55 |

TABLE 7

Solubility study of rOVD in Gatorade ™ (Thirst Quencher lemon-lime)

| Protein concentration (%) | Visual inspection | pH of Gatorade ™ | pH of Gatorade ™ with rOVD |
| --- | --- | --- | --- |
| 50 | Protein powder was not wetted much. Did not form a solution. | | |
| 40 | Protein powder was not completely wetted. Formed a thick, pale yellow syrup-like mixture | | |
| 35 | Viscous suspension, pale yellow syrup-like | | |
| 30 | Clear solution, pale yellow/green, viscous | 2.78 | 3.7 |

TABLE 8

Solubility study of rOVD in Red Bull ™

| Protein concentration (%) | Visual inspection | pH of Red Bull ™ | pH of Red Bull ™ with rOVD |
| --- | --- | --- | --- |
| 50 | Protein powder was not wetted much. Did not form a solution. | | |
| 40 | Protein powder was not completely wetted. Formed a thick, off white syrup-like mixture. | | |
| 35 | Very viscous suspension, off white syrup-like. | | |
| 30 | Very viscous turbid pale green solution. | | |
| 26 | Clear solution, pale yellow/green, viscous. | 3.26 | 3.63 |

TABLE 9

Solubility study of rOVD in Pedialyte ®

| Protein concentration (%) | Visual inspection | pH of Pedialyte ® | pH of Pedialyte ® with rOVD |
| --- | --- | --- | --- |
| 50 | Protein powder was not completely wetted. Did not form a solution. | | |

TABLE 9-continued

Solubility study of rOVD in Pedialyte®

| Protein concentration (%) | Visual inspection | pH of Pedialyte® | pH of Pedialyte® with rOVD |
|---|---|---|---|
| 40 | Protein powder was completely wetted. Formed a thick, off white syrup-like mixture. | | |
| 35 | Viscous suspension, pale brown syrup-like. | | |
| 30 | Clear solution, pale green, viscous. | 5.51 | 5.75 |

Figure 6B:
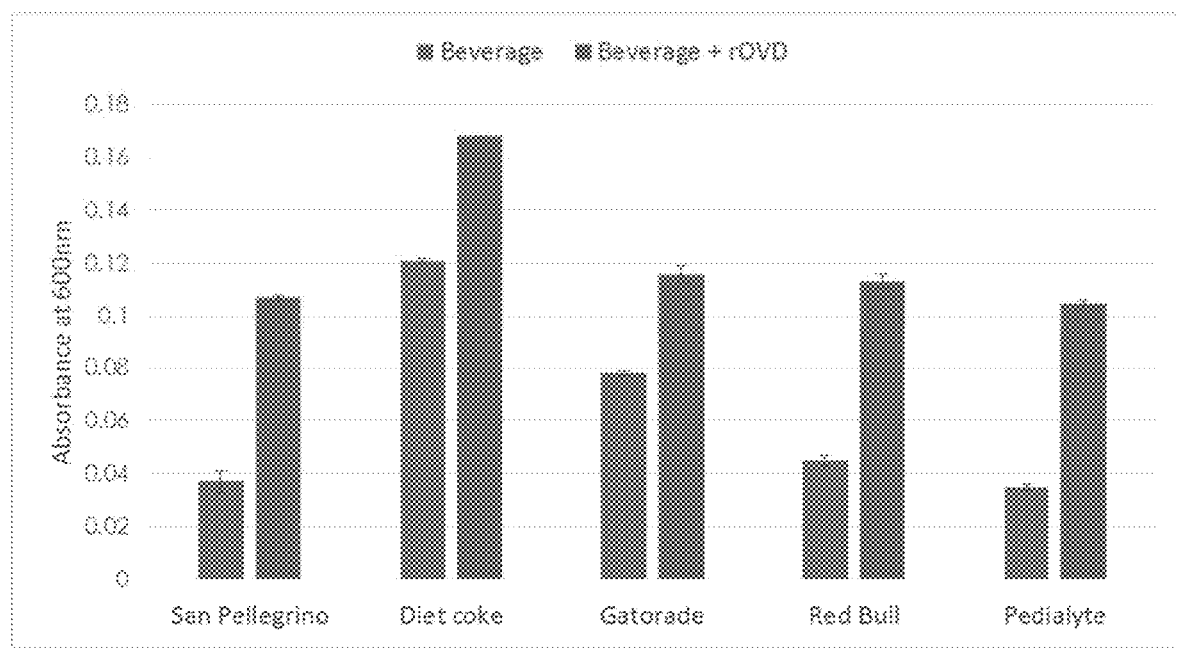
FIG. 6B is a graph showing absorbance of rOVD solution at 600 nm in different beverages. In each data pair, data in left columns relate to beverage and data in right columns relates to beverages with rOVD.

Pictures of the starting drinks (no rOVD) and the 30% rOVD solutions (26% for RedBull™) are shown in FIG. 6A. Absorbance results for rOVD solutions are shown in the graphs of FIG. 6B. The rOVD solutions at 30% w/v (26% w/v for RedBull™) were assessed using absorbance at 600 nm. Change in pH upon rOVD addition was dependent on the beverage composition and initial base pH.

Example 7: Production of Recombinant OVL Protein in *Pichia*

A recombinant lysozyme (rOVL) strain was made by transforming the *Pichia* species *Komagataella phaffii* with an expression cassette containing the OVL of SEQ ID NO: 45 expressed under the control of a methanol-inducible promoter. The OVL coding sequence encoded the mature OVL protein fused to the coding sequence for the alpha factor pre-pro secretion signal from *Saccharomyces cerevisiae*. The rOVL strain secreted rOVL when grown in media containing methanol. The broth containing the rOVL recombinant protein was centrifuged to remove cells and the resulting supernatant was processed similar to that of rOVD, as described above.

Example 8: OVD and OVL Combinations

In this example, solutions were made containing 2.5% (w/v) rOVL and nOVD at 9% (w/v). The resulting protein blend contained 21.7% rOVL and 78.3% and.
The rOVL+OVD blend was then heat treated under the following conditions:
Pasteurization: 72° C. for 1 minute, followed by 10 minutes in an ice bath.
Hot Fill: 85° C. for 30 seconds.
Retorting: 121° C. for 15 minutes at 19 psi.
A control OVD sample kept at room temperature was used to mimic aseptic processing conditions. Sodium citrate buffer (0.1M) was used to adjust the pH of the test solutions as described in Table 10.

TABLE 10

Composition of the citrate buffer at pH 2.5, 4 and 6

| Citric acid (mL) | Sodium citrate (mL) | DI water (mL) | pH |
|---|---|---|---|
| 49.2 | 0.8 | 50 | 2.5 |
| 37 | 13 | 50 | 4 |
| 6 | 44 | 50 | 6 |

As shown in FIG. 7 to FIG. 10 and Table 11, when the rOVL+OVD blend was heat treated by pasteurization, hot fill or retorting. The clarity/solubility of the rOVL+OVD blend, as measured by absorbance at 600 nm, remained unaffected at pH 2.5 compared to OVD control samples left at room temperature. At pH 4, the rOVL+OVD blend retained its clarity/solubility when pasteurized or hot filled. Retorting conditions produced turbidity, as measured by increased optical density (Table 11). Heat treatment at pH 6 resulted in loss of clarity for all samples.

TABLE 11

Absorbance of samples containing rOVL and native OVD at 600 nm

| | Control | Pasteurization | Hot Fill | Retorting |
|---|---|---|---|---|
| pH 2.5 | | | | |
| rOVL + OVD | 0.043 AB | 0.039 B | 0.038 B | 0.045 AB |
| OVD | 0.044 AB* | 0.042 AB | 0.050 A | 0.046 AB |
| rOVL | 0.038 B | 0.038 B | 0.037 B | 0.037 B |
| pH 4 | | | | |
| rOVL + OVD | 0.044 C | 0.065 C | 0.056 C | 0.154 A |
| OVD | 0.055 C | 0.166 A | 0.126 B | 0.315 D |
| rOVL | 0.049 C | 0.042 C | 0.042 C | 0.040 C |
| pH 6 | | | | |
| rOVL + OVD | 0.063 E | 0.610 B | 0.384 C | 0.898 B |
| OVD | 0.041 E | 0.202 D | 0.228 D | 0.525 B |
| rOVL | 0.039 E | 1.425 A | 0.588 B | white precipitate F |

*samples within each sub-table sharing the same letters are statistically similar (p > 0.05)

Figure 13:
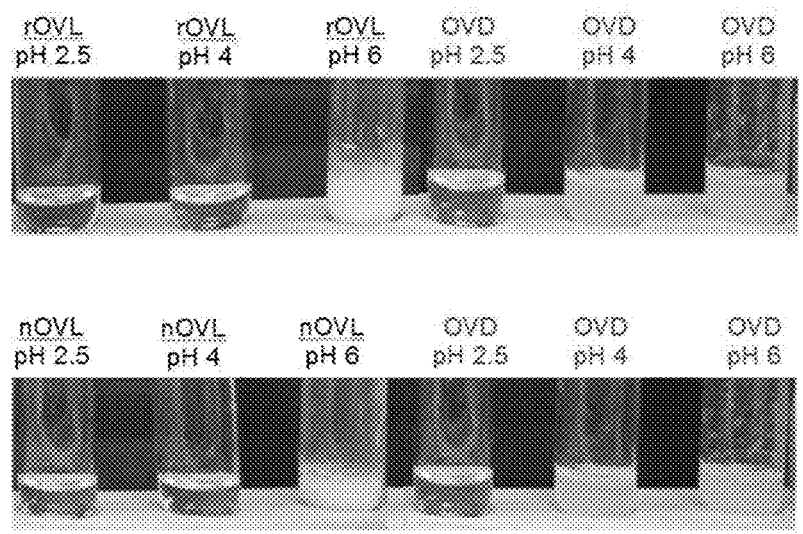
FIG. 13 illustrates, left to right, a comparison of Retorted (121° C.) samples of OVL control with OVD control at pH 2.5, 4, 6.

As shown in FIG. 11 to FIG. 13 and Table 12, native OVL (nOVL) samples had a similar effect on OVD as seen with the recombinant OVL (rOVL). At pH 2.5, the clarity/solubility of nOVL+OVD solutions were maintained when heat treated at all three conditions (pasteurization, hot fill or retorting). The nOVL+OVD solutions maintained their clarity at pH 4, with turbidity development only under retort conditions. pH 6 was not suitable for maintaining clarity after heat treatment.

TABLE 12

Absorbance of samples containing commercial native OVL (nOVL) and native OVD (nOVD) at 600 nm

| | Control | Pasteurization | Hot Fill | Retorting |
|---|---|---|---|---|
| pH 2.5 | | | | |
| nOVL + OVD | 0.043 AB | 0.046 AB | 0.043 AB | 0.051 B |
| OVD | 0.044 AB* | 0.042 AB | 0.050 B | 0.046 AB |
| nOVL | 0.037 A | 0.038 A | 0.038 A | 0.036 A |

TABLE 12-continued

Absorbance of samples containing commercial native OVL (nOVL) and native OVD (nOVD) at 600 nm

|  | Control | Pasteurization | Hot Fill | Retorting |
|---|---|---|---|---|
| pH 4 | | | | |
| nOVL + OVD | 0.052 CD | 0.073 C | 0.075 C | 0.174 A |
| OVD | 0.055 CD* | 0.166 A | 0.126 B | 0.315 E |
| nOVL | 0.037 D | 0.042 D | 0.042 D | 0.044 D |
| pH 6 | | | | |
| nOVL + OVD | 0.054 A | 0.445 F | 0.322 E | 0.954 H |
| OVD | 0.041 A* | 0.042 CD | 0.228 D | 0.525 G |
| nOVL | 0.041 A | 0.092 B | 0.178 C | Coagulated |

*samples within each sub-table sharing the same letters are statistically similar (p > 0.05)

The addition of rOVL to OVD in a sample at room temperature or heat processed increased the protein content of the sample without affecting the clarity or solubility of the sample. Thus, the addition of rOVL to OVD to a beverage increases the protein content of the beverage without affecting clarity or solubility, or sensory quality (appearance, smell, flavor and mouthfeel) either at room temperature or after heat processing.

Figure 14:
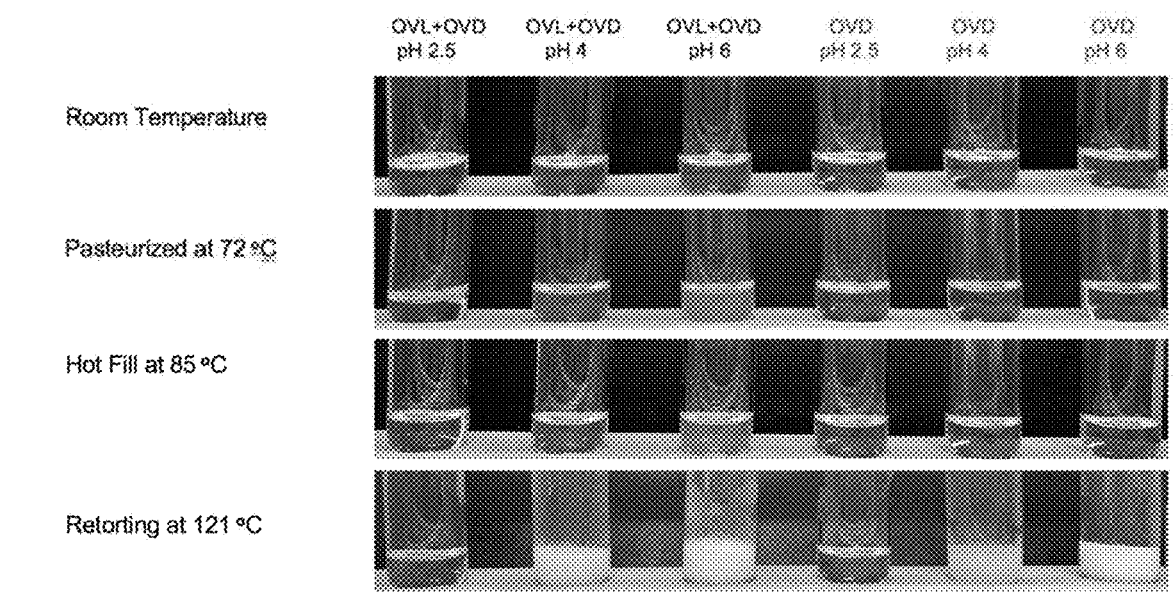
FIG. 14 illustrates, left to right, a comparison of rOVL+ rOVD and rOVD samples at room temperature and after different heat treatments at pH 2.5, 4, 6.

Samples were made containing recombinant OVD of the present disclosure (rOVD) at 9% (w/v), and 2.5% (w/v) rOVL. The resulting protein blend contained 78.3% rOVD and 21.7% rOVL. FIG. 14 compares solutions at room temperature and after different heat treatments at pH 2.5, 4, 6: rOVL+rOVD with rOVD control.

TABLE 13

Absorbance of samples containing rOVL and rOVD at 600 nm

|  | Room Temp | Pasteurization | Hot Fill | Retorting |
|---|---|---|---|---|
| pH 2.5 | | | | |
| rOVD + rOVL | 0.063 AB* | 0.066 A | 0.061 B | 0.061 B |
| rOVD | 0.062 B | 0.061 B | 0.062 B | 0.056 C |

TABLE 13-continued

Absorbance of samples containing rOVL and rOVD at 600 nm

|  | Room Temp | Pasteurization | Hot Fill | Retorting |
|---|---|---|---|---|
| pH 4 | | | | |
| rOVD + rOVL | 0.065 B* | 0.109 A | 0.066 B | White coagulate |
| rOVD | 0.062 B | 0.060 B | 0.061 B | White coagulate |
| pH 6 | | | | |
| rOVD + rOVL | 0.066 C* | 0.256 A | 0.091 B | White coagulate |
| rOVD | 0.072 C | 0.056 D | 0.058 D | White coagulate |

*samples within each sub-table sharing the same letters are statistically similar (p > 0.05)

Example 9: Comparison to Whey Protein Solutions

To compare results from rOVD to an alternate protein (whey), rOVD or whey proteins were solubilized in water at a concentration of 9% (w/v). Four commercially-available whey protein isolates (WP1, WP2, WP3 and WP4) were compared to rOVD of the present disclosure. The pH was measured by Hanna Lab pH probe for each sample and the absorbance was measured by SpectroMax at 600 nm wavelength. The results are provided in Table 14. The appearance was assessed by visual inspection; the odor was assessed by sniffing test; and the flavor was assessed by taste using a panel of 3 trained personnel.

TABLE 14

Solution characteristics of whey protein solutions (WPI) compared to rOVD solutions.

|  | WPI 1 | WPI 2 | WPI 3 | WPI 4 | rOVD |
|---|---|---|---|---|---|
| pH in 8.45% solution | 3.15 | 6.53 | 3.92 | 6.13 | 5.05 |
| Absorbance at 600 nm | 0.039 ± 0.001 | 0.423 ± 0.123 | 0.344 ± 0.038 | 0.792 ± 0.016 | 0.0002 ± 0.000 |
| Appearance | clear, yellow | cloudy, yellow | slightly cloudy, yellow | white, turbid | clear, colorless |
| Odor | lactic acid notes | negative dairy odor | cow/goat shed | milky odor | no odor |
| Flavor | salty, lactic acid notes | plastic taste, unpleasant odor & taste | slightly acidic, negative dairy flavor/odor | neutral taste, no acidity, milk like flavor | slight protein taste |

Figure 15A:
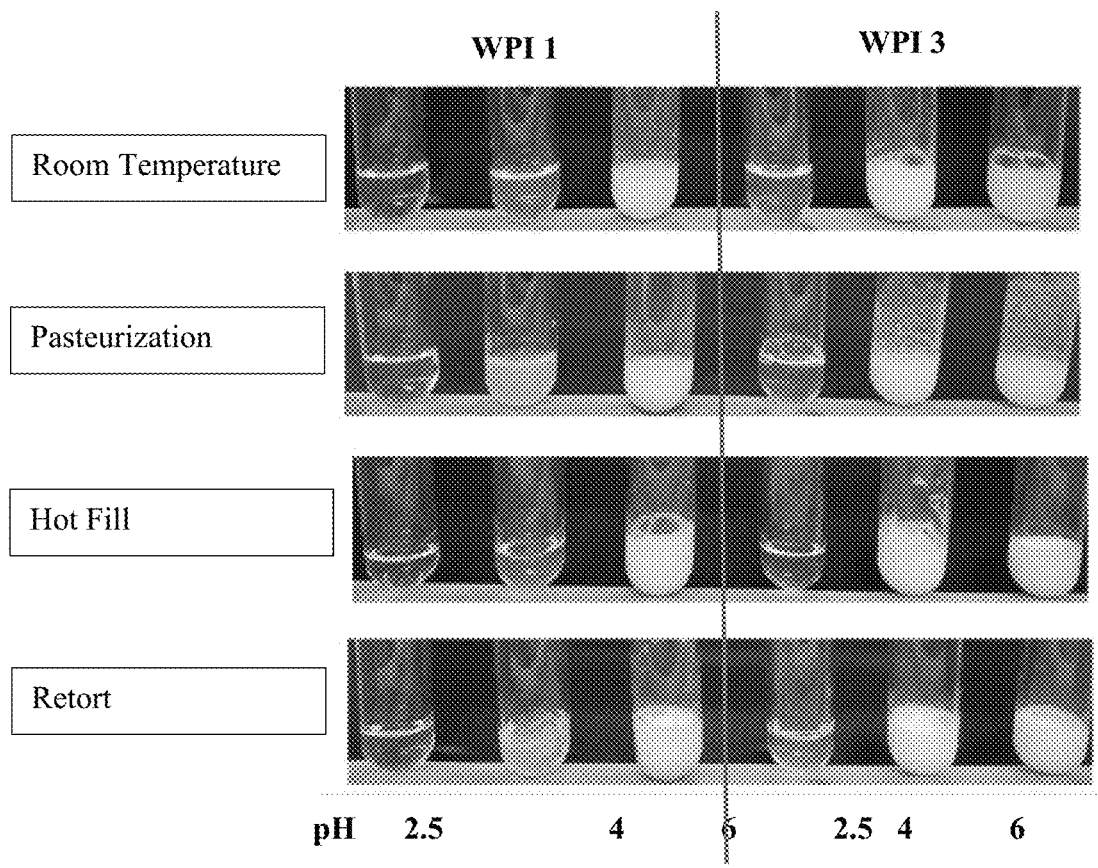
FIG. 15A and FIG. 15B illustrate comparisons of clarity for whey isolate (WPI1 and WPI3, 9% w/v) and rOVD solutions (9% w/v) at pH 2.5, 4 and 6.
Figure 15B:
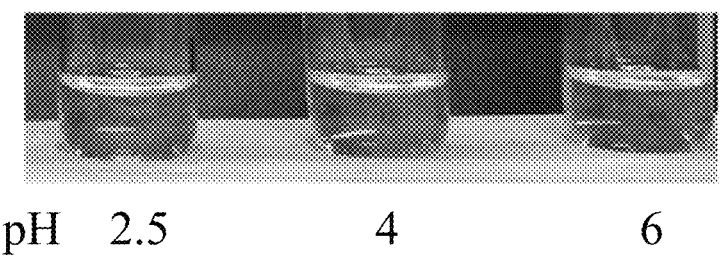

Whey protein isolates (WPI 1 and WPI 3) were at a concentration of 9 g per 100 ml distilled water, adjusted to pH 2, 4, or 6. Comparative results between whey protein solutions (WPI 1 and WPI 3) and rOVD solutions at pH 2, 4 and 6 are shown in FIG. 15A and FIG. 15B. The rOVD solutions show substantially higher solution clarity as compared to whey protein solutions at the same concentrations.

Example 10: Comparison of Clarity of Various Protein Water Solutions

In this example, the solubility of recombinant ovomucoid (rOVD) protein of the present disclosure was compared to the other proteins.

Appropriate amounts of acidic whey protein isolates (WP1 with 90% w/w protein and WP2 with 92.7% w/w protein), nOVD—85% protein content, rOVD—85.6% protein content, pea protein—90% protein content; and soy protein—90% protein content, were blended (using vortex) with water to form 5% protein solutions.

TABLE 15

List of Ingredients and their proportions.

| Ingredient | WP1 (neutral) (5%) % | WP2 (acidic) (5%) % | nOVD (5%) % | rOVD (5%) % | Pea protein (acidic) (5%) % | Soy protein (5%) % |
|---|---|---|---|---|---|---|
| Protein powder | 5.6 | 5.4 | 5.9 | 5.8 | 5.6 | 5.6 |
| DI water | 94.4 | 94.6 | 94.1 | 94.2 | 94.4 | 94.4 |
| Total | 100 | 100 | 100 | 100 | 100 | 100 |

Figure 16:
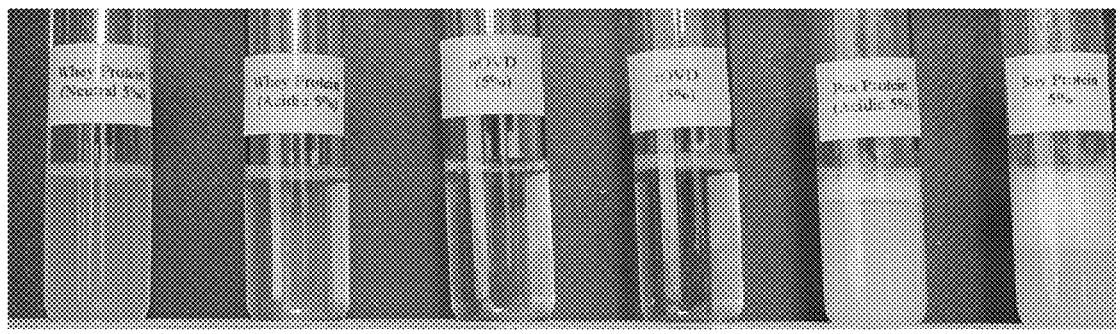
FIG. 16 illustrates protein water samples with 5% protein, from left to right, with whey protein isolate (neutral), whey protein isolate (acidic), nOVD, rOVD, 4%, pea protein (acidic), and soy protein.

FIG. 16 shows examples of the various protein solutions.

100 μl of each protein solution was aliquoted into a flat bottom, clear 96 well plate in three replicates (as shown in Table 15). The absorbance of each sample was measured at 600 nm with a plate adapter on Spectramax. Results are provided in Table 16.

TABLE 16

Absorbance results of various protein solutions.

| | Whey protein isolated (neutral) | Whey protein isolated (acidic) | nOVD | rOVD | pea protein (acidic) | soy protein | Water |
|---|---|---|---|---|---|---|---|
| OD600 | 0.1455 | 0.0527 | 0.0432 | 0.0456 | 0.9860 | 0.8821 | 0.0355 |

Example 11: Comparison of Suspension Stability of Protein Fortified Solutions In this example, the feasibility of fortifying orange juice (with added calcium and vitamin D) with rOVD was determined.

Orange juice (without pulp; with 350 mg Calcium, and 2.5 mcg vitamin D per serving size of 8 fluid oz) was protein fortified using nOVD, whey protein, or rOVD (86% protein content). The samples were treated as follows. The protein of interest was added at various amounts to 10 g orange juice and mixed until completely dissolved to produce a fortified orange juice. The pH of the original orange juice with no protein fortification (as a control sample) was measured and considered as a target pH. The pH of fortified orange juice samples was adjusted using 1M citric acid and/or baking soda to become close to the target pH. The protein solubility and/or precipitation was visually observed in all samples before a heat treatment. A heat treatment of 70° C. for 1 min was applied to sufficiently reduce the microbial load in orange juice. Then, the samples were immediately cooled to 4° C. for 10 minutes.

Figure 17A:
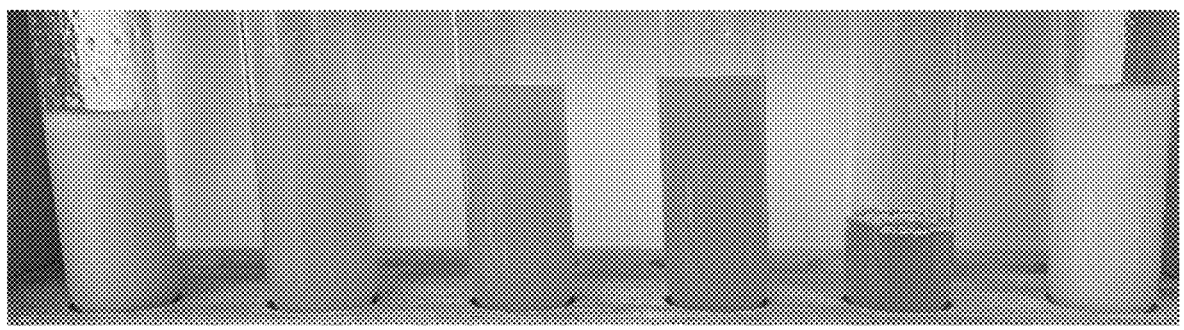
FIG. 17A and FIG. 17B illustrate samples of orange juice, from left to right, with 15% whey protein, 15% nOVD, 15% rOVD, 20% rOVD, 30% rOVD, or (no protein) control respectively.
Figure 17B:
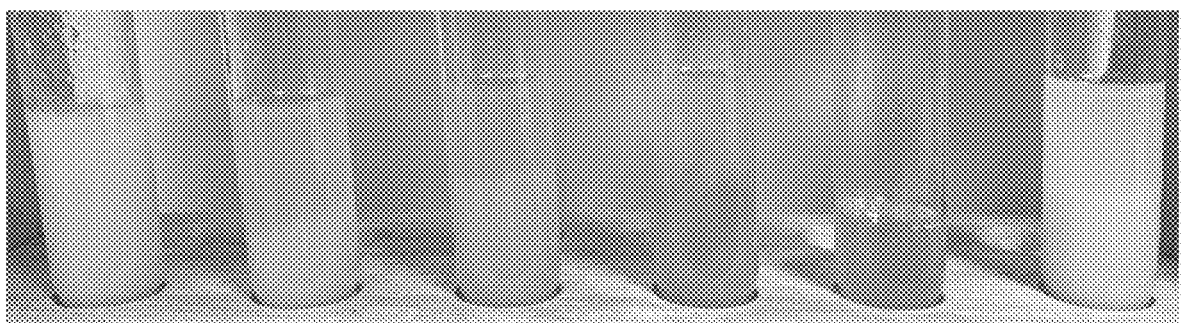

The physical and suspension stability of the samples were evaluated immediately after heating process (FIG. 17A) and after 48 hours storage at 4° C. (FIG. 17B).

The suspension stability of orange juice fortified with 15% of nOVD or 15% of rOVD were found to be similar to the control, which included no protein fortification. After 48 hours, orange juice fortified with 15% of whey protein had slightly formed a gel, thus a separation was not observed in this sample. rOVD at a high concentration (30%) did not precipitate and was completely soluble in the orange juice, even in the presence of 0.25 mcg vitamin D and 35 mg calcium.

rOVD was also found to be heat stable and did not form a gel during pasteurization. In terms of appearance, no significant difference was observed between the control and the orange juice fortified with 15% of nOVD or with rOVD at two levels: 15% or 20%.

Example 12: Comparison of Suspension Stability of Protein-Fortified Jelly

In this example, the feasibility of fortifying jelly with rOVD was evaluated.

Jello™ jelly was used for protein fortification using nOVD (80% protein), rOVD (86-93% protein), unflavored whey isolate proteins (87.5-92.7% protein), unflavored gelatin (92% protein). The samples were prepared as follows:

Control jelly method: hot water was added to the jelly mix power and stirred for two minutes until completely dissolved. Cold water was then added to fill 2 cm of 1 oz cups, capped and then refrigerated.

Fortified jelly method: Hot water was added to the jelly mix power and stirred for two minutes until completely dissolved. Cold water was gradually added to the protein powder and slowly stirred to dissolve. The dissolved jelly solution was transferred in the protein mixture and mixed completely. 2 cm of 1 oz cups were filled, capped and then refrigerated.

Protein jelly formulations: List of ingredients and their proportions used in the control and other experimental jelly samples, with specific protein of interest, are presented below in Table 17.

TABLE 17

| | List of Ingredients | | | |
|---|---|---|---|---|
| Ingredient | Control % | Whey 20% % | nOVD 20% % | rOVD 20% % |
| Jello | 15.23 | 11.7 | 11.4 | 11.7 |
| Cold water | 42.38 | 32.7 | 31.8 | 32.5 |
| Hot water | 42.38 | 32.7 | 31.8 | 32.5 |
| Protein | 0 | 22.9 | 25.0 | 23.3 |
| Total g | 100 | 100 | 100 | 100 |

(* amounts of ingredient adjusted based on % protein w/w content) The textures of the jelly samples were measured using Brookfield Conn.3 Texture Analyzer (Table 18). From each jelly sample three readings were taken. Jellies were centrally located under the test probe and compressed to a distance of 5 mm following the test settings below. Adhesiveness (also known as stickiness) measured the energy required to separate the attractive forces between the surface of the jelly and the surface of the probe (which approximates the stickiness on a tongue, teeth, and/or palate). Hardness is the force required to compress the jelly to attain a given deformation.

TABLE 18

Texture Analyzer Test Settings

| Test | Compression test |
|---|---|
| probe | TA 5 |
| Textural properties | Hardness (g) and adhesiveness (mj) |
| Speed | 1 mm/sec |
| Distance | 5 mm |
| Sample size | cylinder shape; H: 20 mm D: 36 mm |
| Trigger load | 4.5 g |

In terms of adhesiveness, no statistically-significant difference between jelly fortified with 20% nOVD and the control was observed. On the other hand, the adhesiveness values for jelly with 20% of whey and rOVD proteins were significantly lower (Table 19).

TABLE 19

Texture Analysis Results.

| Treatments | Jelly control | 20% whey protein | 20% nOVD | 20% rOVD |
|---|---|---|---|---|
| Hardness (g) | *53.2 ± 1.7a | 32.8 ± 3.4 b | 31.1 ± 4.3 b | 32.8 ± 3.4 b |
| Adhesiveness (mj) | 0.09 ± 0.03 a | 0.03 ± 0.005 c | 0.08 ± 0.01 ab | 0.04 ± 0.02 bc |
| Jelly pH | 4.3 | 5.5 | 5 | 5.5 |

*Mean ± Std Dev; Jelly samples containing different letters for a given quantitative parameter (for example Hardness) are statistically different to each other at $p < 0.05$.

Jelly fortified with 20% of whey, nOVD, or rOVD were significantly less hard than the control jelly.

Figure 18A:
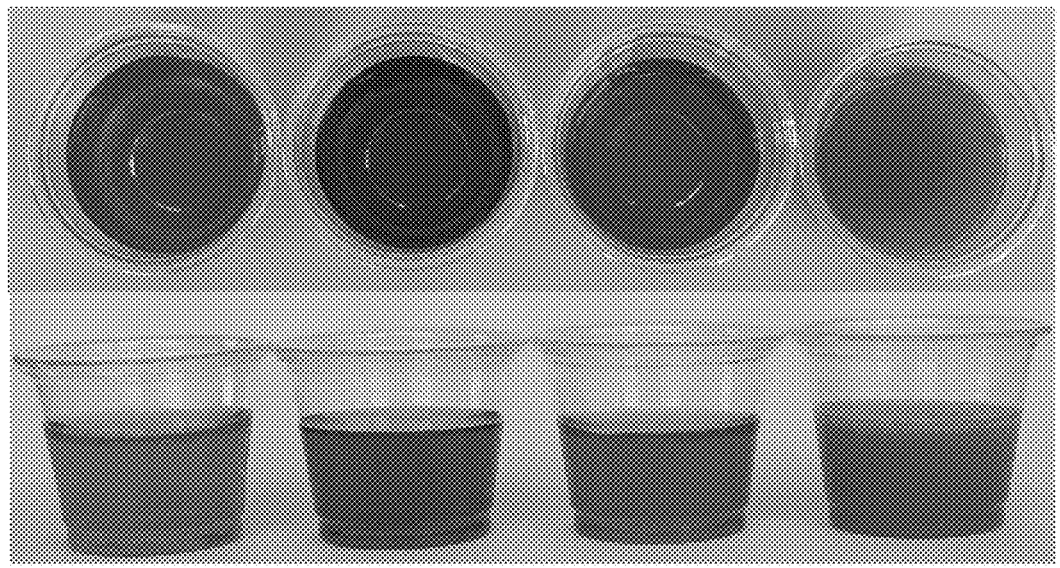
FIG. 18A illustrates jelly samples, from left to right, control (without protein supplementation), supplemented with 20% rOVD, supplemented with 20% nOVD and supplemented with 20% whey protein.
Figure 18B:
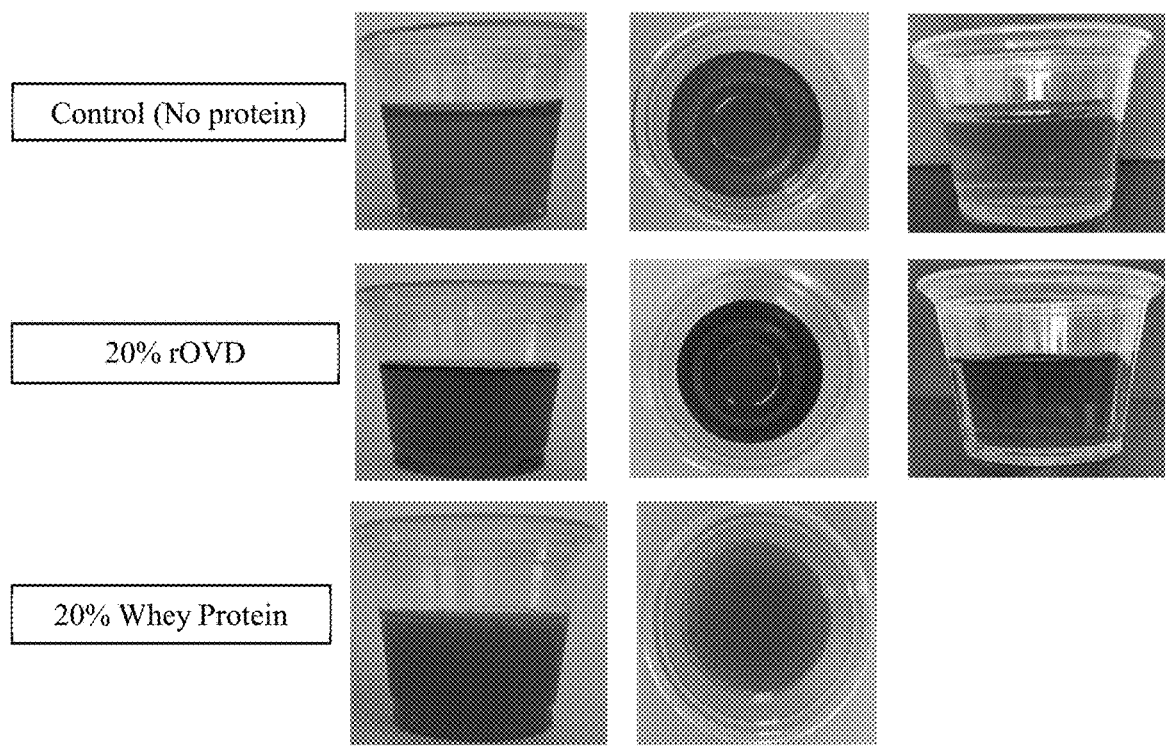
FIG. 18B illustrates comparison of jelly samples with no protein (control), supplemented with 20% rOVD and supplemented with 20% whey protein.

No significant difference was observed between the clarity of the control jelly and jelly fortified with 20% of rOVD ($p<0.05$). Jelly fortified with whey isolate protein was opaque and unclear. (FIG. 18A and FIG. 18B).

Figure 18C:
FIG. 18C to FIG. 18E illustrate jelly samples supplemented with 20% whey protein, supplemented with 16% gelatin and supplemented with 20% gelatin.

The texture of Jello™ fortified with 20% of whey protein was very soft and not comparable to the control. (FIG. 18C).

Figure 18D:
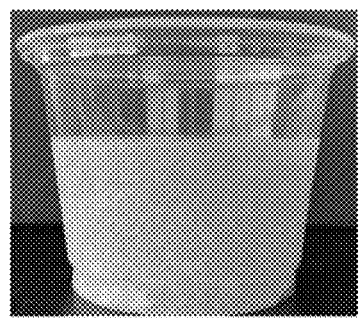
Figure 18E:
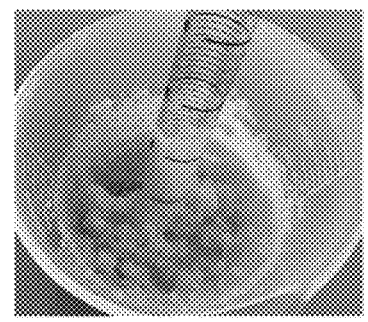

The texture of Jello™ with either 16% or 20% of hydrolyzed gelatin was rubbery, with strong bounce and resistance to deformation. In this experiment aliquoting of the samples was not possible, since the jelly set very quickly at room temperature. (FIG. 18D and FIG. 18E).

Example 13: Testing Recombinant OVD from Various Species

In this example, properties of rOVD having amino acid sequences of non-chicken, avian species was evaluated.

Two expression constructs were created for expression for two non-chicken rOVD (SEQ ID NO: 40 called rOVD-T (Turkey vulture) and SEQ ID NO:43 called rOVD-H (humming bird) hereafter) in *Pichia pastoris* and expressed, purified and processed similar to Example 2. Lyophilized rOVD samples were blended into aqueous solution (distilled water) at different concentrations and pHs. Clarity and solubility of the rOVD solutions was then assessed visually (e.g., for turbidity, precipitate, viscosity, and color) as well as by measuring absorbance at 600 nm.

Figure 19A:
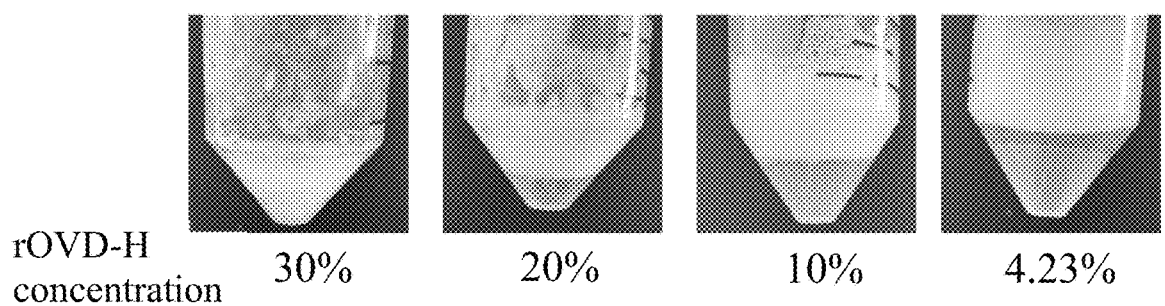
FIG. 19A and FIG. 19B illustrate rOVD-H and rOVD-T samples solubilized in water at various concentrations.

FIG. 19A shows protein-water samples comprising rOVD-H in deionized water at protein concentrations of 4.23%, 10%, 20% or 30% w/v. The solutions had a pH of 4.15. Like the chicken rOVD of the previous examples, FIG. 19A reveals a clear and colorless solution with no precipitate and no apparent viscosity changes in appearance and visual flow of liquid for solutions comprising up to 20% rOVD-H.

Figure 19B:
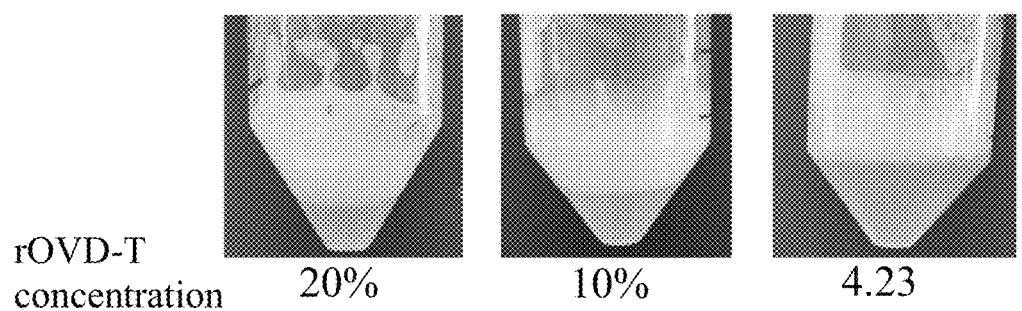
Figure 20:
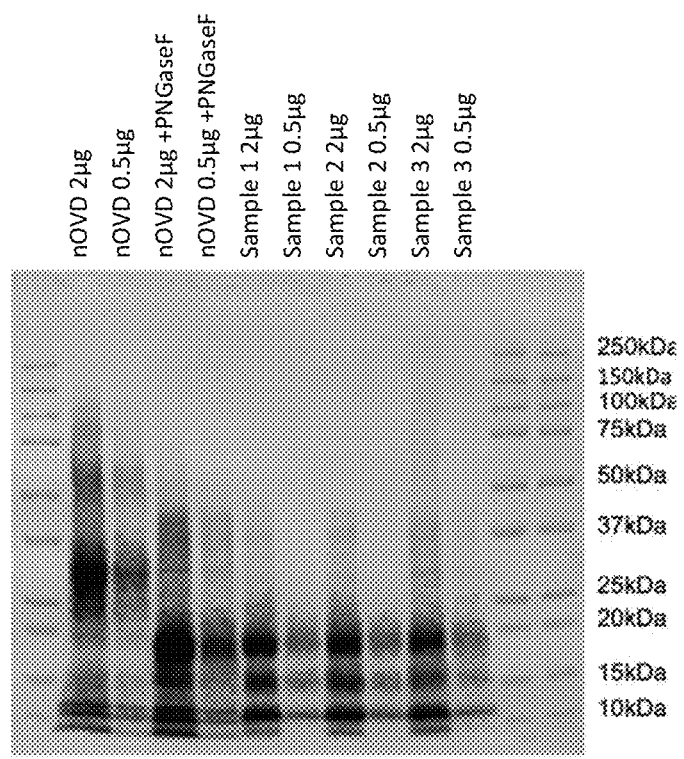
FIG. 20 illustrates the comparison in immunoreactivity for rOVD samples, native ovomucoid from chicken egg white (nOVD) and deglycosylated native ovomucoid (nOVD+PNGaseF).

FIG. 19B shows protein-water samples comprising rOVD-T in deionized water at protein concentrations of 4.23%, 10% or 20% w/v. The solutions had a pH of 3.69. Like the chicken rOVD of the previous examples, FIG. 19B reveals a clear solution with no precipitate and no apparent viscosity changes in appearance and visual flow of liquid for solutions comprising up to 10% rOVD-T. At 20% the protein did not fully dissolve.

The samples were incubated at room temperature and subjected to three types of heat treatments: pasteurization, hot fill, or retorting as in Example 4 or Example 5. The clarity and solubility of the various rOVD were then assessed visually (e.g., for turbidity, precipitate, viscosity, and color) as well as by measuring absorbance at 600 nm. Table 20 shows the results for pH, absorbance, and clarity of rOVD solution comprising 4.23% rOVD-H or rOVD-T solutions in buffer or water. Data in the "pre-processing" column was measured before any heat treatment. It was surprising that at different pH's the rOVD solutions remained clear even after extreme heating like pasteurization, hot fill, or retort. These results indicate that rOVD samples remain soluble in solution at different acidic pHs, before and after application of heat.

These data show that the favorable properties disclosed above for the recombinant chicken OVD (see Example 2) are also obtainable with other recombinant OVDs.

TABLE 20

Solubility and clarity study of rOVD-H and rOVD-T

| Sample | pH | OD Pre-processing at RT | OD post pasteurization | OD post hot fill | OD post autoclave/retort |
|---|---|---|---|---|---|
| rOVD-H + buffer | 2.5 | 0.0569 | 0.0547 | 0.0548 | 0.0537 |
| rOVD-T + buffer | | 0.058 | 0.059 | 0.057 | 0.056 |
| rOVD-H + buffer | 4 | 0.0546 | 0.0544 | 0.0552 | 0.0641 |
| rOVD-T + buffer | | 0.055 | 0.055 | 0.057 | 0.055 |
| rOVD-H + buffer | 6 | 0.053 | 0.053 | 0.055 | 0.061 |
| rOVD-T + buffer | | 0.054 | 0.054 | 0.054 | 0.068 |
| rOVD-H + water | 3.5-3.9 | 0.067 | 0.084 | 0.090 | 0.236 |
| rOVD-T + water | | 0.097 | 0.106 | 0.116 | 0.219 |

Example 14: Comparison of Bovine Trypsin Inhibitory Activity rOVD as produced in Example 2 was utilized in this Example. The trypsin inhibition activity was compared between native OVD (nOVD) and recombinant OVD (rOVD) in a standard assay (AACC #22-40.01) using bovine trypsin. A comparison of rOVD with nOVD is shown in Table 21. One trypsin unit is arbitrarily defined as an increase of 0.01 absorbance unit at 410 nm per 10 ml of reaction mixture under the conditions of the assay. Trypsin inhibitor activity is expressed in terms of trypsin inhibitor units (TIU). Three different batches of rOVD (samples 1-3) were compared to a native chicken ovomucoid.

TABLE 21

Comparison of trypsin inhibition activity

| Product | Trypsin inhibition activity |
|---|---|
| Sample 1 | 8190 TIU/g |
| Sample 2 | 8180 TIU/g |
| Sample 3 | 8649 TIU/g |
| Native chicken Ovomucoid | 13721 TIU/g |

Example 15: Comparison of In Vitro Digestibility

The in vitro digestibility of rOVD samples was measured using the Protein Digestibility Assay procedure (Megazyme, Medallion Labs). A comparison of rOVD samples with nOVD is shown in Table 22. The data demonstrates equivalent in vitro digestibility between native ovomucoid and rOVD.

TABLE 22

Comparison in vitro digestibility

| Product | In-vitro digestibility |
|---|---|
| Sample 1 | 93% |
| Sample 2 | 93% |
| Sample 3 | 93% |
| Native chicken Ovomucoid | 92% |

Example 16: Ovomucoid Specifications

Based upon the characterization of the produced rOVD compositions and the properties of native chicken ovomucoid, product specifications (Table 23) and quality control specifications (Table 24) were constructed for an rOVD of the present disclosure Protein percentages were measured using AOAC 2006. See, Protein (crude) in animal feed, combustion method, 990.03. In: Official methods of analysis of AOAC International. 18th ed. Gaithersburg: ASA-SSA Inc. and AOAC 2006. Proximate Analysis and Calculations Crude Protein Meat and Meat Products Including Pet Foods—item 80. In: Official methods of analysis Association of Analytical Communities, Gaithersburg, Md., 17th edition, Reference data: Method 992.15 (39.1.16); NFNAP; NITR; NT.

Moisture percentages were measured using Association of Official Analytical Chemists. 1995. In Official Methods of Analysis.

Carbohydrate percentages were measured using methods described in J AOAC Int. 2012 September-October; 95(5): 1392-7.

Fat by acid hydrolysis were measured using AOAC International. 2012. Official Method Fat (crude) or ether extraction in pet food. Gravimetric method, 954.02. In: Official Methods of Analysis of AOAC International, 19th ed., AOAC International, Gaithersburg, Md., USA, 2012.

Standard plate count was measured using AOAC International. 2005. Aerobic plate count in foods, dry rehydratable film, method 990.12. AOAC International, 17th ed. Gaithersburg, Md. Yeast and mold counts were measured using AOAC Official Method 997.02. Yeast and Mold Counts in Foods Dry Rehydratable Film Method (Petrifilm™ Method) First Action 1997 Final Action 2000 *Salmonella* was measured using AOAC International. 2005. *Salmonella* in selected foods, BAX automated system, method 2003.09. In Official methods of analysis of AOAC International, 17th ed., AOAC International, Gaithersburg, Md. Total coliform was measured using AOAC International. 2005. *E. coli* count in foods, dry rehydratable film, method 991.14. In: Official methods of analysis of AOAC International, 17th ed. AOAC International, Gaithersburg, Md.

TABLE 23

Specification for Ovomucoid produced by *P. pastoris* DFB-003

| Physical properties | Specification | |
|---|---|---|
| Source | Yeast fermentation-derived | |
| Appearance | White to off-white amorphous powder | |
| Solubility | Soluble in water | |

| | Specification | Method |
|---|---|---|
| Chemical Properties (in powder as is) | | |
| Protein | >75% | AOAC 990.03[1a] |
| | | AOAC 992.15[1b] |
| Moisture | Maximum 10.0% | AOAC 925.09[2] |
| Carbohydrate | Maximum 20% | Calculated |
| Ash | Maximum 2.0% | AOAC 942.05[3] |
| Fat by Acid Hydrolysis | <0.1% | AOAC 954.02[4] |
| Hg | <1 ppm | ICP-AES[5] |
| Pb | <1 ppm | ICP-AES[5] |
| As | <1 ppm | ICP-AES[5] |
| Cd | <1 ppm | ICP-AES[5] |
| Microbial Properties (in powder as is) | | |
| Standard Plate Count | <10000 CFU/g | AOAC 990.12[6] |
| Yeast & Mold | <100 CFU/g | AOAC 997.02[7] |
| *Salmonella* | Not Detected/25 g | AOAC 2003.09[8] |
| *E. coli* | Not Detected/25 g | AOAC 991.14[9] |
| Total coliform | ≤30 CFU/g | AOAC 991.14[9] |

TABLE 24

Quality control results for three lots of Ovomucoid produced by *P. pastoris* DFB-003

| Analysis Parameter | Specification | SOL19303 | SOL19317 | SOL19351 |
| --- | --- | --- | --- | --- |
| Protein | >75% | 75.31 | 75.06 | 79.94 |
| Protein (% dry weight powder) | >80% | 82.2 | 82.5 | 87.8 |
| Moisture and Volatiles | <10% | 8.4 | 9 | 9 |
| Carbohydrates, Calculated | <20% | 15.53 | 15.28 | 11.06 |
| Ash | <2% | 0.76 | 0.66 | <0.4 |
| Fat by Acid Hydrolysis | <0.1% | <0.10 | <0.10 | <0.10 |
| Arsenic (As) | <1 mg/kg | <0.010 | <0.010 | <0.010 |
| Mercury (Hg) | <1 mg/kg | <0.010 | <0.010 | <0.010 |
| Lead (Pb) | <1 mg/kg | 0.03 | 0.063 | 0.168 |
| Cadmium (Cd) | <1 mg/kg | <0.010 | <0.010 | <0.010 |
| Aerobic Plate Count | <10000 CFU/g | <10 | <10 | <10 |
| Molds | <100 CFU/g | <10 | <10 | <10 |
| Yeast | <100 CFU/g | <10 | <10 | <10 |
| Salmonella | Not Detected/25 g | Not Detected | Not Detected | Not Detected |
| Escherichia Coli | Not Detected/25 g | Not Detected | Not Detected | Not Detected |
| Coliforms | <10 CFU/g | <10 | <10 | <10 |
| Absence of source organism from product | Not detected */mg sample | Not detected | Not detected | Not detected |
| Absence of encoding DNA from product | Not detected **/mg sample | Not detected | Not detected | Not detected |

\* Limit of detection for source organism = 11 CFU/mg sample
\*\* Limit of detection for encoding DNA = 10 femtogram

Example 17: Absence of Production Organism and DNA in rOVD Preparations rOVD powder was plated on PGA plates and if samples yielded colonies, these were re-streaked and analyzed by PCR for the presence of the *Pichia* organism. This procedure was applied to three lots of rOVD powder produced from the recombinant strain. No manufacturing organism was detected in any of the lots (Table 24).

PCR analysis was used to confirm that no encoding pieces of recombinant DNA was present in the rOVD preparation using primers for the rOVD cassette. OVD plasmid DNA was used as a positive control, producing a 570 bp band corresponding the OVD PCR product. This band was absent in all three rOVD powder lots tested.

Example 18: Comparison Immunoreactivity

Western Blot comparisons were performed on three rOVD lots using primary anti-ovomucoid antibody from rabbit (NBP1-74676 Novus) at a 1:2500 dilution. The secondary antibody used was goat anti-rabbit IgG conjugated to alkaline phosphatase (AP ab97048 Abcam). Molecular weight marker preparation used was from Bio Rad (161-0394). The comparison showed the same immunoreactivity for rOVD samples, native ovomucoid from chicken egg white (nOVD) and deglycosylated native ovomucoid (nOVD+PNGaseF) (FIG. 20).

Example 19: Fermentation and Purification of rOVD

An rOVD *P. pastoris* seed strain was removed from cryo-storage and thawed to room temperature. Contents of the thawed seed vials were used to inoculate liquid culture media in the primary fermenter and grown at process temperature until target cell density was reached. Then, the grown rOVD *P. pastoris* was transferred to a production-scale reactor. The culture was grown in the production bioreactor at target fermentation conditions and fed a series of substrates. The fermentation was analyzed for culture purity at multiple times during the process.

The recombinant OVD was purified by separating the cells from the liquid medium by centrifugation, followed by microfiltration. Fermentation broth was first brought to pH 3 and diluted with DI water. Cells were removed using bucket centrifugation. The collected supernatant was brought to pH 7 using sodium hydroxide and a 0.2 μm filtration was performed followed by diafiltration with five volumes of deionized water. The permeates of the 0.2 μm were adjusted to pH 5 and then concentrated via 5 kDa TFF membrane. The 5 kDa retentate was precipitated using 65% saturation ammonium sulfate. After salt addition, the pH was adjusted to pH 4-4.1 with phosphoric acid. The mixture was incubated with agitation at room temperature overnight. The next day, precipitates were spun down using bucket centrifugation. The rOVD precipitates were dissolved in DI water and pH adjusted to 5 using sodium hydroxide. The rOVD solution was then diafiltered and then the retentate was passed through 0.2 μm bottle filters.

A spray dryer was used to dehydrate the rOVD solution into rOVD powder.

Example 20: Hydrogen Peroxide Treatment During rOVD Purification

Liquid rOVD was concentrated to 50-60 g/L using a 5 kDa TFF membrane. The rOVD solution was passed through a 0.2 μm filter to remove microbes. Hydrogen peroxide, an oxygen-generating agent, in an amount to equal 10% volume of the solution was slowly added to the rOVD solution while stirring. The mixture was incubated with agitation and monitored to ensure color change from a dark green-brown color before treatment to a pale-yellow color after treatment. After 1.5 hours, diafiltration was performed via 5 kDa TFF membrane with 5 volumes of DI water. The rOVD in the 5 kDa diafiltration retentate was precipitated using ammonium sulfate at 65% salt saturation at room temperature. After addition of salt, the pH was adjusted to pH4-4.1 with phosphoric acid. The mixture was incubated with agitation overnight to form precipitates. The next day, the precipitates were spun down using bucket centrifugation. The precipitates were removed, dissolved in deionized water and pH adjusted to 5 using sodium hydroxide. Five kDa TFF membranes were cleaned and diafiltration was performed using volumes of DI water until a retentate conductivity of less than 2.0 mS was achieved. The retentate was passed through 0.2 μm bottle filters. The filtered rOVD solution was then spray dried and stored.

Example 21: Reprocessed rOVD Treated with Hydrogen Peroxide

OVD powder was dissolved in deionized water to 50-60 g/L and filtered through a hollow fiber 0.2 μm tangential flow filter, then through a 0.2 μm bottle filter. Hydrogen peroxide in an amount to provide a 10% solution was slowly stirred into the rOVD solution and incubated for thirty minutes. The treated solution was washed through a 5 kDa membrane using 5 volumes of DI water.

Ammonium sulfate was slowly added to the retentate solution and the pH changed to between 4 to 4.1 using phosphoric acid. After overnight incubation with medium agitation, the solution was centrifuged, and supernatants discarded. Precipitates were collected, dissolved in DI water, and brought to pH 5 using sodium hydroxide. The protein solution was desalted with a 5 kDa membrane and filtered through a 0.2 μm bottle filter. Then, the protein solution was spray dried to produce rOVD powder.

Example 22: Sensory Testing and Results

The rOVD sample and the $H_2O_2$ reprocessed sample called RE-RC were analyzed for their sensory characteristics to determine the effects of hydrogen peroxide treatment.

A solution of each dry sample was prepared with Deionized water at 4.23% w/v concentration. Both samples were presented to the panelists in the same session, monadically. Trained panelists (n=6) evaluated both the samples in terms of their appearance, smell, taste, mouthfeel and aftertaste. For each category, the panelists described the perceived attributes and then rated each attribute's intensity (Kemp et al. 2009) using the intensity rating scale (Table 25).

Table 26 shows that the hydrogen peroxide-treated sample was lighter in color, and had a cleaner sensory profile, with fewer sensory attributes compared to the control sample.

TABLE 25

Attribute Intensity Rating Scale

| APPEARANCE (Clarity) | APPEARANCE (Color Intensity) | SMELL, FLAVOR, AFTERTASTE & MOUTHFEEL (Intensity rating for "Individual attributes in each category) |
|---|---|---|
| 0 = clear | 0 = no color | 0 = not detected |
| 1 = very slightly turbid | 1 = very pale | 1 = very mild |
| 2 = slightly turbid | 2 = pale | 2 = mild |
| 3 = mild/moderate turbidity | 3 = moderate intensity | 3 = moderate |
| 4 = moderately turbid | 4 = dark | 4 = strong |
| 5 = very turbid | 5 = very dark | 5 = very strong |

TABLE 26

Sensory evaluation results

| Powder Batch Name | rOVD | $H_2O_2$ Reprocessed RE-RC |
|---|---|---|
| Appearance | pale yellow/green (2), clear (0), bubbly, not easy to mix (sediments visible) | very pale yellow (1), clear (0), very frothy |
| Smell | mild yeasty (2), mild/moderate musty (2.5), mild nutty (2) | very mild musty (1) |
| Taste | mild buttermilk (2), mild/moderate toasted nutty (2.5), mild yeasty (2) | very mild yeasty (1) |
| Mouthfeel | None (0) | None (0) |
| Aftertaste | None (0) | None (0) |

Example 23: H₂O₂ Treated rOVD Tested for Solubility and Clarity

Solubility and clarity of the control and hydrogen peroxide treated sample solutions (at 4.23% w/v) were measured in terms of optical density ($A_{600}$) using a Spectrophotometer. Lower absorbance value (at 600 nm wavelength) indicates higher clarity and solubility of the sample solution.

Figure 21:
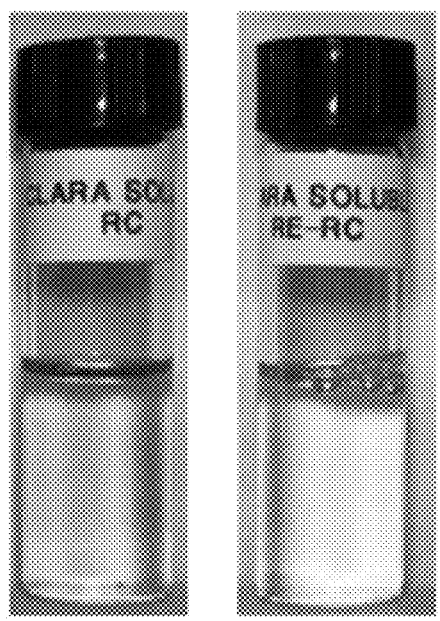
FIG. 21 indicates the color of an rOVD solution without (left) and with (right) hydrogen peroxide treatment.

The hydrogen peroxide-treated sample had lower absorbance (Table 27) and a paler color compared to the control. This indicated that the treatment resulted in improved appearance, in terms of less intense color and clear solution. These features are illustrated in FIG. 21.

TABLE 27

Absorbance (at 600 nm) of sample solutions (4.23% w/v)

|  | rOVD | H₂O₂ Reprocessed RE-RC |
|---|---|---|
| Absorbance | 0.068 | 0.046 |

Example 24: Protein Bar Preparation and Testing for Hardness and Sensory Likeability Homogenous mixtures of chopped dates chopped nuts (almonds and walnuts), and cocoa was combined with a protein powder of interest as shown in in Table 28. The amount of dates and nuts was reduced in formulations that included protein powders as seen in Table 29. The dates:nuts ratio was kept at a constant 4.6 level. Egg white protein powder and nOVD were prepared at inclusion levels of 2, 8, 16 or 23% while rOVD was prepared at inclusion levels of 2, 4, 8, 12, or 16%. (Table 28 to Table 31).

Half of each mixture was baked in an oven at 350 degrees F. for ten minutes. The other half of each mixture was tested as an unbaked mixture.

TABLE 28

List of Ingredients and their proportions used in control formulation

| Ingredients | Amount (%) |
|---|---|
| Dates | 78.67 |
| Nuts | 17.33 |
| Cocoa | 4 |
| Total | 100 |

TABLE 29

List of Ingredients and their proportions used in egg white protein formulations

| Ingredients | 2% protein | 8% protein | 16% protein | 23% protein | 32% protein |
|---|---|---|---|---|---|
| Dates | 76.67 | 71 | 63.33 | 56.67 | 48 |
| Nuts | 17 | 15.67 | 14 | 12.50 | 10.67 |
| Cocoa | 4 | 4 | 4 | 4 | 4 |
| Protein | 2.33 | 9.33 | 18.67 | 26.83 | 37.33 |
| Total | 100 | 100 | 100 | 100 | 100 |

TABLE 30

List of Ingredients and their proportions used in nOVD formulations

| Ingredients | 2% protein | 8% protein | 16% protein | 23% protein |
|---|---|---|---|---|
| Dates | 76.67 | 70.67 | 62.33 | 55.25 |
| Nuts | 16.83 | 15.33 | 13.67 | 12 |
| Cocoa | 4 | 4 | 4 | 4 |
| Protein | 2.5 | 10 | 20 | 28.75 |
| Total | 100 | 100 | 100 | 100 |

TABLE 31

List of Ingredients and their proportions used in rOVD formulations:

| Ingredients | 2% protein | 4% protein | 8% protein | 12% protein | 16% protein |
|---|---|---|---|---|---|
| Dates | 76.71 | 74.95 | 71.14 | 67.28 | 63.61 |
| Nuts | 16.99 | 16.46 | 15.66 | 14.93 | 14 |
| Cocoa | 4 | 4 | 4 | 4 | 4 |
| Protein | 2.3 | 4.59 | 9.20 | 13.79 | 18.39 |
| Total | 100 | 100 | 100 | 100 | 100 |

Example 25: Protein Bar Hardness/Texture Test

The textural properties of the baked and unbaked protein bars as prepared in Example 25 were measured using a CT3 Brookfield Texture Analyzer (1500 g load cell). A three-point bend test was used to snap, bend and measure the hardness of the protein bars. One sample for each protein inclusion level was analyzed. The test parameters used are shown in Table 32.

The hardness results for the baked protein bars were much higher than the hardness results in the unbaked version. Within the unbaked protein bars, 8% inclusion for all protein powders resulted in similar hardness values. Hardness profile for all unbaked protein bars gradually increased as the protein inclusion rates increased. Hardness values at 16% and 23% protein inclusion were also comparable for egg white protein, native OVD and rOVD. See, Table 33 and Table 34.

Egg white protein could be included up to 32% protein levels. A maximum of 23% protein inclusion levels in a protein bar, was observed for native and rOVD. Higher protein concentrations were unable to incorporate in a protein bar form.

The hardness value for nOVD at 8% inclusion level was much lower than egg white protein and rOVD. However, similar hardness values were observed for all protein bar samples at an inclusion level of 16% and 23%. The baked protein bars with native and rOVD exhibited a porous crumb and hard outer shell for higher inclusion levels of 16% and 23%. Overall, 8% protein powder inclusion level was the most desirable (higher palatability and texture attributes) across all protein powders.

TABLE 32

Test parameters used for three-point bend test to measure hardness using a CT3 Brookfield Texture Analyzer

| | |
|---|---|
| Test type | Rupture test |
| Probe | TA7 blade |
| Base Fixture | TA-TPB |
| Trigger load | 5 g |
| Correction load | 30 g |
| Test speed | 3 mm/s |
| Sample rate | 30 points/sec |
| Distance between support arms | 2.5 cm |
| Textural properties | Hardness (g) |

TABLE 33

Test results for unbaked protein bar samples

| | Hardness (g) for protein inclusion levels | | | | | |
|---|---|---|---|---|---|---|
| Sample | Control (0%) | 8% | 12% | 16% | 23% | 32% |
| Egg white protein | 86.33 | 186.2 | 386.6 | 299.2 | 434.6 | 393.6 |
| nOVD | | 173.2 | 463.8 | 360 | 411 | n/a |
| rOVD | | 182.2 | 291.2 | 338.2 | 402.4 | n/a |

TABLE 34

Test results for baked protein bar samples

| | Hardness (g) for protein inclusion levels | | | | | |
|---|---|---|---|---|---|---|
| Sample | Control (0%) | 8% | 12% | 16% | 23% | 32% |
| Egg white protein | 1193 | 1525.2 | 1490 | 1544.4 | 1506.6 | 1534.2 |
| nOVD | | 1072.8 | 1054.4 | 1506.2 | 1433.8 | n/a |
| rOVD | | 1380.4 | 1499 | 1504 | 1565.4 | n/a |

Example 26: Protein Bar Sensory Test

Samples prepared as described in Example 26 were evaluated for quality descriptors by trained in-house panelists.

The quality attributes tested included appearance, smell, taste/flavor, mouthfeel/texture and overall liking in a nine-point scale from 1: Dislike extremely, 2: Dislike very much, 3: Dislike moderately, 4: Dislike slightly, 5: Neither like nor dislike, 6: Like slightly, 7: Like moderately, 8: Like very much, and 9: Like extremely.

TABLE 35

Sensory likeability results for 8% protein bar samples

| | 8% Protein inclusion (Unbaked) | | | | 8% Protein inclusion (Baked) | | | |
|---|---|---|---|---|---|---|---|---|
| Attribute Likeability | Unbaked Control | Egg white protein | nOVD | rOVD | Baked Control | Egg white protein | nOVD | rOVD |
| Appearance | 8 | 7.5 | 8 | 6.5 | 9 | 7.5 | 8 | 6.5 |
| Smell | 9 | 8 | 9 | 8 | 9 | 7 | 9 | 8 |
| Taste/Flavor | 9 | 6.5 | 4 | 7 | 9 | 6 | 4 | 7 |
| Texture/Mouthfeel | 6 | 6 | 4.5 | 8 | 9 | 4 | 4.5 | 8 |
| Overall | 7 | 7 | 4 | 7 | 9 | 5 | 4 | 7 |

For the control unbaked sample, panelists noted that it had a good appearance, slightly soft texture/bite but overall good taste and no unpleasant aftertaste. For the baked version, panelists liked every attribute of the sample to the highest score and gave it a perfect score.

For the unbaked (8%) protein bars, panelists provided the following comments: the egg white protein bar tasted like tootsie roll, it was sweet and cohesive but had a dry mouthfeel; the native OVD bar was less sticky as compared to control but had a strong OVD-like, metallic and acidic taste and with a dry mouthfeel; and the rOVD bar had no acidity, was slightly less sweet but was cohesive and had a pleasant aftertaste.

For the baked (8%) protein bars, panelists provided the following comments: the egg white protein bar was slightly acidic, had a cracker/toasted cereal like taste and aftertaste; the native OVD bar was harder and tacky as compared to control and was more palatable; and the rOVD bars lacked acidity, were chewy, and tacky which the panelists liked.

TABLE 36

Sensory likeability results for 16% protein bar samples

| Attribute Likeability | Unbaked Control | 16% Protein inclusion (Unbaked) | | | Baked Control | 16% Protein inclusion (Baked) | | |
|---|---|---|---|---|---|---|---|---|
| | | Egg white protein | nOVD | rOVD | | Egg white protein | nOVD | rOVD |
| Appearance | 8 | 7 | 8 | 5 | 9 | 5 | 6 | 5 |
| Smell | 9 | 5.5 | 7 | 5.5 | 9 | 2 | 7 | 5 |
| Taste/Flavor | 9 | 5 | 1 | 7 | 9 | 3 | 1 | 6 |
| Texture/Mouthfeel | 6 | 4 | −1 | 8 | 9 | 2 | 1 | 2 |
| Overall | 7 | 4 | 1 | 6.5 | 9 | 2 | 2 | 6 |

For the baked (16%) protein bars, panelists provided the following comments: the egg white protein bar tasted toasted and bready, was whiteish and had a powdery mouthfeel; the nOVD bar was very hard and difficult to bite, looked like a hard bread, had a strong sour taste which left a burning sensation; the rOVD bar had muted sweetness, a mealy and a toasty flavor, with no acidity or aftertaste, and it was tacky but hard.

Overall, rOVD bars performed better than nOVD bars and comparable to egg white protein samples in tests described in Example 25 to Example 27. A maximum of 23% protein inclusion for nOVD and rOVD seemed possible while egg white protein samples were able to go as high as 32% inclusion levels. Eight percent bars were deemed as the best inclusion levels for all the protein bars.

Twelve percent rOVD bars had slight acidity in the unbaked bars, however no acidity was perceived in the baked bars. The baked bars were chewy, tacky and hard.

Example 27: rOVD Salad Dressing

A salad dressing was prepared using a L5M-A homogenizer (Silverson) at ambient temperature. Emulsions were prepared by dispersing protein powder and salt into the aqueous phase (water and vinegar) and stirring at 2000 rpm for 5 minutes using General Purpose Disintegrating Head. After mixing, canola oil was added in a controlled manner and homogenized at 6000 rpm for 15 minutes using Square Hole High Shear Screen to make a stable oil-in-water emulsion.

All emulsion samples were transferred into glass tubes, sealed with a plastic cap, and stored at 4 C for seven days. The stabilities of the samples were evaluated by visually monitoring the height of the visible serum separation at the bottom phase with storage time. Physical stability was monitored until no visual phase separation happened. The stability of the emulsion was expressed as: % serum=(Ht/H0)*100. H0 represents the initial emulsion height and the height of visible serum separation layer (Ht).

List of ingredients and their proportions used in the control and other salad dressing samples with specific protein of interest were presented (Table 37).

TABLE 37

List of Ingredients.

| Ingredient | Control % | nOVD 9% % | rOVD 9% % |
|---|---|---|---|
| Canola oil | 45 | 45 | 45 |
| Water | 43.4 | 33.4 | 33.1 |
| Vinegar | 9.6 | 9.6 | 9.6 |
| Emulsifier | 0 | 10 | 10.3 |
| Salt | 2 | 2 | 2 |
| Total | 100.0 | 100.0 | 100 |

Table 38 presents the emulsion stability of the dressings with storage time. Both nOVD and rOVD samples showed better emulsion stability compared to the Control sample that underwent phase separation during the first day of storage at 4 C. After Day 2, samples containing nOVD and rOVD did not exhibit much change in the emulsion phase separation. Higher values indicate lower emulsion stability.

TABLE 38

Results of emulsion stability

| Time | sample | Emulsion stability % |
|---|---|---|
| Day 1 | 9% rOVD | 17 |
| | 9% nOVD | 15 |
| | Control | 44 |
| Day 2 | 9% rOVD | 29.4 |
| | 9% nOVD | 18.8 |
| | Control | 48.2 |

TABLE 38-continued

Results of emulsion stability

| Time | sample | Emulsion stability % |
| --- | --- | --- |
| Day 3 | 9% rOVD | 26 |
| | 9% nOVD | 21.3 |
| | Control | 47.2 |
| Day 7 | 9% rOVD | 26 |
| | 9% nOVD | 21.3 |
| | Control | 48.2 |
| Day 8 | 9% rOVD | 27.6 |
| | 9% nOVD | 23.3 |
| | Control | 49.1 |
| Day 9 | 9% rOVD | 25.6 |
| | 9% nOVD | 23.3 |
| | Control | 49.1 |

Example 28: rOVD Egg Wash Formation

The film formation and sheen formation functionality of rOVD was evaluated in a bread application. Baking instructions:
 a. In a small container, mix together yeast and sugar, and add warm water (85-95 F). Let it sit for 5 min
 b. Add the water in a mixing bowl
 c. Slowly mix in flour (30 sec) until a firm dough is formed (mix for 2 min on speed 3)
 d. Knead dough (folding 7 times) on a lightly floured board for 30 sec, adding small sprinkles of flour only as needed
 e. Place dough in a greased bowl. Flip dough over inside the bowl so that the dough top is also lightly greased. Cover and let rise for 45 minutes at 80 F proofing temperature (1st proof)
 f. Turn dough out onto a floured board and knead out air (fold 7 times)
 g. Shape into mini loaf and place in a greased mini pan
 h. Cover and let rise for 30 minutes at room temperature (2nd proof)
 i. Apply appropriate wash on top of the dough balls at a 3% level. (In case of sesame seed application, apply 10 sesame seeds to each dough ball over the wash)
 j. Bake at 350 F for 8 minutes or until golden brown (switch the location of the bread at 4 min to achieve even baking on all samples)
 k. 3% wash of total bread dough weight was added on top. 25 g samples each were used (total egg wash=0.75 g).
 l. For samples with whole egg and commercial egg wash substitute, 0.75 g of each sample was applied to the dough surface.

The formulations used for protein of interest are shown in Table 39:

TABLE 39

List of Ingredients and their proportions used in egg wash formulation:

| Ingredients | Egg white powder % | rOVD % |
| --- | --- | --- |
| DI water | 90.67 | 91.21 |
| Film forming agent | 9.33 | 8.79 |

Retention of sesame seeds: Retention of any topping on cake, bread, bagels or other baked goods is an important factor for egg wash. Sesame seeds were used to evaluate the binding function of each film forming agent post baking. 10 sesame seeds were applied to each dough ball post the application of wash and before baking. Retention of these sesame seeds was calculated based on the amount of seeds stuck to the bread post baking.

The following results were obtained:

TABLE 40

Retention levels of sesame seeds

| Samples | Negative Control | Commercial egg wash substitute | Whole egg | Egg white protein | rOVD |
| --- | --- | --- | --- | --- | --- |
| Retention level | 0% | 100% | 100% | 100% | 100% |

The control sample with no egg wash had no binding capacity for the sesame seeds and zero sesame seeds were retained on the surface post baking. However, all other film-forming agents were able to retain all 10 seeds post baking suggesting a 100% retention rate for toppings.

Colorimetric assay: Individual sample pictures were analyzed for color data in the RGB spectrum using the Colorgrab application (Loomatix). Sample values were generated using a 2×2 cm cross-section taken from the center of the bread surface. RGB data was then converted to a CIELAB system using the online software www.colormine.org. CIELAB model is a color space system that expresses color in 3 values: L* for the lightness from black (0) to white (100) a* from green (−) to red (+) b* from blue (−) to yellow (+).

TABLE 42

CIELAB results for bread post baking

| | L* | a* | b* |
| --- | --- | --- | --- |
| Negative Control | 63.669 | 1.10972 | 25.4527 |
| Whole egg | 62.255 | 8.39894 | 45.57611 |
| Commercial egg wash substitute | 68.349 | 0.04763 | 34.7033 |
| Egg white protein | 76.831 | 2.58977 | 31.1123 |
| rOVD | 83.591 | 4.58532 | 42.2485 | rOVD and egg white protein samples had a higher L* value suggesting higher brightness or luminance. Control (no egg wash), commercial egg wash substitute and egg white protein samples had a low a* value suggesting lower redness or brownness as compared to Whole egg, and rOVD samples.

Whole egg wash and rOVD samples also had similar b* values, suggesting similar yellow hues as compared to the other samples.

Figure 22:
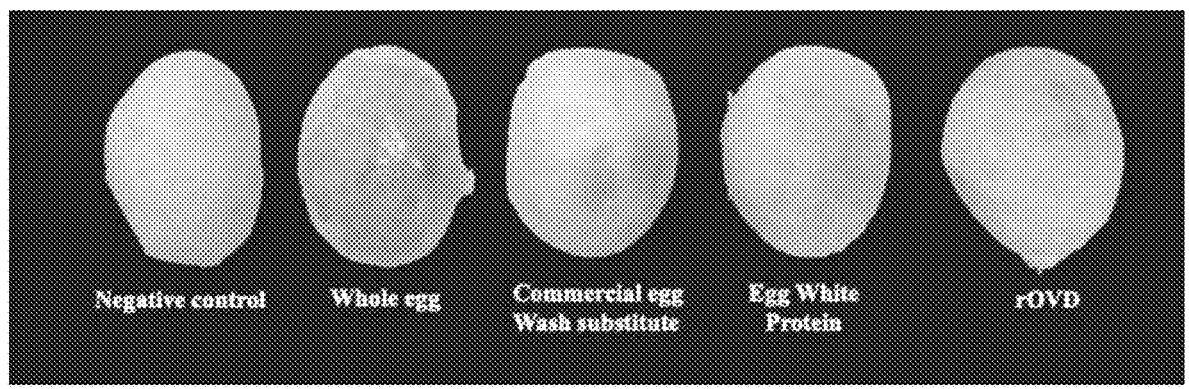
FIG. 22 illustrates a comparison of film formation using various protein samples.

Visual Inspection: The control sample looked pale, wrinkly and had no shine. The sample with egg-wash had good browning, great sheen and a smooth surface. The bake sheen sample had a smooth surface with a slight noticeable sheen. Egg white protein powder sample along with rOVD sample had a good sheen and browning.

rOVD worked well as a film forming and sheen forming agent. All the sesame seeds remained on the surface post browning suggesting good film forming and binding capabilities. The visual inspection and color values suggested good sheen formation and browning as compared to other samples (FIG. 22).

What is claimed is:

1. A composition comprising a recombinant ovomucoid protein (rOVD), wherein the rOVD comprises at least one glycosylated asparagine residue and the rOVD is substantially devoid of N-linked mannosylation,
   wherein the rOVD forms a clear solution at a concentration of from about 26% to about 30% w/v in an aqueous solution, at a pH of from about 2.5 to about 6, and at room temperature; and/or
   wherein a solution comprising the rOVD shows substantially higher solution clarity as compared to a whey protein solution at a concentration of 9% (w/v) in an aqueous solution, at a pH of from about 2 to about 6, and at the same temperature.

2. The composition of claim 1, wherein the composition is in powdered form.

3. The composition of claim 2, wherein the composition has a protein content of at least 50% rOVD protein w/w.

4. The composition of claim 1, wherein the composition comprises at least 0.1% rOVD protein w/w.

5. The composition of claim 1, wherein rOVD comprises a polypeptide represented by an amino acid sequence selected from the group consisting of SEQ ID No. 1-44 or an amino acid sequence having at least 97% sequence identity with SEQ ID No. 1-44.

6. The composition of claim 1, wherein rOVD is a chicken, turkey vulture, hummingbird, or goose rOVD.

7. The composition of claim 1, wherein the rOVD is expressed by a microbial organism selected from a *Pichia* species, a *Saccharomyces* species, a *Trichoderma* species, a *Pseudomonas* species, an *Aspergillus* species, and an *E. coli* species.

8. The composition of claim 7, wherein the microbial organism is a *Pichia* species.

9. A beverage composition comprising the composition of claim 1 and at least one consumable liquid, wherein the rOVD forms a clear solution in the composition, and wherein the concentration of rOVD is from about 0.1% w/v to about 30% w/v in an aqueous solution, at a pH of from about 2.5 to about 6, and at room temperature.

10. The beverage composition of claim 9, wherein the concentration of rOVD is about 10% w/v or less or about 20% w/v or less.

11. The beverage composition of claim 10, wherein the beverage composition is substantially optically clear.

12. The beverage composition of claim 9, wherein the beverage composition is selected from a cold beverage, a heated beverage, and a room-temperature beverage.

13. The beverage composition of claim 9, wherein the rOVD in the beverage composition remains substantially soluble after a heat treatment to a temperature between about 72° C. and about 121° C.

14. The beverage composition of claim 13, wherein the heat treatment is selected from hot fill, pasteurization, and retort.

15. The beverage composition of claim 9, wherein the beverage composition has a pH of between about 2.0 and about 6.0.

16. The beverage composition of claim 9, wherein the rOVD is substantially a full-length protein.

17. The beverage composition of claim 9, wherein the beverage composition is a beverage selected from a juice, a broth, a soup, a soda, a soft drink, a flavored water, a protein water, a fortified water, a carbonated water, a nutritional drink, an energy drink, a sports drink, a recovery drink, a heated drink, a coffee-based drink, a tea-based drink, a plant-based milk, a milk based drink, a non-dairy drink, plant-based milk drink, an infant formula drink, and a meal replacement drink.

18. The beverage composition of claim 9, further comprising a second protein, wherein the rOVD and the second protein together provide a protein digestibility-corrected amino acid score (PDCAAS) of greater than about 0.85.

19. The beverage composition of claim 18, wherein the second protein is an egg white lysozyme (OVL).

20. The beverage composition of claim 19, wherein the ratio of rOVD to OVL is between about 60% rOVD:40% OVL and about 82% rOVD:18% OVL.

* * * * *

SEQUENCE LISTING

<160> NUMBER OF SEQ ID NOS: 53

<210> SEQ ID NO 1
<211> LENGTH: 186
<212> TYPE: PRT
<213> ORGANISM: Gallus gallus

<400> SEQUENCE: 1

```
Ala Glu Val Asp Cys Ser Arg Phe Pro Asn Ala Thr Asp Lys Glu Gly
1               5                   10                  15

Lys Asp Val Leu Val Cys Asn Lys Asp Leu Arg Pro Ile Cys Gly Thr
            20                  25                  30

Asp Gly Val Thr Tyr Thr Asn Asp Cys Leu Leu Cys Ala Tyr Ser Ile
        35                  40                  45

Glu Phe Gly Thr Asn Ile Ser Lys Glu His Asp Gly Glu Cys Lys Glu
    50                  55                  60

Thr Val Pro Met Asn Cys Ser Ser Tyr Ala Asn Thr Thr Ser Glu Asp
65                  70                  75                  80

Gly Lys Val Met Val Leu Cys Asn Arg Ala Phe Asn Pro Val Cys Gly
                85                  90                  95

Thr Asp Gly Val Thr Tyr Asp Asn Glu Cys Leu Leu Cys Ala His Lys
            100                 105                 110

Val Glu Gln Gly Ala Ser Val Asp Lys Arg His Asp Gly Gly Cys Arg
        115                 120                 125

Lys Glu Leu Ala Ala Val Ser Val Asp Cys Ser Glu Tyr Pro Lys Pro
    130                 135                 140

Asp Cys Thr Ala Glu Asp Arg Pro Leu Cys Gly Ser Asp Asn Lys Thr
145                 150                 155                 160

Tyr Gly Asn Lys Cys Asn Phe Cys Asn Ala Val Val Glu Ser Asn Gly
                165                 170                 175

Thr Leu Thr Leu Ser His Phe Gly Lys Cys
            180                 185
```

<210> SEQ ID NO 2
<211> LENGTH: 186
<212> TYPE: PRT
<213> ORGANISM: Gallus gallus

<400> SEQUENCE: 2

```
Ala Glu Val Asp Cys Ser Arg Phe Pro Asn Ala Thr Asp Met Glu Gly
1               5                   10                  15

Lys Asp Val Leu Val Cys Asn Lys Asp Leu Arg Pro Ile Cys Gly Thr
            20                  25                  30

Asp Gly Val Thr Tyr Thr Asn Asp Cys Leu Leu Cys Ala Tyr Ser Val
        35                  40                  45

Glu Phe Gly Thr Asn Ile Ser Lys Glu His Asp Gly Glu Cys Lys Glu
    50                  55                  60

Thr Val Pro Met Asn Cys Ser Ser Tyr Ala Asn Thr Thr Ser Glu Asp
65                  70                  75                  80

Gly Lys Val Met Val Leu Cys Asn Arg Ala Phe Asn Pro Val Cys Gly
                85                  90                  95

Thr Asp Gly Val Thr Tyr Asp Asn Glu Cys Leu Leu Cys Ala His Lys
            100                 105                 110

Val Glu Gln Gly Ala Ser Val Asp Lys Arg His Asp Gly Gly Cys Arg
        115                 120                 125

Lys Glu Leu Ala Ala Val Ser Val Asp Cys Ser Glu Tyr Pro Lys Pro
```

Asp Cys Thr Ala Glu Asp Arg Pro Leu Cys Gly Ser Asp Asn Lys Thr
145                 150                 155                 160

Tyr Gly Asn Lys Cys Asn Phe Cys Asn Ala Val Val Glu Ser Asn Gly
            165                 170                 175

Thr Leu Thr Leu Ser His Phe Gly Lys Cys
            180                 185

<210> SEQ ID NO 3
<211> LENGTH: 186
<212> TYPE: PRT
<213> ORGANISM: Gallus gallus

<400> SEQUENCE: 3

Ala Glu Val Asp Cys Ser Arg Phe Pro Asn Ala Thr Asp Met Glu Gly
1               5                   10                  15

Lys Asp Val Leu Val Cys Asn Lys Asp Leu Arg Pro Ile Cys Gly Thr
            20                  25                  30

Asp Gly Val Thr Tyr Thr Asn Asp Cys Leu Leu Cys Ala Tyr Ser Val
        35                  40                  45

Glu Phe Gly Thr Asn Ile Ser Lys Glu His Asp Gly Glu Cys Lys Glu
50                  55                  60

Thr Val Pro Met Asn Cys Ser Ser Tyr Ala Asn Thr Thr Ser Glu Asp
65                  70                  75                  80

Gly Lys Val Met Val Leu Cys Asn Arg Ala Phe Asn Pro Val Cys Gly
            85                  90                  95

Thr Asp Gly Val Thr Tyr Asp Asn Glu Cys Leu Leu Cys Ala His Lys
        100                 105                 110

Val Glu Gln Gly Ala Ser Val Asp Lys Arg His Asp Gly Gly Cys Arg
    115                 120                 125

Lys Glu Leu Ala Ala Val Ser Val Asp Cys Ser Glu Tyr Pro Lys Pro
130                 135                 140

Asp Cys Thr Ala Glu Asp Arg Pro Leu Cys Gly Ser Asp Asn Lys Thr
145                 150                 155                 160

Tyr Met Asn Lys Cys Asn Ala Cys Asn Ala Val Val Glu Ser Asn Gly
            165                 170                 175

Thr Leu Thr Leu Ser His Phe Gly Lys Cys
            180                 185

<210> SEQ ID NO 4
<211> LENGTH: 210
<212> TYPE: PRT
<213> ORGANISM: Gallus gallus

<400> SEQUENCE: 4

Met Ala Met Ala Gly Val Phe Val Leu Phe Ser Phe Val Leu Cys Gly
1               5                   10                  15

Phe Leu Pro Asp Ala Ala Phe Gly Ala Glu Val Asp Cys Ser Arg Phe
            20                  25                  30

Pro Asn Ala Thr Asp Lys Glu Gly Lys Asp Val Leu Val Cys Asn Lys
        35                  40                  45

Asp Leu Arg Pro Ile Cys Gly Thr Asp Gly Val Thr Tyr Thr Asn Asp
        50                  55                  60

Cys Leu Leu Cys Ala Tyr Ser Ile Glu Phe Gly Thr Asn Ile Ser Lys
65                  70                  75                  80

Glu His Asp Gly Glu Cys Lys Glu Thr Val Pro Met Asn Cys Ser Ser

```
            85                  90                  95
Tyr Ala Asn Thr Thr Ser Glu Asp Gly Lys Val Met Val Leu Cys Asn
            100                 105                 110
Arg Ala Phe Asn Pro Val Cys Gly Thr Asp Gly Val Thr Tyr Asp Asn
            115                 120                 125
Glu Cys Leu Leu Cys Ala His Lys Val Glu Gln Gly Ala Ser Val Asp
            130                 135                 140
Lys Arg His Asp Gly Gly Cys Arg Lys Glu Leu Ala Ala Val Ser Val
145                 150                 155                 160
Asp Cys Ser Glu Tyr Pro Lys Pro Asp Cys Thr Ala Glu Asp Arg Pro
                165                 170                 175
Leu Cys Gly Ser Asp Asn Lys Thr Tyr Gly Asn Lys Cys Asn Phe Cys
                180                 185                 190
Asn Ala Val Val Glu Ser Asn Gly Thr Leu Thr Leu Ser His Phe Gly
                195                 200                 205
Lys Cys
    210

<210> SEQ ID NO 5
<211> LENGTH: 210
<212> TYPE: PRT
<213> ORGANISM: Gallus gallus

<400> SEQUENCE: 5

Met Ala Met Ala Gly Val Phe Val Leu Phe Ser Phe Val Leu Cys Gly
1               5                   10                  15
Phe Leu Pro Asp Ala Val Phe Gly Ala Glu Val Asp Cys Ser Arg Phe
                20                  25                  30
Pro Asn Ala Thr Asp Met Glu Gly Lys Asp Val Leu Val Cys Asn Lys
            35                  40                  45
Asp Leu Arg Pro Ile Cys Gly Thr Asp Gly Val Thr Tyr Thr Asn Asp
        50                  55                  60
Cys Leu Leu Cys Ala Tyr Ser Val Glu Phe Gly Thr Asn Ile Ser Lys
65                  70                  75                  80
Glu His Asp Gly Glu Cys Lys Glu Thr Val Pro Met Asn Cys Ser Ser
                85                  90                  95
Tyr Ala Asn Thr Thr Ser Glu Asp Gly Lys Val Met Val Leu Cys Asn
            100                 105                 110
Arg Ala Phe Asn Pro Val Cys Gly Thr Asp Gly Val Thr Tyr Asp Asn
            115                 120                 125
Glu Cys Leu Leu Cys Ala His Lys Val Glu Gln Gly Ala Ser Val Asp
            130                 135                 140
Lys Arg His Asp Gly Gly Cys Arg Lys Glu Leu Ala Ala Val Ser Val
145                 150                 155                 160
Asp Cys Ser Glu Tyr Pro Lys Pro Asp Cys Thr Ala Glu Asp Arg Pro
                165                 170                 175
Leu Cys Gly Ser Asp Asn Lys Thr Tyr Gly Asn Lys Cys Asn Phe Cys
                180                 185                 190
Asn Ala Val Val Glu Ser Asn Gly Thr Leu Thr Leu Ser His Phe Gly
                195                 200                 205
Lys Cys
    210

<210> SEQ ID NO 6
<211> LENGTH: 208
```

<212> TYPE: PRT
<213> ORGANISM: Gallus gallus

<400> SEQUENCE: 6

Met Ala Met Ala Gly Val Phe Val Leu Phe Ser Phe Val Leu Cys Gly
1               5                   10                  15

Phe Leu Pro Asp Ala Ala Phe Gly Ala Glu Val Asp Cys Ser Arg Phe
            20                  25                  30

Pro Asn Ala Thr Asp Lys Glu Gly Lys Asp Val Leu Val Cys Asn Lys
        35                  40                  45

Asp Leu Arg Pro Ile Cys Gly Thr Asp Gly Val Thr Tyr Thr Asn Asp
    50                  55                  60

Cys Leu Leu Cys Ala Tyr Ser Ile Glu Phe Gly Thr Asn Ile Ser Lys
65                  70                  75                  80

Glu His Asp Gly Glu Cys Lys Glu Thr Val Pro Met Asn Cys Ser Ser
                85                  90                  95

Tyr Ala Asn Thr Thr Ser Glu Asp Gly Lys Val Met Val Leu Cys Asn
            100                 105                 110

Arg Ala Phe Asn Pro Val Cys Gly Thr Asp Gly Val Thr Tyr Asp Asn
        115                 120                 125

Glu Cys Leu Leu Cys Ala His Lys Val Glu Gln Gly Ala Ser Val Asp
    130                 135                 140

Lys Arg His Asp Gly Gly Cys Arg Lys Glu Leu Ala Ala Val Asp Cys
145                 150                 155                 160

Ser Glu Tyr Pro Lys Pro Asp Cys Thr Ala Glu Asp Arg Pro Leu Cys
                165                 170                 175

Gly Ser Asp Asn Lys Thr Tyr Gly Asn Lys Cys Asn Phe Cys Asn Ala
            180                 185                 190

Val Val Glu Ser Asn Gly Thr Leu Thr Leu Ser His Phe Gly Lys Cys
        195                 200                 205

<210> SEQ ID NO 7
<211> LENGTH: 186
<212> TYPE: PRT
<213> ORGANISM: Gallus gallus

<400> SEQUENCE: 7

Ala Glu Val Asp Cys Ser Arg Phe Pro Asn Ala Thr Asp Lys Glu Gly
1               5                   10                  15

Lys Asp Val Leu Val Cys Asn Lys Asp Leu Arg Pro Ile Cys Gly Thr
            20                  25                  30

Asp Gly Val Thr Tyr Asn Asn Glu Cys Leu Leu Cys Ala Tyr Ser Ile
        35                  40                  45

Glu Phe Gly Thr Asn Ile Ser Lys Glu His Asp Gly Glu Cys Lys Glu
    50                  55                  60

Thr Val Pro Met Asn Cys Ser Ser Tyr Ala Asn Thr Thr Ser Glu Asp
65                  70                  75                  80

Gly Lys Val Met Val Leu Cys Asn Arg Ala Phe Asn Pro Val Cys Gly
                85                  90                  95

Thr Asp Gly Val Thr Tyr Asp Asn Glu Cys Leu Leu Cys Ala His Lys
            100                 105                 110

Val Glu Gln Gly Ala Ser Val Asp Lys Arg His Asp Gly Glu Cys Arg
        115                 120                 125

Lys Glu Leu Ala Ala Val Ser Val Asp Cys Ser Glu Tyr Pro Lys Pro
    130                 135                 140

```
Asp Cys Thr Ala Glu Asp Arg Pro Leu Cys Gly Ser Asp Asn Lys Thr
145                 150                 155                 160

Tyr Gly Asn Lys Cys Asn Phe Cys Asn Ala Val Val Glu Ser Asn Gly
                165                 170                 175

Thr Leu Thr Leu Ser His Phe Gly Lys Cys
            180                 185
```

```
<210> SEQ ID NO 8
<211> LENGTH: 208
<212> TYPE: PRT
<213> ORGANISM: Numida meleagris

<400> SEQUENCE: 8

Met Ala Met Ala Gly Val Phe Val Leu Phe Ser Phe Ala Leu Cys Gly
1               5                   10                  15

Phe Leu Pro Asp Ala Ala Phe Gly Val Glu Val Asp Cys Ser Arg Phe
                20                  25                  30

Pro Asn Ala Thr Asn Glu Glu Gly Lys Asp Val Leu Val Cys Thr Glu
            35                  40                  45

Asp Leu Arg Pro Ile Cys Gly Thr Asp Gly Val Thr Tyr Ser Asn Asp
50                  55                  60

Cys Leu Leu Cys Ala Tyr Asn Ile Glu Tyr Gly Thr Asn Ile Ser Lys
65                  70                  75                  80

Glu His Asp Gly Glu Cys Arg Glu Ala Val Pro Val Asp Cys Ser Arg
                85                  90                  95

Tyr Pro Asn Met Thr Ser Glu Glu Gly Lys Val Leu Ile Leu Cys Asn
                100                 105                 110

Lys Ala Phe Asn Pro Val Cys Gly Thr Asp Gly Val Thr Tyr Asp Asn
            115                 120                 125

Glu Cys Leu Leu Cys Ala His Asn Val Glu Gln Gly Thr Ser Val Gly
            130                 135                 140

Lys Lys His Asp Gly Glu Cys Arg Lys Glu Leu Ala Ala Val Asp Cys
145                 150                 155                 160

Ser Glu Tyr Pro Lys Pro Ala Cys Thr Met Glu Tyr Arg Pro Leu Cys
                165                 170                 175

Gly Ser Asp Asn Lys Thr Tyr Asp Asn Lys Cys Asn Phe Cys Asn Ala
            180                 185                 190

Val Val Glu Ser Asn Gly Thr Leu Thr Leu Ser His Phe Gly Lys Cys
            195                 200                 205
```

```
<210> SEQ ID NO 9
<211> LENGTH: 239
<212> TYPE: PRT
<213> ORGANISM: Meleagris gallopavo

<400> SEQUENCE: 9

Met Gln Thr Ile Thr Trp Arg Gln Pro Gln Gly Asp His Leu Arg Ser
1               5                   10                  15

Arg Ala Pro Ala Ala Thr Cys Arg Ala Gly Gln Tyr Leu Thr Met Ala
                20                  25                  30

Met Ala Gly Ile Phe Val Leu Phe Ser Phe Ala Leu Cys Gly Phe Leu
            35                  40                  45

Pro Asp Ala Ala Phe Gly Val Glu Val Asp Cys Ser Arg Phe Pro Asn
50                  55                  60

Thr Thr Asn Glu Glu Gly Lys Asp Val Leu Val Cys Thr Glu Asp Leu
65                  70                  75                  80
```

```
Arg Pro Ile Cys Gly Thr Asp Gly Val Thr His Ser Glu Cys Leu Leu
                85                  90                  95

Cys Ala Tyr Asn Ile Glu Tyr Gly Thr Asn Ile Ser Lys Glu His Asp
            100                 105                 110

Gly Glu Cys Arg Glu Ala Val Pro Met Asp Cys Ser Arg Tyr Pro Asn
            115                 120                 125

Thr Thr Asn Glu Glu Gly Lys Val Met Ile Leu Cys Asn Lys Ala Leu
        130                 135                 140

Asn Pro Val Cys Gly Thr Asp Gly Val Thr Tyr Asp Asn Glu Cys Val
145                 150                 155                 160

Leu Cys Ala His Asn Leu Glu Gln Gly Thr Ser Val Gly Lys Lys His
                165                 170                 175

Asp Gly Gly Cys Arg Lys Glu Leu Ala Ala Val Ser Val Asp Cys Ser
            180                 185                 190

Glu Tyr Pro Lys Pro Ala Cys Thr Leu Glu Tyr Arg Pro Leu Cys Gly
            195                 200                 205

Ser Asp Asn Lys Thr Tyr Gly Asn Lys Cys Asn Phe Cys Asn Ala Val
        210                 215                 220

Val Glu Ser Asn Gly Thr Leu Thr Leu Ser His Phe Gly Lys Cys
225                 230                 235
```

```
<210> SEQ ID NO 10
<211> LENGTH: 185
<212> TYPE: PRT
<213> ORGANISM: Meleagris gallopavo

<400> SEQUENCE: 10

Val Glu Val Asp Cys Ser Arg Phe Pro Asn Thr Thr Asn Glu Glu Gly
1               5                   10                  15

Lys Asp Val Leu Val Cys Thr Glu Asp Leu Arg Pro Ile Cys Gly Thr
            20                  25                  30

Asp Gly Val Thr His Ser Glu Cys Leu Leu Cys Ala Tyr Asn Ile Glu
        35                  40                  45

Tyr Gly Thr Asn Ile Ser Lys Glu His Asp Gly Glu Cys Arg Glu Ala
    50                  55                  60

Val Pro Met Asp Cys Ser Arg Tyr Pro Asn Thr Thr Ser Glu Glu Gly
65                  70                  75                  80

Lys Val Met Ile Leu Cys Asn Lys Ala Leu Asn Pro Val Cys Gly Thr
                85                  90                  95

Asp Gly Val Thr Tyr Asp Asn Glu Cys Val Leu Cys Ala His Asn Leu
            100                 105                 110

Glu Gln Gly Thr Ser Val Gly Lys Lys His Asp Gly Glu Cys Arg Lys
            115                 120                 125

Glu Leu Ala Ala Val Ser Val Asp Cys Ser Glu Tyr Pro Lys Pro Ala
        130                 135                 140

Cys Thr Leu Glu Tyr Arg Pro Leu Cys Gly Ser Asp Asn Lys Thr Tyr
145                 150                 155                 160

Gly Asn Lys Cys Asn Phe Cys Asn Ala Val Val Glu Ser Asn Gly Thr
                165                 170                 175

Leu Thr Leu Ser His Phe Gly Lys Cys
            180                 185

<210> SEQ ID NO 11
<211> LENGTH: 237
<212> TYPE: PRT
<213> ORGANISM: Meleagris gallopavo
```

<400> SEQUENCE: 11

```
Met Gln Thr Ile Thr Trp Arg Gln Pro Gln Gly Asp His Leu Arg Ser
 1               5                  10                  15

Arg Ala Pro Ala Ala Thr Cys Arg Ala Gly Gln Tyr Leu Thr Met Ala
            20                  25                  30

Met Ala Gly Ile Phe Val Leu Phe Ser Phe Ala Leu Cys Gly Phe Leu
        35                  40                  45

Pro Asp Ala Ala Phe Gly Val Glu Val Asp Cys Ser Arg Phe Pro Asn
50                  55                  60

Thr Thr Asn Glu Glu Gly Lys Asp Val Leu Val Cys Thr Glu Asp Leu
65                  70                  75                  80

Arg Pro Ile Cys Gly Thr Asp Gly Val Thr His Ser Glu Cys Leu Leu
                85                  90                  95

Cys Ala Tyr Asn Ile Glu Tyr Gly Thr Asn Ile Ser Lys Glu His Asp
            100                 105                 110

Gly Glu Cys Arg Glu Ala Val Pro Met Asp Cys Ser Arg Tyr Pro Asn
        115                 120                 125

Thr Thr Asn Glu Glu Gly Lys Val Met Ile Leu Cys Asn Lys Ala Leu
130                 135                 140

Asn Pro Val Cys Gly Thr Asp Gly Val Thr Tyr Asp Asn Glu Cys Val
145                 150                 155                 160

Leu Cys Ala His Asn Leu Glu Gln Gly Thr Ser Val Gly Lys Lys His
                165                 170                 175

Asp Gly Gly Cys Arg Lys Glu Leu Ala Ala Val Asp Cys Ser Glu Tyr
            180                 185                 190

Pro Lys Pro Ala Cys Thr Leu Glu Tyr Arg Pro Leu Cys Gly Ser Asp
        195                 200                 205

Asn Lys Thr Tyr Gly Asn Lys Cys Asn Phe Cys Asn Ala Val Val Glu
210                 215                 220

Ser Asn Gly Thr Leu Thr Leu Ser His Phe Gly Lys Cys
225                 230                 235
```

<210> SEQ ID NO 12
<211> LENGTH: 128
<212> TYPE: PRT
<213> ORGANISM: Bambusicola thoracicus

<400> SEQUENCE: 12

```
Glu Tyr Gly Thr Asn Ile Ser Ile Lys His Asn Gly Glu Cys Lys Glu
 1               5                  10                  15

Thr Val Pro Met Asp Cys Ser Arg Tyr Ala Asn Met Thr Asn Glu Glu
            20                  25                  30

Gly Lys Val Met Met Pro Cys Asp Arg Thr Tyr Asn Pro Val Cys Gly
        35                  40                  45

Thr Asp Gly Val Thr Tyr Asp Asn Glu Cys Gln Leu Cys Ala His Asn
    50                  55                  60

Val Glu Gln Gly Thr Ser Val Asp Lys Lys His Asp Gly Val Cys Gly
65                  70                  75                  80

Lys Glu Leu Ala Ala Val Ser Val Asp Cys Ser Glu Tyr Pro Lys Pro
                85                  90                  95

Glu Cys Thr Ala Glu Glu Arg Pro Ile Cys Gly Ser Asp Asn Lys Thr
            100                 105                 110

Tyr Gly Asn Lys Cys Asn Phe Cys Asn Ala Val Val Tyr Val Gln Pro
        115                 120                 125
```

<210> SEQ ID NO 13
<211> LENGTH: 195
<212> TYPE: PRT
<213> ORGANISM: Callipepla squamata

<400> SEQUENCE: 13

```
Val Asp Cys Ser Arg Phe Pro Asn Thr Thr Asn Glu Glu Gly Lys Asp
1               5                   10                  15

Val Leu Ala Cys Thr Lys Glu Leu His Pro Ile Cys Gly Thr Asp Gly
            20                  25                  30

Val Thr Tyr Ser Asn Glu Cys Leu Leu Cys Tyr Tyr Asn Ile Glu Tyr
        35                  40                  45

Gly Thr Asn Ile Ser Lys Glu His Asp Gly Glu Cys Thr Glu Ala Val
    50                  55                  60

Pro Val Asp Cys Ser Arg Tyr Pro Asn Thr Thr Ser Glu Glu Gly Lys
65                  70                  75                  80

Val Leu Ile Pro Cys Asn Arg Asp Phe Asn Pro Val Cys Gly Ser Asp
                85                  90                  95

Gly Val Thr Tyr Glu Asn Glu Cys Leu Leu Cys Ala His Asn Val Glu
            100                 105                 110

Gln Gly Thr Ser Val Gly Lys Lys His Asp Gly Gly Cys Arg Lys Glu
        115                 120                 125

Phe Ala Ala Val Ser Val Asp Cys Ser Glu Tyr Pro Lys Pro Asp Cys
    130                 135                 140

Thr Leu Glu Tyr Arg Pro Leu Cys Gly Ser Asp Asn Lys Thr Tyr Ala
145                 150                 155                 160

Ser Lys Cys Asn Phe Cys Asn Ala Val Val Ile Trp Glu Gln Glu Lys
                165                 170                 175

Asn Thr Arg His His Ala Ser His Ser Val Phe Phe Ile Ser Ala Arg
            180                 185                 190

Leu Val Cys
        195
```

<210> SEQ ID NO 14
<211> LENGTH: 339
<212> TYPE: PRT
<213> ORGANISM: Colinus virginianus

<400> SEQUENCE: 14

```
Met Leu Pro Leu Gly Leu Arg Glu Tyr Gly Thr Asn Thr Ser Lys Glu
1               5                   10                  15

His Asp Gly Glu Cys Thr Glu Ala Val Pro Val Asp Cys Ser Arg Tyr
            20                  25                  30

Pro Asn Thr Thr Ser Glu Glu Gly Lys Val Arg Ile Leu Cys Lys Lys
        35                  40                  45

Asp Ile Asn Pro Val Cys Gly Thr Asp Gly Val Thr Tyr Asp Asn Glu
    50                  55                  60

Cys Leu Leu Cys Ser His Ser Val Gly Gln Gly Ala Ser Ile Asp Lys
65                  70                  75                  80

Lys His Asp Gly Gly Cys Arg Lys Glu Phe Ala Ala Val Ser Val Asp
                85                  90                  95

Cys Ser Glu Tyr Pro Lys Pro Ala Cys Met Ser Glu Tyr Arg Pro Leu
            100                 105                 110

Cys Gly Ser Asp Asn Lys Thr Tyr Val Asn Lys Cys Asn Phe Cys Asn
        115                 120                 125
```

Ala Val Val Tyr Val Gln Pro Trp Leu His Ser Arg Cys Arg Leu Pro
            130                 135                 140

Pro Thr Gly Thr Ser Phe Leu Gly Ser Glu Gly Arg Glu Thr Ser Leu
145                 150                 155                 160

Leu Thr Ser Arg Ala Thr Asp Leu Gln Val Ala Gly Cys Thr Ala Ile
                165                 170                 175

Ser Ala Met Glu Ala Thr Arg Ala Ala Ala Leu Leu Gly Leu Val Leu
            180                 185                 190

Leu Ser Ser Phe Cys Glu Leu Ser His Leu Cys Phe Ser Gln Ala Ser
        195                 200                 205

Cys Asp Val Tyr Arg Leu Ser Gly Ser Arg Asn Leu Ala Cys Pro Arg
    210                 215                 220

Ile Phe Gln Pro Val Cys Gly Thr Asp Asn Val Thr Tyr Pro Asn Glu
225                 230                 235                 240

Cys Ser Leu Cys Arg Gln Met Leu Arg Ser Arg Ala Val Tyr Lys Lys
                245                 250                 255

His Asp Gly Arg Cys Val Lys Val Asp Cys Thr Gly Tyr Met Arg Ala
            260                 265                 270

Thr Gly Gly Leu Gly Thr Ala Cys Ser Gln Gln Tyr Ser Pro Leu Tyr
        275                 280                 285

Ala Thr Asn Gly Val Ile Tyr Ser Asn Lys Cys Thr Phe Cys Ser Ala
    290                 295                 300

Val Ala Asn Gly Glu Asp Ile Asp Leu Leu Ala Val Lys Tyr Pro Glu
305                 310                 315                 320

Glu Glu Ser Trp Ile Ser Val Ser Pro Thr Pro Trp Arg Met Leu Ser
                325                 330                 335

Ala Gly Ala

<210> SEQ ID NO 15
<211> LENGTH: 238
<212> TYPE: PRT
<213> ORGANISM: Anser cygnoides domesticus

<400> SEQUENCE: 15

Met Ser Trp Trp Gly Ile Lys Pro Ala Leu Glu Arg Pro Ser Gln Glu
1               5                   10                  15

Gln Ser Thr Ser Gly Gln Pro Val Asp Ser Gly Ser Thr Ser Thr Thr
            20                  25                  30

Thr Met Ala Gly Ile Phe Val Leu Leu Ser Leu Val Leu Cys Cys Phe
        35                  40                  45

Pro Asp Ala Ala Phe Gly Val Glu Val Asp Cys Ser Arg Phe Pro Asn
50                  55                  60

Thr Thr Asn Glu Glu Gly Lys Glu Val Leu Leu Cys Thr Lys Asp Leu
65                  70                  75                  80

Ser Pro Ile Cys Gly Thr Asp Gly Val Thr Tyr Ser Asn Glu Cys Leu
                85                  90                  95

Leu Cys Ala Tyr Asn Ile Glu Tyr Gly Thr Asn Ile Ser Lys Asp His
            100                 105                 110

Asp Gly Glu Cys Lys Glu Ala Val Pro Val Asp Cys Ser Thr Tyr Pro
        115                 120                 125

Asn Met Thr Asn Glu Glu Gly Lys Val Met Leu Val Cys Asn Lys Met
    130                 135                 140

Phe Ser Pro Val Cys Gly Thr Asp Gly Val Thr Tyr Asn Asn Glu Cys
145                 150                 155                 160

```
Met Leu Cys Ala His Asn Val Glu Gln Gly Thr Ser Val Gly Lys Lys
                165                 170                 175

Tyr Asp Gly Lys Cys Lys Lys Glu Val Ala Thr Val Asp Cys Ser Asp
            180                 185                 190

Tyr Pro Lys Pro Ala Cys Thr Val Glu Tyr Met Pro Leu Cys Gly Ser
        195                 200                 205

Asp Asn Lys Thr Tyr Asp Asn Lys Cys Asn Phe Cys Asn Ala Val Val
    210                 215                 220

Asp Ser Asn Gly Thr Leu Thr Leu Ser His Phe Gly Lys Cys
225                 230                 235

<210> SEQ ID NO 16
<211> LENGTH: 284
<212> TYPE: PRT
<213> ORGANISM: Anser cygnoides domesticus

<400> SEQUENCE: 16

Met Ser Ser Gln Asn Gln Leu His Arg Arg Arg Pro Leu Pro Gly
1               5                   10                  15

Gly Gln Asp Leu Asn Lys Tyr Tyr Trp Pro His Cys Thr Ser Asp Arg
            20                  25                  30

Phe Ser Trp Leu Leu His Val Thr Ala Glu Gln Phe Arg His Cys Val
        35                  40                  45

Cys Ile Tyr Leu Gln Pro Ala Leu Glu Arg Pro Ser Gln Glu Gln Ser
    50                  55                  60

Thr Ser Gly Gln Pro Val Asp Ser Gly Ser Thr Ser Thr Thr Thr Met
65                  70                  75                  80

Ala Gly Ile Phe Val Leu Leu Ser Leu Val Leu Cys Cys Phe Pro Asp
                85                  90                  95

Ala Ala Phe Gly Val Glu Val Asp Cys Ser Arg Phe Pro Asn Thr Thr
            100                 105                 110

Asn Glu Glu Gly Lys Glu Val Leu Leu Cys Thr Lys Asp Leu Ser Pro
        115                 120                 125

Ile Cys Gly Thr Asp Gly Val Thr Tyr Ser Asn Glu Cys Leu Leu Cys
    130                 135                 140

Ala Tyr Asn Ile Glu Tyr Gly Thr Asn Ile Ser Lys Asp His Asp Gly
145                 150                 155                 160

Glu Cys Lys Glu Ala Val Pro Val Asp Cys Ser Thr Tyr Pro Asn Met
                165                 170                 175

Thr Asn Glu Glu Gly Lys Val Met Leu Val Cys Asn Lys Met Phe Ser
            180                 185                 190

Pro Val Cys Gly Thr Asp Gly Val Thr Tyr Asp Asn Glu Cys Met Leu
        195                 200                 205

Cys Ala His Asn Val Glu Gln Gly Thr Ser Val Gly Lys Lys Tyr Asp
    210                 215                 220

Gly Lys Cys Lys Lys Glu Val Ala Thr Val Asp Cys Ser Asp Tyr Pro
225                 230                 235                 240

Lys Pro Ala Cys Thr Val Glu Tyr Met Pro Leu Cys Gly Ser Asp Asn
                245                 250                 255

Lys Thr Tyr Asp Asn Lys Cys Asn Phe Cys Asn Ala Val Val Asp Ser
            260                 265                 270

Asn Gly Thr Leu Thr Leu Ser His Phe Gly Lys Cys
        275                 280
```

-continued

```
<210> SEQ ID NO 17
<211> LENGTH: 186
<212> TYPE: PRT
<213> ORGANISM: Coturnix japonica

<400> SEQUENCE: 17
```

Val Glu Val Asp Cys Ser Arg Phe Pro Asn Thr Thr Asn Glu Glu Gly
1               5                   10                  15

Lys Asp Glu Val Val Cys Pro Asp Glu Leu Arg Leu Ile Cys Gly Thr
            20                  25                  30

Asp Gly Val Thr Tyr Asn His Glu Cys Met Leu Cys Phe Tyr Asn Lys
        35                  40                  45

Glu Tyr Gly Thr Asn Ile Ser Lys Glu Gln Asp Gly Glu Cys Gly Glu
    50                  55                  60

Thr Val Pro Met Asp Cys Ser Arg Tyr Pro Asn Thr Thr Ser Glu Asp
65                  70                  75                  80

Gly Lys Val Thr Ile Leu Cys Thr Lys Asp Phe Ser Phe Val Cys Gly
                85                  90                  95

Thr Asp Gly Val Thr Tyr Asp Asn Glu Cys Met Leu Cys Ala His Asn
            100                 105                 110

Val Val Gln Gly Thr Ser Val Gly Lys Lys His Asp Gly Glu Cys Arg
        115                 120                 125

Lys Glu Leu Ala Ala Val Ser Val Asp Cys Ser Glu Tyr Pro Lys Pro
    130                 135                 140

Ala Cys Pro Lys Asp Tyr Arg Pro Val Cys Gly Ser Asp Asn Lys Thr
145                 150                 155                 160

Tyr Ser Asn Lys Cys Asn Phe Cys Asn Ala Val Val Glu Ser Asn Gly
                165                 170                 175

Thr Leu Thr Leu Asn His Phe Gly Lys Cys
            180                 185

```
<210> SEQ ID NO 18
<211> LENGTH: 210
<212> TYPE: PRT
<213> ORGANISM: Coturnix japonica

<400> SEQUENCE: 18
```

Met Ala Met Ala Gly Val Phe Leu Leu Phe Ser Phe Ala Leu Cys Gly
1               5                   10                  15

Phe Leu Pro Asp Ala Ala Phe Gly Val Glu Val Asp Cys Ser Arg Phe
            20                  25                  30

Pro Asn Thr Thr Asn Glu Glu Gly Lys Asp Glu Val Val Cys Pro Asp
        35                  40                  45

Glu Leu Arg Leu Ile Cys Gly Thr Asp Gly Val Thr Tyr Asn His Glu
    50                  55                  60

Cys Met Leu Cys Phe Tyr Asn Lys Glu Tyr Gly Thr Asn Ile Ser Lys
65                  70                  75                  80

Glu Gln Asp Gly Glu Cys Gly Glu Thr Val Pro Met Asp Cys Ser Arg
                85                  90                  95

Tyr Pro Asn Thr Thr Ser Glu Asp Gly Lys Val Thr Ile Leu Cys Thr
            100                 105                 110

Lys Asp Phe Ser Phe Val Cys Gly Thr Asp Gly Val Thr Tyr Asp Asn
        115                 120                 125

Glu Cys Met Leu Cys Ala His Asn Ile Val Gln Gly Thr Ser Val Gly
    130                 135                 140

Lys Lys His Asp Gly Glu Cys Arg Lys Glu Leu Ala Ala Val Ser Val

```
                145                 150                 155                 160
Asp Cys Ser Glu Tyr Pro Lys Pro Ala Cys Pro Lys Asp Tyr Arg Pro
                    165                 170                 175

Val Cys Gly Ser Asp Asn Lys Thr Tyr Ser Asn Lys Cys Asn Phe Cys
                    180                 185                 190

Asn Ala Val Val Glu Ser Asn Gly Thr Leu Thr Leu Asn His Phe Gly
                    195                 200                 205

Lys Cys
    210

<210> SEQ ID NO 19
<211> LENGTH: 205
<212> TYPE: PRT
<213> ORGANISM: Anas platyrhynchos

<400> SEQUENCE: 19

Met Ala Gly Val Phe Val Leu Leu Ser Leu Val Leu Cys Cys Phe Pro
1               5                   10                  15

Asp Ala Ala Phe Gly Val Glu Val Asp Cys Ser Arg Phe Pro Asn Thr
                    20                  25                  30

Thr Asn Glu Glu Gly Lys Asp Val Leu Leu Cys Thr Lys Glu Leu Ser
                35                  40                  45

Pro Val Cys Gly Thr Asp Gly Val Thr Tyr Ser Asn Glu Cys Leu Leu
            50                  55                  60

Cys Ala Tyr Asn Ile Glu Tyr Gly Thr Asn Ile Ser Lys Asp His Asp
65                  70                  75                  80

Gly Glu Cys Lys Glu Ala Val Pro Ala Asp Cys Ser Met Tyr Pro Asn
                    85                  90                  95

Met Thr Asn Glu Glu Gly Lys Met Thr Leu Leu Cys Asn Lys Met Phe
                100                 105                 110

Ser Pro Val Cys Gly Thr Asp Gly Val Thr Tyr Asp Asn Glu Cys Met
                115                 120                 125

Leu Cys Ala His Asn Val Glu Gln Gly Thr Ser Val Gly Lys Lys Tyr
            130                 135                 140

Asp Gly Lys Cys Lys Lys Glu Val Ala Thr Val Asp Cys Ser Gly Tyr
145                 150                 155                 160

Pro Lys Pro Ala Cys Thr Met Glu Tyr Met Pro Leu Cys Gly Ser Asp
                    165                 170                 175

Asn Lys Thr Tyr Gly Asn Lys Cys Asn Phe Cys Asn Ala Val Val Asp
                    180                 185                 190

Ser Asn Gly Thr Leu Thr Leu Ser His Phe Gly Glu Cys
                    195                 200                 205

<210> SEQ ID NO 20
<211> LENGTH: 171
<212> TYPE: PRT
<213> ORGANISM: Anas platyrhynchos

<400> SEQUENCE: 20

Gln Val Asp Cys Ser Arg Phe Pro Asn Thr Thr Asn Glu Glu Gly Lys
1               5                   10                  15

Glu Val Leu Leu Cys Thr Lys Glu Leu Ser Pro Val Cys Gly Thr Asp
                20                  25                  30

Gly Val Thr Tyr Ser Asn Glu Cys Leu Leu Cys Ala Tyr Asn Ile Glu
                35                  40                  45

Tyr Gly Thr Asn Ile Ser Lys Asp His Asp Gly Glu Cys Lys Glu Ala
```

```
            50                  55                  60
Val Pro Ala Asp Cys Ser Met Tyr Pro Asn Met Thr Asn Glu Glu Gly
 65                  70                  75                  80

Lys Met Thr Leu Leu Cys Asn Lys Met Phe Ser Pro Val Cys Gly Thr
                 85                  90                  95

Asp Gly Val Thr Tyr Asp Asn Glu Cys Met Leu Cys Ala His Asn Val
            100                 105                 110

Glu Gln Gly Thr Ser Val Gly Lys Lys Tyr Asp Gly Lys Cys Lys Lys
        115                 120                 125

Glu Val Ala Thr Val Ser Val Asp Cys Ser Gly Tyr Pro Lys Pro Ala
    130                 135                 140

Cys Thr Met Glu Tyr Met Pro Leu Cys Gly Ser Asp Asn Lys Thr Tyr
145                 150                 155                 160

Gly Asn Lys Cys Asn Phe Cys Asn Ala Val Val
                165                 170

<210> SEQ ID NO 21
<211> LENGTH: 207
<212> TYPE: PRT
<213> ORGANISM: Tyto alba

<400> SEQUENCE: 21

Met Thr Met Pro Gly Ala Phe Val Val Leu Ser Phe Val Leu Cys Cys
 1               5                  10                  15

Phe Pro Asp Ala Thr Phe Gly Val Glu Val Asp Cys Ser Thr Tyr Pro
            20                  25                  30

Asn Thr Asn Glu Glu Gly Lys Glu Val Leu Val Cys Ser Lys Ile
         35                  40                  45

Leu Ser Pro Ile Cys Gly Thr Asp Gly Val Thr Tyr Ser Asn Glu Cys
 50                  55                  60

Leu Leu Cys Ala Asn Asn Ile Glu Tyr Gly Thr Asn Ile Ser Lys Tyr
 65                  70                  75                  80

His Asp Gly Glu Cys Lys Glu Phe Val Pro Val Asn Cys Ser Arg Tyr
                 85                  90                  95

Pro Asn Thr Thr Asn Glu Glu Gly Lys Val Met Leu Ile Cys Asn Lys
            100                 105                 110

Asp Leu Ser Pro Val Cys Gly Thr Asp Gly Val Thr Tyr Asp Asn Glu
        115                 120                 125

Cys Leu Leu Cys Ala His Asn Leu Glu Pro Gly Thr Ser Val Gly Lys
    130                 135                 140

Lys Tyr Asp Gly Glu Cys Lys Lys Glu Ile Ala Thr Val Asp Cys Ser
145                 150                 155                 160

Asp Tyr Pro Lys Pro Val Cys Ser Leu Glu Ser Met Pro Leu Cys Gly
                165                 170                 175

Ser Asp Asn Lys Thr Tyr Ser Asn Lys Cys Asn Phe Cys Asn Ala Val
            180                 185                 190

Val Asp Ser Asn Glu Thr Leu Thr Leu Ser His Phe Gly Lys Cys
        195                 200                 205

<210> SEQ ID NO 22
<211> LENGTH: 207
<212> TYPE: PRT
<213> ORGANISM: Balearica regulorum gibbericeps

<400> SEQUENCE: 22

Met Thr Met Ala Gly Val Phe Val Leu Leu Ser Phe Ala Leu Cys Cys
```

```
            1               5                  10                 15
Phe Pro Asp Ala Ala Phe Gly Val Glu Val Asp Cys Ser Thr Tyr Pro
            20                 25                 30

Asn Thr Thr Asn Glu Glu Gly Lys Glu Val Leu Val Cys Thr Lys Ile
            35                 40                 45

Leu Ser Pro Ile Cys Gly Thr Asp Gly Val Thr Tyr Ser Asn Glu Cys
            50                 55                 60

Leu Leu Cys Ala Tyr Asn Ile Glu Tyr Gly Thr Asn Val Ser Lys Asp
65                 70                 75                 80

His Asp Gly Glu Cys Lys Glu Val Val Pro Val Asp Cys Ser Arg Tyr
                85                 90                 95

Pro Asn Ser Thr Asn Glu Glu Gly Lys Val Val Met Leu Cys Ser Lys
            100                105                110

Asp Leu Asn Pro Val Cys Gly Thr Asp Gly Val Thr Tyr Asp Asn Glu
            115                120                125

Cys Val Leu Cys Ala His Asn Val Glu Ser Gly Thr Ser Val Gly Lys
            130                135                140

Lys Tyr Asp Gly Glu Cys Lys Lys Glu Thr Ala Thr Val Asp Cys Ser
145                150                155                160

Asp Tyr Pro Lys Pro Ala Cys Thr Leu Glu Tyr Met Pro Phe Cys Gly
                165                170                175

Ser Asp Ser Lys Thr Tyr Ser Asn Lys Cys Asn Phe Cys Asn Ala Val
                180                185                190

Val Asp Ser Asn Gly Thr Leu Thr Leu Ser His Phe Gly Lys Cys
            195                200                205
```

<210> SEQ ID NO 23
<211> LENGTH: 207
<212> TYPE: PRT
<213> ORGANISM: Cathartes aura

<400> SEQUENCE: 23

```
Met Thr Thr Ala Gly Val Phe Val Leu Leu Ser Phe Ala Leu Cys Ser
1               5                  10                 15

Phe Pro Asp Ala Ala Phe Gly Val Glu Val Asp Cys Ser Thr Tyr Pro
            20                 25                 30

Asn Thr Thr Asn Glu Glu Gly Lys Glu Val Leu Val Cys Thr Lys Ile
            35                 40                 45

Leu Ser Pro Ile Cys Gly Thr Asp Gly Val Tyr Ser Asn Glu Cys
            50                 55                 60

Leu Leu Cys Ala Tyr Asn Ile Glu Tyr Gly Thr Asn Val Ser Lys Asp
65                 70                 75                 80

His Asp Gly Glu Cys Lys Glu Phe Val Pro Val Asp Cys Ser Arg Tyr
                85                 90                 95

Pro Asn Thr Thr Asn Glu Asp Gly Lys Val Val Leu Leu Cys Asn Lys
            100                105                110

Asp Leu Ser Pro Ile Cys Gly Thr Asp Gly Val Thr Tyr Asp Asn Glu
            115                120                125

Cys Leu Leu Cys Ala Arg Asn Leu Glu Pro Gly Thr Ser Val Gly Lys
            130                135                140

Lys Tyr Asp Gly Glu Cys Lys Lys Glu Ile Ala Thr Val Asp Cys Ser
145                150                155                160

Asp Tyr Pro Lys Pro Val Cys Ser Leu Glu Tyr Met Pro Leu Cys Gly
                165                170                175
```

```
Ser Asp Ser Lys Thr Tyr Ser Asn Lys Cys Asn Phe Cys Asn Ala Val
            180                 185                 190

Val Asp Ser Asn Gly Thr Leu Thr Leu Ser His Phe Gly Lys Cys
        195                 200                 205

<210> SEQ ID NO 24
<211> LENGTH: 207
<212> TYPE: PRT
<213> ORGANISM: Cuculus canorus

<400> SEQUENCE: 24

Met Thr Thr Ala Gly Val Phe Val Leu Leu Ser Phe Thr Leu Cys Ser
1               5                   10                  15

Phe Pro Asp Ala Ala Phe Gly Val Glu Val Asp Cys Ser Pro Tyr Pro
            20                  25                  30

Asn Thr Thr Asn Glu Glu Gly Lys Glu Val Leu Val Cys Asn Lys Ile
        35                  40                  45

Leu Ser Pro Ile Cys Gly Thr Asp Gly Val Thr Tyr Ser Asn Glu Cys
    50                  55                  60

Leu Leu Cys Ala Tyr Asn Leu Glu Tyr Gly Thr Asn Ile Ser Lys Asp
65                  70                  75                  80

Tyr Asp Gly Glu Cys Lys Glu Val Ala Pro Val Asp Cys Ser Arg His
                85                  90                  95

Pro Asn Thr Thr Asn Glu Glu Gly Lys Val Glu Leu Cys Asn Lys
            100                 105                 110

Asp Leu Asn Pro Ile Cys Gly Thr Asn Gly Val Thr Tyr Asp Asn Glu
        115                 120                 125

Cys Leu Leu Cys Ala Arg Asn Leu Glu Ser Gly Thr Ser Ile Gly Lys
    130                 135                 140

Lys Tyr Asp Gly Glu Cys Lys Lys Glu Ile Ala Thr Val Asp Cys Ser
145                 150                 155                 160

Asp Tyr Pro Lys Pro Val Cys Thr Leu Glu Glu Met Pro Leu Cys Gly
                165                 170                 175

Ser Asp Asn Lys Thr Tyr Gly Asn Lys Cys Asn Phe Cys Asn Ala Val
            180                 185                 190

Val Asp Ser Asn Gly Thr Leu Thr Leu Ser His Phe Gly Lys Cys
        195                 200                 205

<210> SEQ ID NO 25
<211> LENGTH: 207
<212> TYPE: PRT
<213> ORGANISM: Antrostomus carolinensis

<400> SEQUENCE: 25

Met Thr Thr Ala Val Val Phe Val Leu Leu Ser Phe Ala Leu Cys Cys
1               5                   10                  15

Phe Pro Asp Ala Ala Phe Gly Val Glu Val Asp Cys Ser Thr Tyr Pro
            20                  25                  30

Asn Ser Thr Asn Glu Glu Gly Lys Asp Val Leu Val Cys Pro Lys Ile
        35                  40                  45

Leu Gly Pro Ile Cys Gly Thr Asp Gly Val Thr Tyr Ser Asn Glu Cys
    50                  55                  60

Leu Leu Cys Ala Tyr Asn Ile Gln Tyr Gly Thr Asn Val Ser Lys Asp
65                  70                  75                  80

His Asp Gly Glu Cys Lys Glu Ile Val Pro Val Asp Cys Ser Arg Tyr
                85                  90                  95
```

Pro Asn Thr Thr Asn Glu Glu Gly Lys Val Val Phe Leu Cys Asn Lys
            100                 105                 110

Asn Phe Asp Pro Val Cys Gly Thr Asp Gly Thr Tyr Asp Asn Glu
        115                 120                 125

Cys Met Leu Cys Ala Arg Ser Leu Glu Pro Gly Thr Thr Val Gly Lys
130                 135                 140

Lys His Asp Gly Glu Cys Lys Arg Glu Ile Ala Thr Val Asp Cys Ser
145                 150                 155                 160

Asp Tyr Pro Lys Pro Thr Cys Ser Ala Glu Asp Met Pro Leu Cys Gly
                165                 170                 175

Ser Asp Ser Lys Thr Tyr Ser Asn Lys Cys Asn Phe Cys Asn Ala Val
            180                 185                 190

Val Asp Ser Asn Gly Thr Leu Thr Leu Ser Arg Phe Gly Lys Cys
            195                 200                 205

<210> SEQ ID NO 26
<211> LENGTH: 207
<212> TYPE: PRT
<213> ORGANISM: Cariama cristata

<400> SEQUENCE: 26

Met Thr Met Thr Gly Val Phe Val Leu Leu Ser Phe Ala Ile Cys Cys
1               5                   10                  15

Phe Pro Asp Ala Ala Phe Gly Val Glu Val Asp Cys Ser Thr Tyr Pro
            20                  25                  30

Asn Thr Thr Asn Glu Glu Gly Lys Glu Val Leu Val Cys Thr Lys Ile
        35                  40                  45

Leu Ser Pro Ile Cys Gly Thr Asp Gly Val Thr Tyr Ser Asn Glu Cys
    50                  55                  60

Leu Leu Cys Ala Tyr Asn Ile Glu Tyr Gly Thr Asn Val Ser Lys Asp
65                  70                  75                  80

His Asp Gly Glu Cys Lys Glu Val Val Pro Val Asp Cys Ser Lys Tyr
                85                  90                  95

Pro Asn Thr Thr Asn Glu Glu Gly Lys Val Val Leu Leu Cys Ser Lys
            100                 105                 110

Asp Leu Ser Pro Val Cys Gly Thr Asp Gly Val Thr Tyr Asp Asn Glu
        115                 120                 125

Cys Leu Leu Cys Ala Arg Asn Leu Glu Pro Gly Ser Ser Val Gly Lys
130                 135                 140

Lys Tyr Asp Gly Glu Cys Lys Lys Glu Ile Ala Thr Ile Asp Cys Ser
145                 150                 155                 160

Asp Tyr Pro Lys Pro Val Cys Ser Leu Glu Tyr Met Pro Leu Cys Gly
                165                 170                 175

Ser Asp Ser Lys Thr Tyr Asp Asn Lys Cys Asn Phe Cys Asn Ala Val
            180                 185                 190

Val Asp Ser Asn Gly Thr Leu Thr Leu Ser His Phe Gly Lys Cys
            195                 200                 205

<210> SEQ ID NO 27
<211> LENGTH: 207
<212> TYPE: PRT
<213> ORGANISM: Pygoscelis adeliae

<400> SEQUENCE: 27

Met Thr Thr Ala Gly Val Phe Val Leu Leu Ser Phe Val Leu Cys Cys
1               5                   10                  15

```
Phe Pro Asp Ala Val Phe Gly Val Glu Val Asp Cys Ser Thr Tyr Pro
             20                  25                  30

Asn Thr Thr Asn Glu Glu Gly Lys Glu Val Leu Val Cys Thr Lys Ile
         35                  40                  45

Leu Ser Pro Ile Cys Gly Thr Asp Gly Val Thr Tyr Ser Asn Glu Cys
     50                  55                  60

Leu Leu Cys Ala Tyr Asn Ile Glu Tyr Gly Thr Asn Val Ser Lys Asp
 65                  70                  75                  80

His Asp Gly Glu Cys Lys Glu Val Val Pro Val Asn Cys Ser Arg Tyr
                 85                  90                  95

Pro Asn Thr Thr Asn Glu Glu Gly Lys Val Val Leu Arg Cys Ser Lys
            100                 105                 110

Asp Leu Ser Pro Val Cys Gly Thr Asp Gly Val Thr Tyr Asp Asn Glu
            115                 120                 125

Cys Leu Met Cys Ala Arg Asn Leu Glu Pro Gly Ala Val Val Gly Lys
            130                 135                 140

Asn Tyr Asp Gly Glu Cys Lys Lys Glu Ile Ala Thr Val Asp Cys Ser
145                 150                 155                 160

Asp Tyr Pro Lys Pro Val Cys Ser Leu Glu Tyr Met Pro Leu Cys Gly
                165                 170                 175

Ser Asp Ser Lys Thr Tyr Ser Asn Lys Cys Asn Phe Cys Asn Ala Val
            180                 185                 190

Val Asp Ser Asn Gly Thr Leu Thr Leu Ser His Phe Gly Lys Cys
            195                 200                 205

<210> SEQ ID NO 28
<211> LENGTH: 207
<212> TYPE: PRT
<213> ORGANISM: Nipponia nippon

<400> SEQUENCE: 28

Met Thr Thr Ala Gly Val Phe Val Leu Leu Ser Ile Ala Leu Cys Cys
  1               5                  10                  15

Phe Pro Asp Ala Ala Phe Gly Val Glu Val Asp Cys Ser Ala Tyr Ser
             20                  25                  30

Asn Thr Thr Ser Glu Glu Gly Lys Glu Val Leu Ser Cys Thr Lys Ile
         35                  40                  45

Leu Ser Pro Ile Cys Gly Thr Asp Gly Val Thr Tyr Ser Asn Glu Cys
     50                  55                  60

Leu Leu Cys Ala Tyr Asn Ile Glu Tyr Gly Thr Asn Ile Ser Lys Asp
 65                  70                  75                  80

His Asp Gly Glu Cys Lys Glu Val Val Ser Val Asp Cys Ser Arg Tyr
                 85                  90                  95

Pro Asn Thr Thr Asn Glu Glu Gly Lys Ala Val Leu Leu Cys Asn Lys
            100                 105                 110

Asp Leu Ser Pro Val Cys Gly Thr Asp Gly Val Thr Tyr Asp Asn Glu
            115                 120                 125

Cys Leu Leu Cys Ala His Asn Leu Glu Pro Gly Thr Ser Val Gly Lys
            130                 135                 140

Lys Tyr Asp Gly Ala Cys Lys Lys Glu Ile Ala Thr Val Asp Cys Ser
145                 150                 155                 160

Asp Tyr Pro Lys Pro Val Cys Thr Leu Glu Tyr Leu Pro Leu Cys Gly
                165                 170                 175

Ser Asp Ser Lys Thr Tyr Ser Asn Lys Cys Asp Phe Cys Asn Ala Val
            180                 185                 190
```

```
Val Asp Ser Asn Gly Thr Leu Thr Leu Ser His Phe Gly Lys Cys
        195                 200                 205

<210> SEQ ID NO 29
<211> LENGTH: 206
<212> TYPE: PRT
<213> ORGANISM: Phaethon lepturus

<400> SEQUENCE: 29

Met Thr Thr Ala Gly Val Phe Val Leu Leu Ser Phe Ala Leu Cys Cys
1               5                   10                  15

Phe Pro Asp Ala Ala Phe Gly Val Glu Val Asp Cys Ser Thr Tyr Pro
            20                  25                  30

Asn Thr Thr Asn Glu Glu Gly Lys Glu Val Leu Val Cys Thr Lys Ile
        35                  40                  45

Leu Ser Pro Ile Cys Gly Thr Asp Gly Thr Thr Tyr Ser Asn Glu Cys
    50                  55                  60

Leu Leu Cys Ala Tyr Asn Ile Glu Tyr Gly Thr Asn Val Ser Lys Asp
65                  70                  75                  80

His Asp Gly Glu Cys Lys Val Val Pro Val Asp Cys Ser Lys Tyr Pro
                85                  90                  95

Asn Thr Thr Asn Glu Asp Gly Lys Val Val Leu Leu Cys Asn Lys Ala
            100                 105                 110

Leu Ser Pro Ile Cys Gly Thr Asp Arg Val Thr Tyr Asp Asn Glu Cys
        115                 120                 125

Leu Met Cys Ala His Asn Leu Glu Pro Gly Thr Ser Val Gly Lys Lys
    130                 135                 140

His Asp Gly Glu Cys Gln Lys Glu Val Ala Thr Val Asp Cys Ser Asp
145                 150                 155                 160

Tyr Pro Lys Pro Val Cys Ser Leu Glu Tyr Met Pro Leu Cys Gly Ser
                165                 170                 175

Asp Gly Lys Thr Tyr Ser Asn Lys Cys Asn Phe Cys Asn Ala Val Val
            180                 185                 190

Asn Ser Asn Gly Thr Leu Thr Leu Ser His Phe Glu Lys Cys
        195                 200                 205

<210> SEQ ID NO 30
<211> LENGTH: 213
<212> TYPE: PRT
<213> ORGANISM: Melopsittacus undulatus

<400> SEQUENCE: 30

Met Thr Thr Ala Gly Val Phe Val Leu Leu Ser Phe Val Leu Cys Cys
1               5                   10                  15

Phe Phe Pro Asp Ala Ala Phe Gly Val Glu Val Asp Cys Ser Thr Tyr
            20                  25                  30

Pro Asn Thr Thr Asn Glu Glu Gly Lys Glu Val Leu Val Cys Ala Lys
        35                  40                  45

Ile Leu Ser Pro Val Cys Gly Thr Asp Gly Thr Tyr Ser Asn Glu
    50                  55                  60

Cys Leu Leu Cys Ala His Asn Ile Glu Asn Gly Thr Asn Val Gly Lys
65                  70                  75                  80

Asp His Asp Gly Lys Cys Lys Glu Ala Val Pro Val Asp Cys Ser Arg
                85                  90                  95

Tyr Pro Asn Thr Thr Asp Glu Glu Gly Lys Val Val Leu Leu Cys Asn
            100                 105                 110
```

```
Lys Asp Val Ser Pro Val Cys Gly Thr Asp Gly Val Thr Tyr Asp Asn
        115                 120                 125

Glu Cys Leu Leu Cys Ala His Asn Leu Glu Ala Gly Thr Ser Val Asp
    130                 135                 140

Lys Lys Asn Asp Ser Glu Cys Lys Thr Glu Asp Thr Thr Leu Ala Ala
145                 150                 155                 160

Val Ser Val Asp Cys Ser Asp Tyr Pro Lys Pro Val Cys Thr Leu Glu
                165                 170                 175

Tyr Leu Pro Leu Cys Gly Ser Asp Asn Lys Thr Tyr Ser Asn Lys Cys
            180                 185                 190

Arg Phe Cys Asn Ala Val Val Asp Ser Asn Gly Thr Leu Thr Leu Ser
            195                 200                 205

Arg Phe Gly Lys Cys
    210

<210> SEQ ID NO 31
<211> LENGTH: 207
<212> TYPE: PRT
<213> ORGANISM: Podiceps cristatus

<400> SEQUENCE: 31

Met Thr Thr Ala Gly Val Phe Val Leu Leu Ser Phe Ala Leu Cys Cys
1               5                   10                  15

Ser Pro Asp Ala Ala Phe Gly Val Glu Val Asp Cys Ser Thr Tyr Pro
                20                  25                  30

Asn Thr Thr Asn Glu Glu Gly Lys Glu Val Leu Ala Cys Thr Lys Ile
            35                  40                  45

Leu Ser Pro Ile Cys Gly Thr Asp Gly Val Thr Tyr Ser Asn Glu Cys
    50                  55                  60

Leu Leu Cys Ala Tyr Asn Met Glu Tyr Gly Thr Asn Val Ser Lys Asp
65                  70                  75                  80

His Asp Gly Lys Cys Lys Glu Val Val Pro Val Asp Cys Ser Arg Tyr
                85                  90                  95

Pro Asn Thr Thr Asn Glu Glu Gly Lys Val Val Leu Leu Cys Asn Lys
            100                 105                 110

Asp Leu Ser Pro Val Cys Gly Thr Asp Gly Val Thr Tyr Asp Asn Glu
        115                 120                 125

Cys Leu Leu Cys Ala Arg Asn Leu Glu Pro Gly Ala Ser Val Gly Lys
    130                 135                 140

Lys Tyr Asp Gly Glu Cys Lys Lys Glu Ile Ala Thr Val Asp Cys Ser
145                 150                 155                 160

Asp Tyr Pro Lys Pro Val Cys Ser Leu Glu His Met Pro Leu Cys Gly
                165                 170                 175

Ser Asp Ser Lys Thr Tyr Ser Asn Lys Cys Thr Phe Cys Asn Ala Val
            180                 185                 190

Val Asp Ser Asn Gly Thr Leu Thr Leu Ser His Phe Gly Lys Cys
            195                 200                 205

<210> SEQ ID NO 32
<211> LENGTH: 207
<212> TYPE: PRT
<213> ORGANISM: Fulmarus glacialis

<400> SEQUENCE: 32

Met Thr Thr Ala Gly Val Phe Val Leu Leu Ser Phe Ala Leu Cys Cys
1               5                   10                  15
```

```
Phe Pro Asp Ala Ala Phe Gly Val Glu Val Asp Cys Ser Thr Tyr Pro
            20                  25                  30

Asn Thr Thr Asn Glu Glu Gly Arg Glu Val Leu Val Cys Thr Lys Ile
            35                  40                  45

Leu Ser Pro Ile Cys Gly Thr Asp Gly Val Thr Tyr Ser Asn Glu Cys
 50                  55                  60

Leu Leu Cys Ala Tyr Asn Ile Glu Tyr Gly Thr Asn Val Ser Lys Asp
 65                  70                  75                  80

His Asp Gly Glu Cys Lys Glu Val Ala Pro Val Gly Cys Ser Arg Tyr
                85                  90                  95

Pro Asn Thr Thr Asn Glu Glu Gly Lys Val Val Leu Leu Cys Asn Lys
                100                 105                 110

Asp Leu Ser Pro Val Cys Gly Thr Asp Gly Val Thr Tyr Asp Asn Glu
            115                 120                 125

Cys Leu Leu Cys Ala Arg His Leu Glu Pro Gly Thr Ser Val Gly Lys
130                 135                 140

Lys Tyr Asp Gly Glu Cys Lys Lys Glu Ile Ala Thr Val Asp Cys Ser
145                 150                 155                 160

Asp Tyr Pro Lys Pro Val Cys Ser Leu Glu Tyr Met Pro Leu Cys Gly
                165                 170                 175

Ser Asp Ser Lys Thr Tyr Ser Asn Lys Cys Asn Phe Cys Asn Ala Val
            180                 185                 190

Leu Asp Ser Asn Gly Thr Leu Thr Leu Ser His Phe Gly Lys Cys
            195                 200                 205

<210> SEQ ID NO 33
<211> LENGTH: 207
<212> TYPE: PRT
<213> ORGANISM: Aptenodytes forsteri

<400> SEQUENCE: 33

Met Thr Thr Ala Gly Val Phe Val Leu Leu Ser Phe Ala Leu Cys Cys
1               5                   10                  15

Phe Pro Asp Ala Val Phe Gly Val Glu Val Asp Cys Ser Thr Tyr Pro
            20                  25                  30

Asn Thr Thr Asn Glu Glu Gly Lys Glu Val Leu Val Cys Thr Lys Ile
            35                  40                  45

Leu Ser Pro Ile Cys Gly Thr Asp Gly Val Thr Tyr Ser Asn Glu Cys
 50                  55                  60

Leu Leu Cys Ala Tyr Asn Ile Glu Tyr Gly Thr Asn Val Ser Lys Asp
 65                  70                  75                  80

His Asp Gly Glu Cys Lys Glu Val Val Pro Val Asp Cys Ser Arg Tyr
                85                  90                  95

Pro Asn Thr Thr Asn Glu Glu Gly Lys Val Val Leu Arg Cys Asn Lys
                100                 105                 110

Asp Leu Ser Pro Val Cys Gly Thr Asp Gly Val Thr Tyr Asp Asn Glu
            115                 120                 125

Cys Leu Met Cys Ala Arg Asn Leu Glu Pro Gly Ala Ile Val Gly Lys
130                 135                 140

Lys Tyr Asp Gly Glu Cys Lys Lys Glu Ile Ala Thr Val Asp Cys Ser
145                 150                 155                 160

Asp Tyr Pro Lys Pro Val Cys Ser Leu Glu Tyr Met Pro Leu Cys Gly
                165                 170                 175

Ser Asp Ser Lys Thr Tyr Ser Asn Lys Cys Asn Phe Cys Asn Ala Val
```

```
                    180                 185                 190

Val Asp Ser Asn Gly Thr Leu Ile Leu Ser His Phe Gly Lys Cys
                195                 200                 205

<210> SEQ ID NO 34
<211> LENGTH: 207
<212> TYPE: PRT
<213> ORGANISM: Pygoscelis adeliae

<400> SEQUENCE: 34

Met Thr Thr Ala Gly Val Phe Val Leu Leu Ser Phe Val Leu Cys Cys
1               5                   10                  15

Phe Pro Asp Ala Val Phe Gly Val Glu Val Asp Cys Ser Thr Tyr Pro
                20                  25                  30

Asn Thr Thr Asn Glu Glu Gly Lys Glu Val Leu Val Cys Thr Lys Ile
            35                  40                  45

Leu Ser Pro Ile Cys Gly Thr Asp Gly Val Tyr Ser Asn Glu Cys
        50                  55                  60

Leu Leu Cys Ala Tyr Asn Ile Glu Tyr Gly Thr Asn Val Ser Lys Asp
65                  70                  75                  80

His Asp Gly Glu Cys Lys Glu Val Val Pro Val Asp Cys Ser Arg Tyr
                85                  90                  95

Pro Asn Thr Thr Asn Glu Glu Gly Lys Val Val Leu Arg Cys Ser Lys
            100                 105                 110

Asp Leu Ser Pro Val Cys Gly Thr Asp Gly Val Thr Tyr Asp Asn Glu
        115                 120                 125

Cys Leu Met Cys Ala Arg Asn Leu Glu Pro Gly Ala Val Val Gly Lys
    130                 135                 140

Asn Tyr Asp Gly Glu Cys Lys Lys Glu Ile Ala Thr Val Asp Cys Ser
145                 150                 155                 160

Asp Tyr Pro Lys Pro Val Cys Ser Leu Glu Tyr Met Pro Leu Cys Gly
                165                 170                 175

Ser Asp Ser Lys Thr Tyr Ser Asn Lys Cys Asn Phe Cys Asn Ala Val
            180                 185                 190

Val Asp Ser Asn Gly Thr Leu Thr Leu Ser His Phe Gly Lys Cys
                195                 200                 205

<210> SEQ ID NO 35
<211> LENGTH: 282
<212> TYPE: PRT
<213> ORGANISM: Aptenodytes forsteri

<400> SEQUENCE: 35

Met Ser Ser Gln Asn Gln Leu Pro Ser Arg Cys Arg Pro Leu Pro Gly
1               5                   10                  15

Ser Gln Asp Leu Asn Lys Tyr Tyr Gln Pro His Cys Thr Gly Asp Arg
                20                  25                  30

Phe Cys Trp Leu Phe Tyr Val Thr Val Glu Gln Phe Arg His Cys Ile
            35                  40                  45

Cys Ile Tyr Leu Gln Leu Ala Leu Glu Arg Pro Ser His Glu Gln Ser
        50                  55                  60

Gly Gln Pro Ala Asp Ser Arg Asn Thr Ser Met Thr Thr Ala Gly
65                  70                  75                  80

Val Phe Val Leu Leu Ser Phe Ala Leu Cys Cys Phe Pro Asp Ala Val
                85                  90                  95

Phe Gly Val Glu Val Asp Cys Ser Thr Tyr Pro Asn Thr Thr Asn Glu
```

```
            100                 105                 110
Glu Gly Lys Glu Val Leu Val Cys Thr Lys Ile Leu Ser Pro Ile Cys
        115                 120                 125

Gly Thr Asp Gly Val Thr Tyr Ser Asn Glu Cys Leu Leu Cys Ala Tyr
    130                 135                 140

Asn Ile Glu Tyr Gly Thr Asn Val Ser Lys Asp His Asp Gly Glu Cys
145                 150                 155                 160

Lys Glu Val Val Pro Val Asp Cys Ser Arg Tyr Pro Asn Thr Thr Asn
                165                 170                 175

Glu Glu Gly Lys Val Val Leu Arg Cys Asn Lys Asp Leu Ser Pro Val
            180                 185                 190

Cys Gly Thr Asp Gly Val Thr Tyr Asp Asn Glu Cys Leu Met Cys Ala
        195                 200                 205

Arg Asn Leu Glu Pro Gly Ala Ile Val Gly Lys Lys Tyr Asp Gly Glu
    210                 215                 220

Cys Lys Lys Glu Ile Ala Thr Val Asp Cys Ser Asp Tyr Pro Lys Pro
225                 230                 235                 240

Val Cys Ser Leu Glu Tyr Met Pro Leu Cys Gly Ser Asp Ser Lys Thr
                245                 250                 255

Tyr Ser Asn Lys Cys Asn Phe Cys Asn Ala Val Val Asp Ser Asn Gly
            260                 265                 270

Thr Leu Ile Leu Ser His Phe Gly Lys Cys
        275                 280

<210> SEQ ID NO 36
<211> LENGTH: 193
<212> TYPE: PRT
<213> ORGANISM: Antrostomus carolinensis

<400> SEQUENCE: 36

Met Thr Thr Ala Val Val Phe Val Leu Leu Ser Phe Ala Leu Cys Cys
1               5                   10                  15

Phe Pro Asp Ala Ala Phe Gly Val Glu Val Asp Cys Ser Thr Tyr Pro
                20                  25                  30

Asn Ser Thr Asn Glu Glu Gly Lys Asp Val Leu Val Cys Pro Lys Ile
            35                  40                  45

Leu Gly Pro Ile Cys Gly Thr Asp Gly Val Thr Tyr Ser Asn Glu Cys
    50                  55                  60

Leu Leu Cys Ala Tyr Asn Ile Gln Tyr Gly Thr Asn Val Ser Lys Asp
65                  70                  75                  80

His Asp Gly Glu Cys Lys Glu Ile Val Pro Val Asp Cys Ser Arg Tyr
                85                  90                  95

Pro Asn Thr Thr Asn Glu Glu Gly Lys Val Val Phe Leu Cys Asn Lys
            100                 105                 110

Asn Phe Asp Pro Val Cys Gly Thr Asp Gly Thr Tyr Asp Asn Glu
        115                 120                 125

Cys Met Leu Cys Ala Arg Ser Leu Glu Pro Gly Thr Thr Val Gly Lys
130                 135                 140

Lys His Asp Gly Glu Cys Lys Arg Glu Ile Ala Thr Val Asp Cys Ser
145                 150                 155                 160

Asp Tyr Pro Lys Pro Thr Cys Ser Ala Glu Asp Met Pro Leu Cys Gly
                165                 170                 175

Ser Asp Ser Lys Thr Tyr Ser Asn Lys Cys Asn Phe Cys Asn Ala Val
            180                 185                 190
```

Val

<210> SEQ ID NO 37
<211> LENGTH: 190
<212> TYPE: PRT
<213> ORGANISM: Gallus gallus

<400> SEQUENCE: 37

```
Glu Ala Glu Ala Ala Glu Val Asp Cys Ser Arg Phe Pro Asn Ala Thr
1               5                   10                  15

Asp Lys Glu Gly Lys Asp Val Leu Val Cys Asn Lys Asp Leu Arg Pro
            20                  25                  30

Ile Cys Gly Thr Asp Gly Val Thr Tyr Thr Asn Asp Cys Leu Leu Cys
        35                  40                  45

Ala Tyr Ser Ile Glu Phe Gly Thr Asn Ile Ser Lys Glu His Asp Gly
    50                  55                  60

Glu Cys Lys Glu Thr Val Pro Met Asn Cys Ser Ser Tyr Ala Asn Thr
65                  70                  75                  80

Thr Ser Glu Asp Gly Lys Val Met Val Leu Cys Asn Arg Ala Phe Asn
                85                  90                  95

Pro Val Cys Gly Thr Asp Gly Val Thr Tyr Asp Asn Glu Cys Leu Leu
            100                 105                 110

Cys Ala His Lys Val Glu Gln Gly Ala Ser Val Asp Lys Arg His Asp
        115                 120                 125

Gly Gly Cys Arg Lys Glu Leu Ala Ala Val Ser Val Asp Cys Ser Glu
    130                 135                 140

Tyr Pro Lys Pro Asp Cys Thr Ala Glu Asp Arg Pro Leu Cys Gly Ser
145                 150                 155                 160

Asp Asn Lys Thr Tyr Gly Asn Lys Cys Asn Phe Cys Asn Ala Val Val
                165                 170                 175

Glu Ser Asn Gly Thr Leu Thr Leu Ser His Phe Gly Lys Cys
                180                 185                 190
```

<210> SEQ ID NO 38
<211> LENGTH: 199
<212> TYPE: PRT
<213> ORGANISM: Gallus gallus

<400> SEQUENCE: 38

```
Glu Glu Gly Val Ser Leu Glu Lys Arg Glu Ala Glu Ala Ala Glu Val
1               5                   10                  15

Asp Cys Ser Arg Phe Pro Asn Ala Thr Asp Lys Glu Gly Lys Asp Val
            20                  25                  30

Leu Val Cys Asn Lys Asp Leu Arg Pro Ile Cys Gly Thr Asp Gly Val
        35                  40                  45

Thr Tyr Thr Asn Asp Cys Leu Leu Cys Ala Tyr Ser Ile Glu Phe Gly
    50                  55                  60

Thr Asn Ile Ser Lys Glu His Asp Gly Glu Cys Lys Glu Thr Val Pro
65                  70                  75                  80

Met Asn Cys Ser Ser Tyr Ala Asn Thr Thr Ser Glu Asp Gly Lys Val
                85                  90                  95

Met Val Leu Cys Asn Arg Ala Phe Asn Pro Val Cys Gly Thr Asp Gly
            100                 105                 110

Val Thr Tyr Asp Asn Glu Cys Leu Leu Cys Ala His Lys Val Glu Gln
        115                 120                 125

Gly Ala Ser Val Asp Lys Arg His Asp Gly Gly Cys Arg Lys Glu Leu
```

```
                130                 135                 140
Ala Ala Val Ser Val Asp Cys Ser Glu Tyr Pro Lys Pro Asp Cys Thr
145                 150                 155                 160

Ala Glu Asp Arg Pro Leu Cys Gly Ser Asp Asn Lys Thr Tyr Gly Asn
                165                 170                 175

Lys Cys Asn Phe Cys Asn Ala Val Val Glu Ser Asn Gly Thr Leu Thr
            180                 185                 190

Leu Ser His Phe Gly Lys Cys
        195

<210> SEQ ID NO 39
<211> LENGTH: 275
<212> TYPE: PRT
<213> ORGANISM: Gallus gallus

<400> SEQUENCE: 39

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Val Asp Cys Ser Arg
                85                  90                  95

Phe Pro Asn Ala Thr Asp Lys Glu Gly Lys Asp Val Leu Val Cys Asn
                100                 105                 110

Lys Asp Leu Arg Pro Ile Cys Gly Thr Asp Gly Val Thr Tyr Thr Asn
            115                 120                 125

Asp Cys Leu Leu Cys Ala Tyr Ser Ile Glu Phe Gly Thr Asn Ile Ser
        130                 135                 140

Lys Glu His Asp Gly Glu Cys Lys Glu Thr Val Pro Met Asn Cys Ser
145                 150                 155                 160

Ser Tyr Ala Asn Thr Thr Ser Glu Asp Gly Lys Val Met Val Leu Cys
                165                 170                 175

Asn Arg Ala Phe Asn Pro Val Cys Gly Thr Asp Gly Val Thr Tyr Asp
                180                 185                 190

Asn Glu Cys Leu Leu Cys Ala His Lys Val Glu Gln Gly Ala Ser Val
            195                 200                 205

Asp Lys Arg His Asp Gly Gly Cys Arg Lys Glu Leu Ala Ala Val Ser
        210                 215                 220

Val Asp Cys Ser Glu Tyr Pro Lys Pro Asp Cys Thr Ala Glu Asp Arg
225                 230                 235                 240

Pro Leu Cys Gly Ser Asp Asn Lys Thr Tyr Gly Asn Lys Cys Asn Phe
                245                 250                 255

Cys Asn Ala Val Val Glu Ser Asn Gly Thr Leu Thr Leu Ser His Phe
                260                 265                 270

Gly Lys Cys
        275

<210> SEQ ID NO 40
<211> LENGTH: 273
```

```
<212> TYPE: PRT
<213> ORGANISM: Catharters aura

<400> SEQUENCE: 40

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Val Glu Val Asp Cys Ser Thr
                85                  90                  95

Tyr Pro Asn Thr Thr Asn Glu Glu Gly Lys Glu Val Leu Val Cys Thr
            100                 105                 110

Lys Ile Leu Ser Pro Ile Cys Gly Thr Asp Gly Val Thr Tyr Ser Asn
        115                 120                 125

Glu Cys Leu Leu Cys Ala Tyr Asn Ile Glu Tyr Gly Thr Asn Val Ser
    130                 135                 140

Lys Asp His Asp Gly Glu Cys Lys Glu Phe Val Pro Val Asp Cys Ser
145                 150                 155                 160

Arg Tyr Pro Asn Thr Thr Asn Glu Asp Gly Lys Val Val Leu Leu Cys
                165                 170                 175

Asn Lys Asp Leu Ser Pro Ile Cys Gly Thr Asp Gly Val Thr Tyr Asp
            180                 185                 190

Asn Glu Cys Leu Leu Cys Ala Arg Asn Leu Glu Pro Gly Thr Ser Val
        195                 200                 205

Gly Lys Lys Tyr Asp Gly Glu Cys Lys Lys Glu Ile Ala Thr Val Asp
    210                 215                 220

Cys Ser Asp Tyr Pro Lys Pro Val Cys Ser Leu Glu Tyr Met Pro Leu
225                 230                 235                 240

Cys Gly Ser Asp Ser Lys Thr Tyr Ser Asn Lys Cys Asn Phe Cys Asn
                245                 250                 255

Ala Val Val Asp Ser Asn Gly Thr Leu Thr Leu Ser His Phe Gly Lys
            260                 265                 270

Cys

<210> SEQ ID NO 41
<211> LENGTH: 188
<212> TYPE: PRT
<213> ORGANISM: Catharters aura

<400> SEQUENCE: 41

Glu Ala Glu Ala Val Glu Val Asp Cys Ser Thr Tyr Pro Asn Thr Thr
1               5                   10                  15

Asn Glu Glu Gly Lys Glu Val Leu Val Cys Thr Lys Ile Leu Ser Pro
            20                  25                  30

Ile Cys Gly Thr Asp Gly Val Thr Tyr Ser Asn Glu Cys Leu Leu Cys
        35                  40                  45

Ala Tyr Asn Ile Glu Tyr Gly Thr Asn Val Ser Lys Asp His Asp Gly
    50                  55                  60

Glu Cys Lys Glu Phe Val Pro Val Asp Cys Ser Arg Tyr Pro Asn Thr
```

```
                65                  70                  75                  80
Thr Asn Glu Asp Gly Lys Val Val Leu Leu Cys Asn Lys Asp Leu Ser
                    85                  90                  95

Pro Ile Cys Gly Thr Asp Gly Val Thr Tyr Asp Asn Glu Cys Leu Leu
                100                 105                 110

Cys Ala Arg Asn Leu Glu Pro Gly Thr Ser Val Gly Lys Lys Tyr Asp
                115                 120                 125

Gly Glu Cys Lys Lys Glu Ile Ala Thr Val Asp Cys Ser Asp Tyr Pro
                130                 135                 140

Lys Pro Val Cys Ser Leu Glu Tyr Met Pro Leu Cys Gly Ser Asp Ser
145                 150                 155                 160

Lys Thr Tyr Ser Asn Lys Cys Asn Phe Cys Asn Ala Val Val Asp Ser
                165                 170                 175

Asn Gly Thr Leu Thr Leu Ser His Phe Gly Lys Cys
                180                 185

<210> SEQ ID NO 42
<211> LENGTH: 206
<212> TYPE: PRT
<213> ORGANISM: Calypte anna

<400> SEQUENCE: 42

Met Thr Met Ala Gly Val Phe Val Leu Leu Ser Phe Ile Leu Cys Cys
1               5                   10                  15

Phe Pro Asp Thr Ala Phe Gly Val Glu Val Asp Cys Ser Ile Tyr Pro
                20                  25                  30

Asn Thr Thr Ser Glu Glu Gly Lys Glu Val Leu Val Cys Thr Glu Thr
                35                  40                  45

Leu Ser Pro Ile Cys Gly Ser Asp Gly Val Thr Tyr Asn Asn Glu Cys
            50                  55                  60

Gln Leu Cys Ala Tyr Asn Val Glu Tyr Gly Thr Asn Val Ser Lys Asp
65                  70                  75                  80

His Asp Gly Glu Cys Lys Glu Ile Val Pro Val Asp Cys Ser Arg Tyr
                85                  90                  95

Pro Asn Thr Thr Glu Glu Gly Arg Val Val Met Leu Cys Asn Lys Ala
                100                 105                 110

Leu Ser Pro Val Cys Gly Thr Asp Gly Val Thr Tyr Asp Asn Glu Cys
                115                 120                 125

Leu Leu Cys Ala Arg Asn Leu Glu Ser Gly Thr Ser Val Gly Lys Lys
                130                 135                 140

Phe Asp Gly Glu Cys Lys Lys Glu Ile Ala Thr Val Asp Cys Thr Asp
145                 150                 155                 160

Tyr Pro Lys Pro Val Cys Ser Leu Asp Tyr Met Pro Leu Cys Gly Ser
                165                 170                 175

Asp Ser Lys Thr Tyr Ser Asn Lys Cys Asn Phe Cys Asn Ala Val Met
                180                 185                 190

Asp Ser Asn Gly Thr Leu Thr Leu Asn His Phe Gly Lys Cys
                195                 200                 205

<210> SEQ ID NO 43
<211> LENGTH: 272
<212> TYPE: PRT
<213> ORGANISM: Calypte anna

<400> SEQUENCE: 43

Met Arg Phe Pro Ser Ile Phe Thr Ala Val Leu Phe Ala Ala Ser Ser
```

```
              1               5                  10                 15
           Ala Leu Ala Ala Pro Val Asn Thr Thr Thr Glu Asp Glu Thr Ala Gln
                          20                  25                 30

Ile Pro Ala Glu Ala Val Ile Gly Tyr Ser Asp Leu Glu Gly Asp Phe
                          35                  40                 45

Asp Val Ala Val Leu Pro Phe Ser Asn Ser Thr Asn Asn Gly Leu Leu
            50                  55                  60

Phe Ile Asn Thr Thr Ile Ala Ser Ile Ala Ala Lys Glu Glu Gly Val
           65                  70                  75                 80

Ser Leu Asp Lys Arg Glu Ala Glu Ala Val Glu Val Asp Cys Ser Ile
                          85                  90                 95

Tyr Pro Asn Thr Thr Ser Glu Glu Gly Lys Glu Val Leu Val Cys Thr
                          100                 105                110

Glu Thr Leu Ser Pro Ile Cys Gly Ser Asp Gly Val Thr Tyr Asn Asn
                          115                 120                125

Glu Cys Gln Leu Cys Ala Tyr Asn Val Glu Tyr Gly Thr Asn Val Ser
                          130                 135                140

Lys Asp His Asp Gly Glu Cys Lys Glu Ile Val Pro Val Asp Cys Ser
           145                 150                 155                160

Arg Tyr Pro Asn Thr Thr Glu Glu Gly Arg Val Val Met Leu Cys Asn
                          165                 170                175

Lys Ala Leu Ser Pro Val Cys Gly Thr Asp Gly Val Thr Tyr Asp Asn
                          180                 185                190

Glu Cys Leu Leu Cys Ala Arg Asn Leu Glu Ser Gly Thr Ser Val Gly
                          195                 200                205

Lys Lys Phe Asp Gly Glu Cys Lys Lys Glu Ile Ala Thr Val Asp Cys
                          210                 215                220

Thr Asp Tyr Pro Lys Pro Val Cys Ser Leu Asp Tyr Met Pro Leu Cys
           225                 230                 235                240

Gly Ser Asp Ser Lys Thr Tyr Ser Asn Lys Cys Asn Phe Cys Asn Ala
                          245                 250                255

Val Met Asp Ser Asn Gly Thr Leu Thr Leu Asn His Phe Gly Lys Cys
                          260                 265                270

<210> SEQ ID NO 44
<211> LENGTH: 187
<212> TYPE: PRT
<213> ORGANISM: Calypte anna

<400> SEQUENCE: 44

Glu Ala Glu Ala Val Glu Val Asp Cys Ser Ile Tyr Pro Asn Thr Thr
           1               5                   10                 15

Ser Glu Glu Gly Lys Glu Val Leu Val Cys Thr Glu Thr Leu Ser Pro
                          20                  25                 30

Ile Cys Gly Ser Asp Gly Val Thr Tyr Asn Asn Glu Cys Gln Leu Cys
                          35                  40                 45

Ala Tyr Asn Val Glu Tyr Gly Thr Asn Val Ser Lys Asp His Asp Gly
                          50                  55                 60

Glu Cys Lys Glu Ile Val Pro Val Asp Cys Ser Arg Tyr Pro Asn Thr
           65                  70                  75                 80

Thr Glu Glu Gly Arg Val Val Met Leu Cys Asn Lys Ala Leu Ser Pro
                          85                  90                 95

Val Cys Gly Thr Asp Gly Val Thr Tyr Asp Asn Glu Cys Leu Leu Cys
                          100                 105                110
```

```
Ala Arg Asn Leu Glu Ser Gly Thr Ser Val Gly Lys Phe Asp Gly
            115                 120                 125

Glu Cys Lys Lys Glu Ile Ala Thr Val Asp Cys Thr Asp Tyr Pro Lys
130                 135                 140

Pro Val Cys Ser Leu Asp Tyr Met Pro Leu Cys Gly Ser Asp Ser Lys
145                 150                 155                 160

Thr Tyr Ser Asn Lys Cys Asn Phe Cys Asn Ala Val Met Asp Ser Asn
                165                 170                 175

Gly Thr Leu Thr Leu Asn His Phe Gly Lys Cys
            180                 185
```

<210> SEQ ID NO 45
<211> LENGTH: 218
<212> TYPE: PRT
<213> ORGANISM: Gallus gallus

<400> SEQUENCE: 45

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Lys Val Phe Gly Arg Cys Glu
                85                  90                  95

Leu Ala Ala Ala Met Lys Arg His Gly Leu Asp Asn Tyr Arg Gly Tyr
            100                 105                 110

Ser Leu Gly Asn Trp Val Cys Ala Ala Lys Phe Glu Ser Asn Phe Asn
        115                 120                 125

Thr Gln Ala Thr Asn Arg Asn Thr Asp Gly Ser Thr Asp Tyr Gly Ile
130                 135                 140

Leu Gln Ile Asn Ser Arg Trp Trp Cys Asn Asp Gly Arg Thr Pro Gly
145                 150                 155                 160

Ser Arg Asn Leu Cys Asn Ile Pro Cys Ser Ala Leu Leu Ser Ser Asp
                165                 170                 175

Ile Thr Ala Ser Val Asn Cys Ala Lys Lys Ile Val Ser Asp Gly Asn
            180                 185                 190

Gly Met Asn Ala Trp Val Ala Trp Arg Asn Arg Cys Lys Gly Thr Asp
        195                 200                 205

Val Gln Ala Trp Ile Arg Gly Cys Arg Leu
210                 215
```

<210> SEQ ID NO 46
<211> LENGTH: 133
<212> TYPE: PRT
<213> ORGANISM: Gallus gallus

<400> SEQUENCE: 46

```
Glu Ala Glu Ala Lys Val Phe Gly Arg Cys Glu Leu Ala Ala Ala Met
1               5                   10                  15

Lys Arg His Gly Leu Asp Asn Tyr Arg Gly Tyr Ser Leu Gly Asn Trp
            20                  25                  30
```

```
Val Cys Ala Ala Lys Phe Glu Ser Asn Phe Asn Thr Gln Ala Thr Asn
             35                  40                  45

Arg Asn Thr Asp Gly Ser Thr Asp Tyr Gly Ile Leu Gln Ile Asn Ser
 50                  55                  60

Arg Trp Trp Cys Asn Asp Gly Arg Thr Pro Gly Ser Arg Asn Leu Cys
 65                  70                  75                  80

Asn Ile Pro Cys Ser Ala Leu Leu Ser Ser Asp Ile Thr Ala Ser Val
             85                  90                  95

Asn Cys Ala Lys Lys Ile Val Ser Asp Gly Asn Gly Met Asn Ala Trp
            100                 105                 110

Val Ala Trp Arg Asn Arg Cys Lys Gly Thr Asp Val Gln Ala Trp Ile
            115                 120                 125

Arg Gly Cys Arg Leu
            130

<210> SEQ ID NO 47
<211> LENGTH: 129
<212> TYPE: PRT
<213> ORGANISM: Gallus gallus

<400> SEQUENCE: 47

Lys Val Phe Gly Arg Cys Glu Leu Ala Ala Ala Met Lys Arg His Gly
 1               5                  10                  15

Leu Asp Asn Tyr Arg Gly Tyr Ser Leu Gly Asn Trp Val Cys Ala Ala
             20                  25                  30

Lys Phe Glu Ser Asn Phe Asn Thr Gln Ala Thr Asn Arg Asn Thr Asp
             35                  40                  45

Gly Ser Thr Asp Tyr Gly Ile Leu Gln Ile Asn Ser Arg Trp Trp Cys
 50                  55                  60

Asn Asp Gly Arg Thr Pro Gly Ser Arg Asn Leu Cys Asn Ile Pro Cys
 65                  70                  75                  80

Ser Ala Leu Leu Ser Ser Asp Ile Thr Ala Ser Val Asn Cys Ala Lys
             85                  90                  95

Lys Ile Val Ser Asp Gly Asn Gly Met Asn Ala Trp Val Ala Trp Arg
            100                 105                 110

Asn Arg Cys Lys Gly Thr Asp Val Gln Ala Trp Ile Arg Gly Cys Arg
            115                 120                 125

Leu

<210> SEQ ID NO 48
<211> LENGTH: 129
<212> TYPE: PRT
<213> ORGANISM: Gallus gallus

<400> SEQUENCE: 48

Lys Val Phe Gly Arg Cys Glu Leu Ala Ala Ala Met Lys Arg His Gly
 1               5                  10                  15

Leu Asp Asn Tyr Arg Gly Tyr Ser Leu Gly Asn Trp Val Cys Val Ala
             20                  25                  30

Lys Phe Glu Ser Asn Phe Asn Thr Gln Ala Thr Asn Arg Asn Thr Asp
             35                  40                  45

Gly Ser Thr Asp Tyr Gly Ile Leu Gln Ile Asn Ser Arg Trp Trp Cys
 50                  55                  60

Asn Asp Gly Arg Thr Pro Gly Ser Arg Asn Leu Cys Asn Ile Pro Cys
 65                  70                  75                  80

Ser Ala Leu Leu Ser Ser Asp Ile Thr Ala Ser Val Asn Cys Ala Lys
```

```
                85                  90                  95
Lys Ile Val Ser Asp Gly Asn Gly Met Ser Ala Trp Val Ala Trp Arg
            100                 105                 110

Asn Arg Cys Lys Gly Thr Asp Val Gln Ala Trp Ile Arg Gly Cys Arg
            115                 120                 125

Leu

<210> SEQ ID NO 49
<211> LENGTH: 130
<212> TYPE: PRT
<213> ORGANISM: Homo sapiens

<400> SEQUENCE: 49

Lys Val Phe Glu Arg Cys Glu Leu Ala Arg Thr Leu Lys Arg Leu Gly
1               5                   10                  15

Met Asp Gly Tyr Arg Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys His Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
            115                 120                 125

Gly Val
    130

<210> SEQ ID NO 50
<211> LENGTH: 129
<212> TYPE: PRT
<213> ORGANISM: Bos taurus

<400> SEQUENCE: 50

Lys Val Phe Glu Arg Cys Glu Leu Ala Arg Thr Leu Lys Lys Leu Gly
1               5                   10                  15

Leu Asp Gly Tyr Lys Gly Val Ser Leu Ala Asn Trp Leu Cys Leu Thr
            20                  25                  30

Lys Trp Glu Ser Ser Tyr Asn Thr Lys Ala Thr Asn Tyr Asn Pro Ser
        35                  40                  45

Ser Glu Ser Thr Asp Tyr Gly Ile Phe Gln Ile Asn Ser Lys Trp Trp
    50                  55                  60

Cys Asn Asp Gly Lys Thr Pro Asn Ala Val Asp Gly Cys His Val Ser
65                  70                  75                  80

Cys Arg Glu Leu Met Glu Asn Asp Ile Ala Lys Ala Val Ala Cys Ala
                85                  90                  95

Lys His Ile Val Ser Glu Gln Gly Ile Thr Ala Trp Val Ala Trp Lys
            100                 105                 110

Ser His Cys Arg Asp His Asp Val Ser Ser Tyr Val Glu Gly Cys Thr
            115                 120                 125

Leu
```

<210> SEQ ID NO 51
<211> LENGTH: 147
<212> TYPE: PRT
<213> ORGANISM: Gallus gallus

<400> SEQUENCE: 51

```
Met Arg Ser Leu Leu Ile Leu Val Leu Cys Phe Leu Pro Leu Ala Ala
1               5                   10                  15

Leu Gly Lys Val Phe Gly Arg Cys Glu Leu Ala Ala Ala Met Lys Arg
            20                  25                  30

His Gly Leu Asp Asn Tyr Arg Gly Tyr Ser Leu Gly Asn Trp Val Cys
        35                  40                  45

Ala Ala Lys Phe Glu Ser Asn Phe Asn Thr Gln Ala Thr Asn Arg Asn
    50                  55                  60

Thr Asp Gly Ser Thr Asp Tyr Gly Ile Leu Gln Ile Asn Ser Arg Trp
65                  70                  75                  80

Trp Cys Asn Asp Gly Arg Thr Pro Gly Ser Arg Asn Leu Cys Asn Ile
                85                  90                  95

Pro Cys Ser Ala Leu Leu Ser Ser Asp Ile Thr Ala Ser Val Asn Cys
            100                 105                 110

Ala Lys Lys Ile Val Ser Asp Gly Asn Gly Met Asn Ala Trp Val Ala
        115                 120                 125

Trp Arg Asn Arg Cys Lys Gly Thr Asp Val Gln Ala Trp Ile Arg Gly
    130                 135                 140

Cys Arg Leu
145
```

<210> SEQ ID NO 52
<211> LENGTH: 321
<212> TYPE: PRT
<213> ORGANISM: Artificial Sequence
<220> FEATURE:
<223> OTHER INFORMATION: Synthetic Peptide

<400> SEQUENCE: 52

```
Met Ala Lys Ala Asp Gly Ser Leu Leu Tyr Tyr Asn Pro His Asn Pro
1               5                   10                  15

Pro Arg Arg Tyr Tyr Phe Tyr Met Ala Ile Phe Ala Val Ser Val Ile
            20                  25                  30

Cys Val Leu Tyr Gly Pro Ser Gln Gln Leu Ser Ser Pro Lys Ile Asp
        35                  40                  45

Ala Ser Ala Pro Ala Pro Val Lys Gln Gly Pro Thr Ser Val Ala Tyr
    50                  55                  60

Val Glu Val Asn Asn Asn Ser Met Leu Asn Val Gly Lys Tyr Thr Leu
65                  70                  75                  80

Ala Asp Gly Gly Gly Asn Ala Phe Asp Val Ala Val Ile Phe Ala Ala
                85                  90                  95

Asn Ile Asn Tyr Asp Thr Gly Thr Lys Thr Ala Tyr Leu His Phe Asn
            100                 105                 110

Glu Asn Val Gln Arg Val Leu Asp Asn Ala Val Thr Gln Ile Arg Pro
        115                 120                 125

Leu Gln Gln Gln Gly Ile Lys Val Leu Ser Val Leu Gly Asn His
    130                 135                 140

Gln Gly Ala Gly Phe Ala Asn Phe Pro Ser Gln Gln Ala Ala Ser Ala
145                 150                 155                 160

Phe Ala Lys Gln Leu Ser Asp Ala Val Ala Lys Tyr Gly Leu Asp Gly
```

```
                165                 170                 175
Val Asp Phe Asp Asp Glu Tyr Ala Glu Tyr Gly Asn Asn Gly Thr Ala
            180                 185                 190

Gln Pro Asn Asp Ser Ser Phe Val His Leu Val Thr Ala Leu Arg Ala
            195                 200                 205

Asn Met Pro Asp Lys Ile Ile Ser Leu Tyr Asn Ile Gly Pro Ala Ala
        210                 215                 220

Ser Arg Leu Ser Tyr Gly Gly Val Asp Val Ser Asp Lys Phe Asp Tyr
225                 230                 235                 240

Ala Trp Asn Pro Tyr Tyr Gly Thr Trp Gln Val Pro Gly Ile Ala Leu
            245                 250                 255

Pro Lys Ala Gln Leu Ser Pro Ala Ala Val Glu Ile Gly Arg Thr Ser
            260                 265                 270

Arg Ser Thr Val Ala Asp Leu Ala Arg Arg Thr Val Asp Glu Gly Tyr
            275                 280                 285

Gly Val Tyr Leu Thr Tyr Asn Leu Asp Gly Gly Asp Arg Thr Ala Asp
        290                 295                 300

Val Ser Ala Phe Thr Arg Glu Leu Tyr Gly Ser Glu Ala Val Arg Thr
305                 310                 315                 320

Pro

<210> SEQ ID NO 53
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 53

Glu Ala Glu Ala
1
```